US012747442B2

(12) United States Patent
Viollier et al.

(10) Patent No.: US 12,747,442 B2
(45) Date of Patent: Sep. 29, 2026

(54) FlmG-DEPENDENT SOLUBLE PROTEIN O-GLYCOSYLATION SYSTEMS IN BACTERIA

(71) Applicant: UNIVERSITE DE GENEVE, Geneva (CH)

(72) Inventors: Patrick Viollier, Mies (CH); Silvia Ardissone, Geneva (CH); Nicolas Kint, Annemasse (FR)

(73) Assignee: UNIVERSITE DE GENEVE, Geneva (CH)

( * ) Notice: Subject to any disclaimer, the term of this patent is extended or adjusted under 35 U.S.C. 154(b) by 558 days.

(21) Appl. No.: 18/031,684

(22) PCT Filed: Oct. 15, 2021

(86) PCT No.: PCT/EP2021/078565
§ 371 (c)(1),
(2) Date: Apr. 13, 2023

(87) PCT Pub. No.: WO2022/079220
PCT Pub. Date: Apr. 21, 2022

(65) Prior Publication Data
US 2024/0035036 A1 Feb. 1, 2024

(30) Foreign Application Priority Data
Oct. 15, 2020 (EP) .................................... 20202114

(51) Int. Cl.
*C12N 15/52* (2006.01)
*C12N 9/10* (2006.01)
*C12P 21/00* (2006.01)

(52) U.S. Cl.
CPC ........... *C12N 15/52* (2013.01); *C12N 9/1051* (2013.01); *C12P 21/005* (2013.01)

(58) Field of Classification Search
CPC ..... C12N 15/52; C12N 9/1051; C12P 21/005; C12Y 204/01
See application file for complete search history.

(56) References Cited

PUBLICATIONS

Anderson et al., FlbT, the post-transcriptional regulator of flagellin synthesis in Caulobacter crescentus, interacts with the 5' untranslated region of flagellin mRNA. Mol. Microbiol., 2000, vol. 38(1): 41-52. (Year: 2000).*
Ardissone et al., Interplay between flagellation and cell cycle control in Caulobacter. Current Opin. Micorbiol., 2015, vol. 28: 83-92. (Year: 2015).*
Banerjee et al., Improving enzymes for biomass conversion: A basic research perspective. Bioenerg. Res., 2010, vol. 3: 82-92. (Year: 2010).*
Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Johnson et al., Synthesis and Assembly of Flagellar Components by Caulobacter crescentus Motility Mutants . J. Bacteriol., 1983, vol. 154(3): 1137-1144. (Year: 1983).*
Marks et al., The Genetic Basis of Laboratory Adaptation in Caulobacter crescentus. J. Bacteriol., 2010, vol. 192: 3678-3688 (Year: 210).*
Nierman et al., Complete genome sequence Caulobacter crescentus. PNAS., 2001, vol. 98(7): 4136-4141. (Year: 2001).*
Power et al., The genetics of glycosylation in Gram-negative bacteria. FEMS Microbiol., 2003, vol. 218: 211-222. (Year: 2003).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Ud-Din et al., Flagellin glycosylation with pseudaminic acid in Campylobacter and Helicobacter: prospects for development of novel therapeutics. Cell. Mol. Life Sci., 2018, vol. 75: 1163-1178. (Year: 2018).*
Yi et al., Prokaryotic expression and mechanism of action of α-helical antimicrobial peptide A20L using fusion tags. BMC Biotechnol , 2015, vol. 15:69, pp. 1-10. (Year: 2015).*
International Search Report from corresponding PCT Application No. PCT/EP2021/078565 dated Apr. 4, 2022.
Written Opinion from corresponding PCT Application No. PCT/EP2021/078565 dated Apr. 4, 2022.
Anonymous, "UniParc—UPI000BD59FC1", (2017).
Anonymous, "UniParc—UP1000BB4E000" (2017).

(Continued)

*Primary Examiner* — Ganapathirama Raghu
(74) *Attorney, Agent, or Firm* — Harness Dickey & Pierce P.L.C.

(57) ABSTRACT

The present disclosure relates to a polynucleotide flmG which encodes Flagellin Modification Protein (FlmG) having glycosyltransferase activity, as well as a recombinant expression vector for bacterial expression comprising a polynucleotide flmG. Also provided is a prokaryotic protein glycosylation kit for soluble O-glycosylation comprising a bacterial Gram-negative host expressing at least one copy of the recombinant expression vector described herein and a process for O-glycosylation of a soluble acceptor protein of interest.

3 Claims, 5 Drawing Sheets

Specification includes a Sequence Listing.

(56) References Cited

PUBLICATIONS

Ardissone, S., et al., "Specificity in glycosylation of multiple flagellins by the modular and cell cycle regulated glycosyltransferase FlmG," Elife, 9: 1-28 (2020).
Leclerc, G., et al., "A New Class of Caulobacter crescentus Flageller Genes," Journal of Bacteriology, 180(19): 5010-5019 (1998).
Ardissone, S. & Viollier, P.H., "Interplay between flagellation and cell cycle control in Caulobacter," Current Opinion in Microbiology, 28: 83-92 (2015).

* cited by examiner

[Fig. 1]
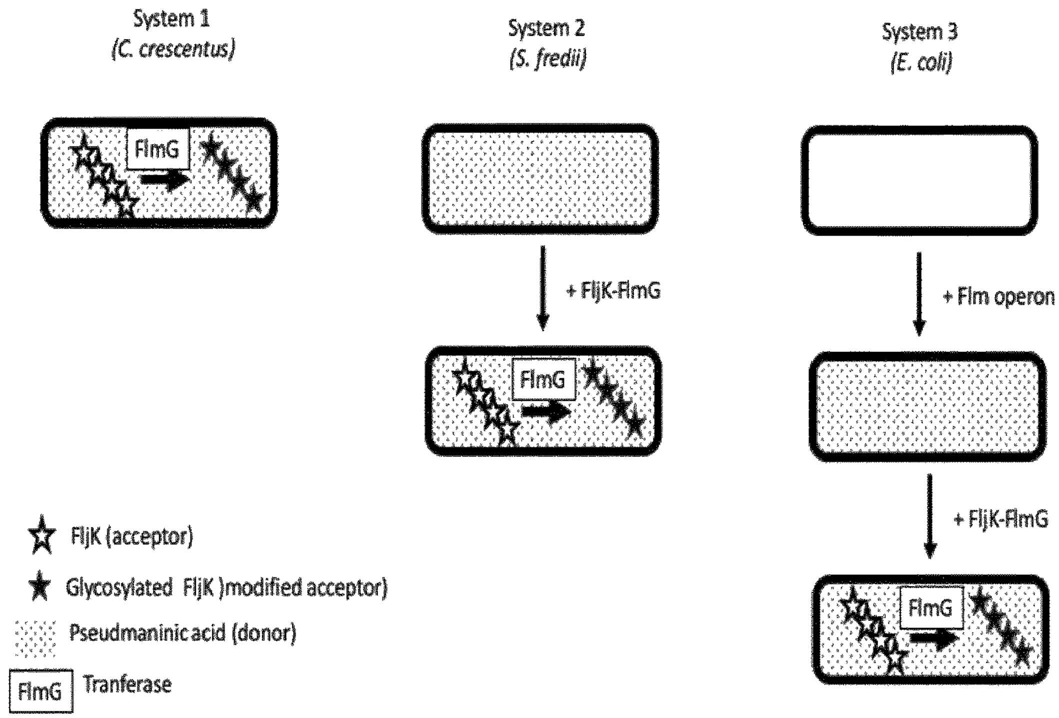
[Fig. 2]
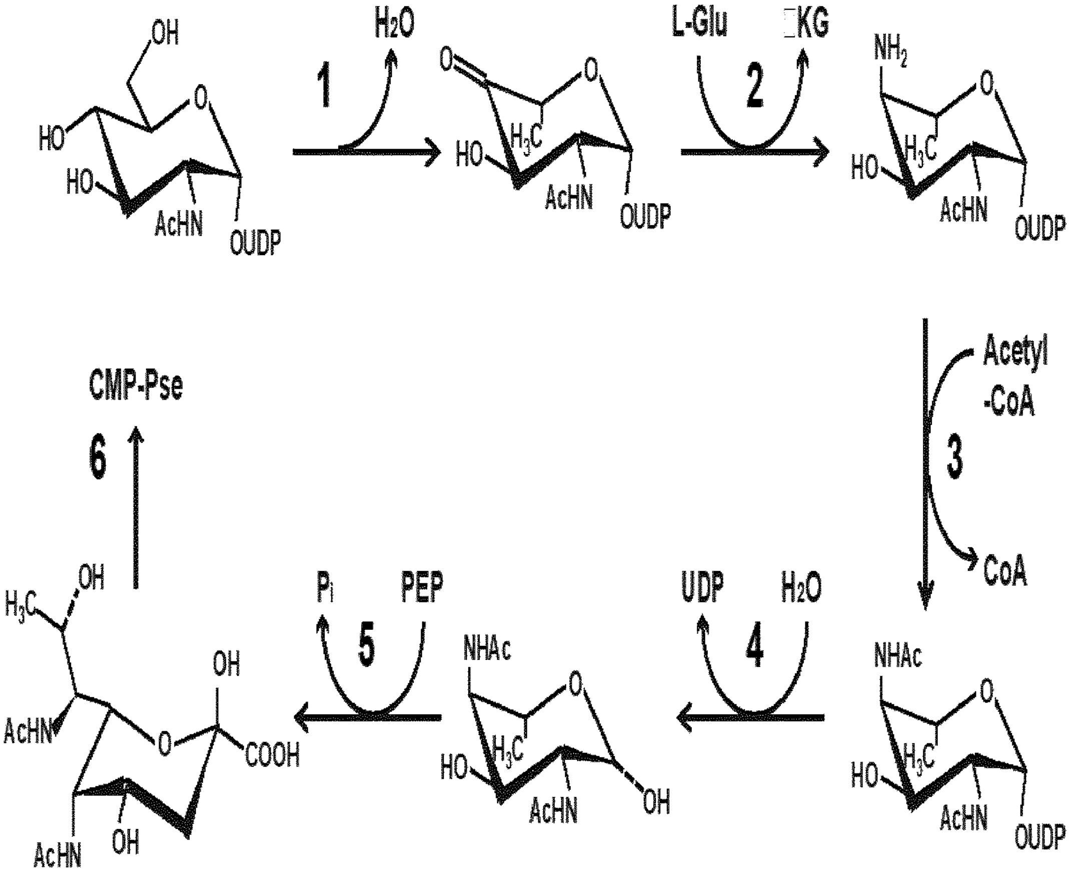

[Fig.3]
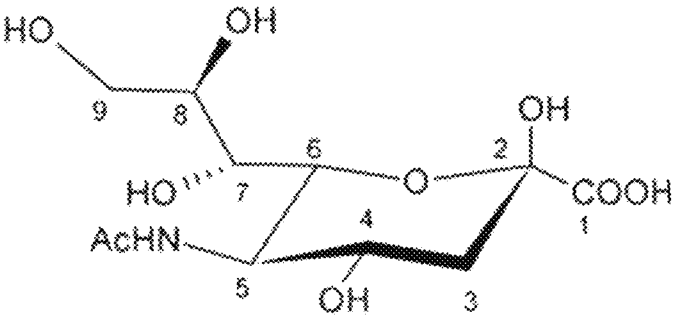
Sialic acid
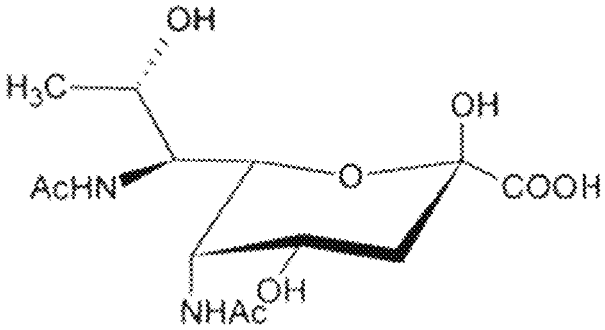
Pseudaminic acid
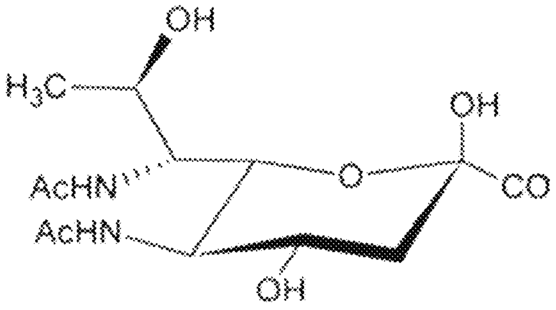
Legionaminic acid

[Fig. 4]
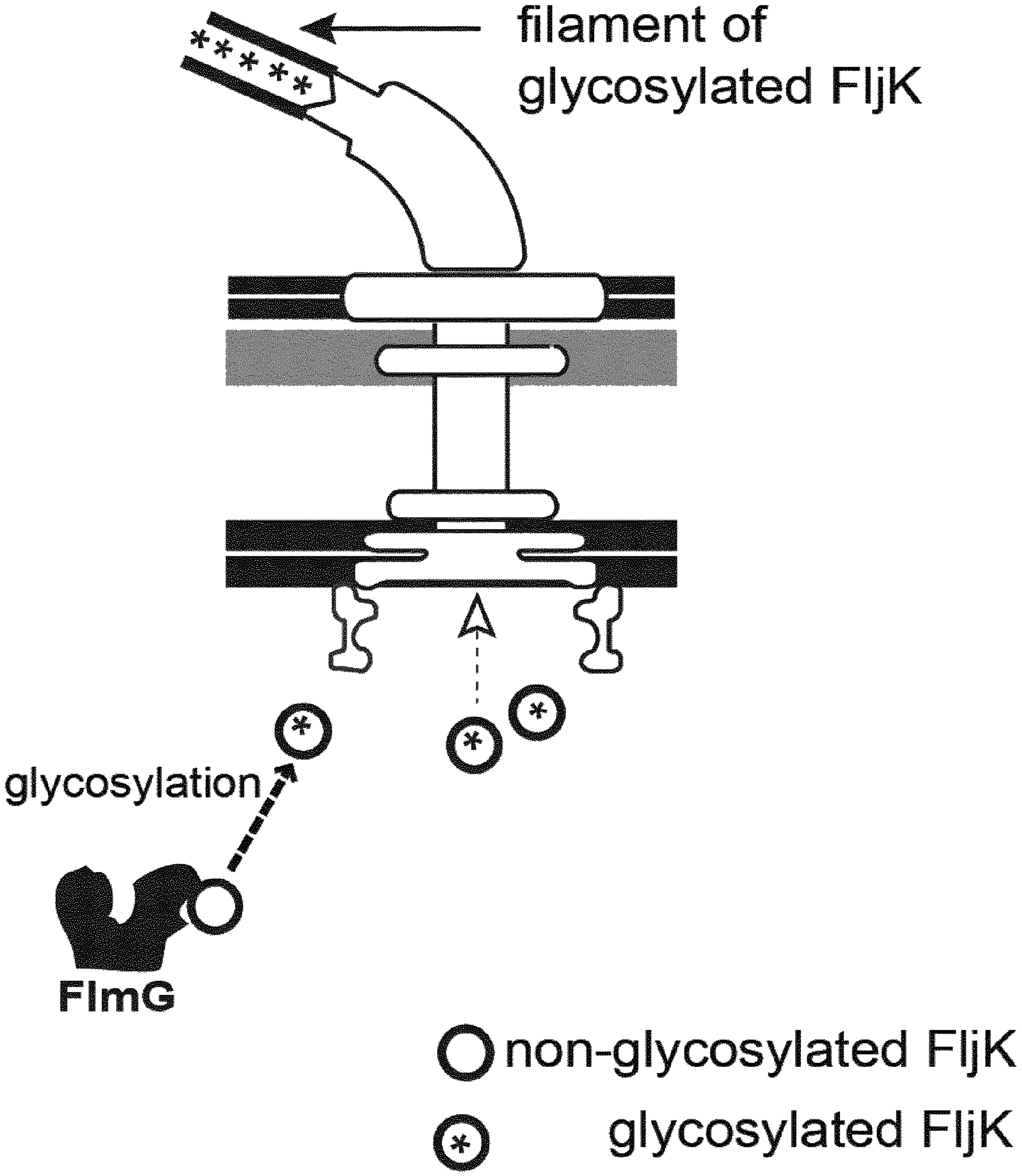

[Fig. 5]
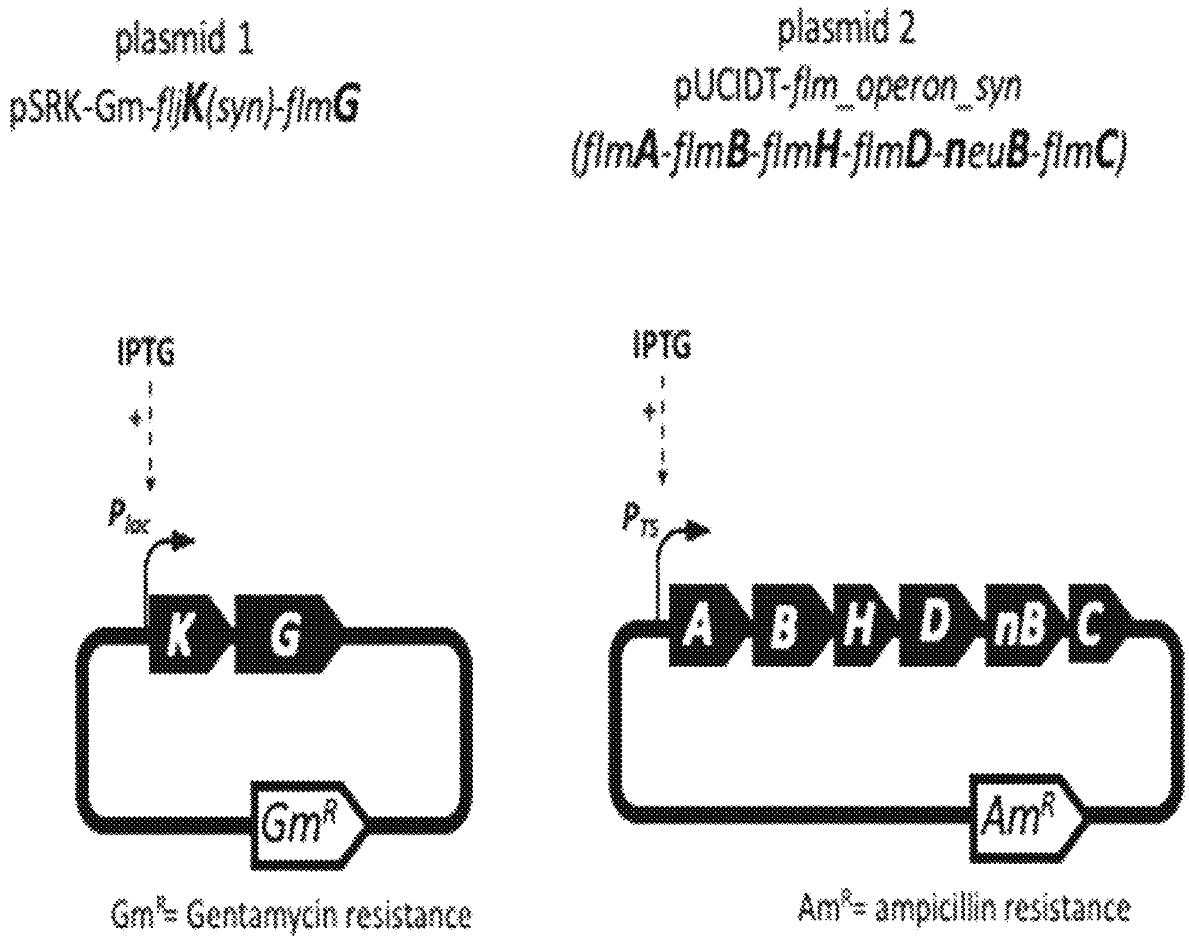

[Fig. 6]
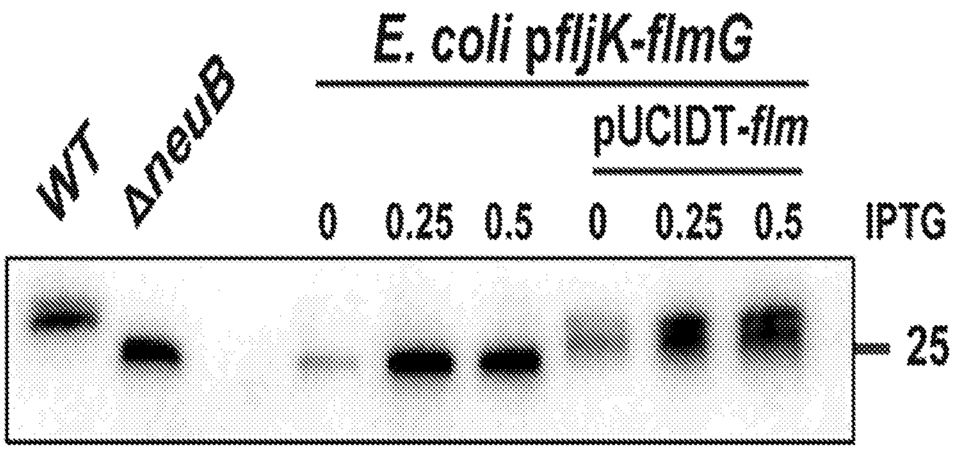
[Fig. 7]
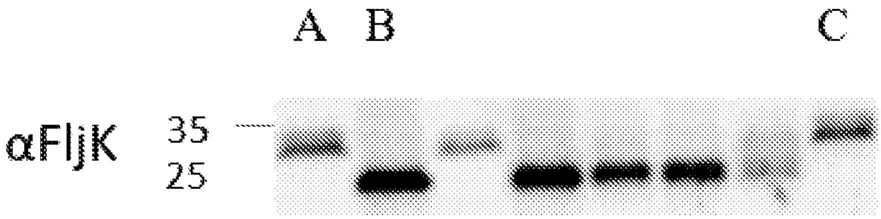

FlmG-DEPENDENT SOLUBLE PROTEIN O-GLYCOSYLATION SYSTEMS IN BACTERIA

PRIORITY STATEMENT

This application is a national stage application under 35 U.S.C. § 371 of PCT International Application No. PCT/EP2021/078565, which has an international filing date of 15 Oct. 2021 and claims priority under 35 U.S.C. § 119 to European Patent Application No. 20202114.3 filed on 15 Oct. 2020. The contents of each application recited above are incorporated herein by reference in their entirety.

REFERENCE TO AN ELECTRONIC SEQUENCE LISTING

This application contains references to amino acid sequences and/or nucleic acid sequences which have been submitted concurrently herewith as the sequence listing text file entitled "Sequence_listing.txt", file size 133,375 Bytes (B), created on 13 Apr. 2023. The aforementioned sequence listing is hereby incorporated by reference in its entirety.

TECHNICAL FIELD

The invention relates to a polynucleotide flmG which encodes Flagellin Modification Protein (FlmG) having a glycosyltransferase activity as well as a recombinant expression vector for bacterial expression comprising the polynucleotide flmG of the invention. Also provided is a prokaryotic protein glycosylation kit for soluble O-based glycosylation comprising a bacterial Gram-negative host expressing at least one copy of the recombinant expression vector of the invention and a process for O-glycosylation of soluble proteins of interest.

BACKGROUND ART

Glycosyltransferases (GT) are enzymes that post-translationally transfer monomeric and polymeric glycosyl moieties from an activated nucleoside sugar to acceptor molecules (e.g., other sugars, proteins, lipids, and other organic substrates). Thus, these enzymes utilize an activated donor sugar substrate that contains a substituted phosphate leaving group. Donor sugar substrates (i.e., the "glycosyl donor") are commonly activated as nucleoside diphosphate sugars. However, other sugars, such as nucleoside monophosphate sugars, lipid phosphates and unsubstituted phosphates are also used (See e.g., Lairson et al., Ann. Rev. Biochem., 77:25.1-25.35 [2008])[1].

These glycosylated products are involved in various metabolic pathways and processes. Indeed, the biosynthesis of numerous disaccharides, oligosaccharides, and polysaccharide donors is needed for the action of various glycosyltransferases and its acceptors. The transfer of a glucosyl moiety can alter the acceptor's bioactivity, solubility, and transport properties within cells. GTs have found use in the targeted synthesis of specific compounds (e.g., glycoconjugates and glycosides), as well as the production of differentially glycosylated drug, biological probes or natural product libraries.

Indeed, post-translational protein modification is essential for various facets in cellular biology, ranging from gene regulation to the organization of cellular structures. In all cases, biological function underlies the capacity to specifically identify and modify the correct target protein. Posttranslational modification of proteins by glycosylation is therefore also fundamental to human health and valuable for therapeutic treatment in disease. Glycosylation can influence protein activity and/or stability, particularly in serum, an aspect that is particularly pertinent for the recombinant production of effective therapeutic proteins. As cellular dysfunction is often brought about by an insufficiency of glycosylated proteins, developing custom-designed engineering strategies for glycosylation of selected acceptor proteins is a priority in therapeutic biotechnology including the production of recombinant glycoproteins. Exquisite control mechanisms must be in place to ensure modification of the designated target/acceptor, a feat that is more convoluted for proteins that are destined for the cell surface or the exterior and must first be modified in the cytoplasm by dedicated glycosyltransferases.

Marie-Eve Lalonde et al. "Therapeutic glycoprotein production in mammalian cells" Journal of Biotechnology 251 (2017) 128-140 [2] disclose that over the last years, the biopharmaceutical industry has significantly turned its biologics production towards mammalian cell expression systems. The presence of glycosylation machineries within these systems, and the fact that monoclonal antibodies represent today the vast majority of new therapeutic candidates, has largely influenced this new direction, since no suitable expression systems for glycosylated proteins exist in bacteria, eventhough bacteria are otherwise excellent hosts for large-scale protein production. Recombinant glycoproteins, including monoclonal antibodies, have shown different biological properties based on their glycan profiles. Thus, the industry has developed cell engineering strategies not only to improve cell's specific production, but also to adapt their glycosylation profiles for increased therapeutic activity. Additionally, the advance of "omics" technologies has recently given rise to new possibilities in improving these expression platforms and will significantly help developing new strategies, in particular for CHO (Chinese Hamster Ovary) cells.

However, Carlos Alexandre Breyer et al. "Expression of Glycosylated Proteins in Bacterial System and Purification by Affinity Chromatography" Recombinant Glycoprotein Production: Methods and Protocols, Methods in Molecular Biology, vol. 1674, DOI 10.1007/978-1-4939-7312-5_14 [3], disclose that the bacterial expression of glycoproteins has experienced significant progress in recent years, particularly in regard to the production of conjugate vaccines against pathogens. In this case, a protein carrier conjugated with glycosides is used to produce intense stimulation of the immune system against the polysaacharides that is found on the pathogen surface. Glycoconjugate vaccines account for 35% of the global vaccine market, and consequently, several biotechnological companies have developed products for the purification of glycosylated proteins to attain homogeneity. The authors have presented a general process for glycoprotein production in *Escherichia coli* and a practice method for purification of glycosylated proteins, using affinity chromatography. For some time, it was believed that glycosylation occurred solely in eukaryotes; however, the process has been reported in other organisms such as archaea and bacteria. In particular, in this article the use of modified *E. coli* strains (ΔwaaL), expressing a specific oligosaccharide, a carrier protein, and PglB, has been suggested as a simple, low-cost alternative to glycoprotein production for glycoconjugate vaccines intended to target polysaccharides of pathogens.

Emilie Kay et al. "Recent advances in the production of recombinant glycoconjugate vaccines" npj Vaccines (2019) 4:16; doi.org/10.1038/s41541-019-0110-z[4] disclose that glycoconjugate vaccines against bacteria are one of the success stories of modern medicine and have led to a significant reduction in the global occurrence of bacterial meningitis and pneumonia. Glycoconjugate vaccines are produced by covalently linking a bacterial polysaccharide (usually capsule, or more recently O-antigen), to a carrier protein. Given the success of glycoconjugate vaccines, it is surprising that to date only vaccines against *Haemophilus influenzae* type b, *Neisseria* meningitis and *Streptococcus pneumoniae* have been fully licensed. This is set to change through the glycoengineering of recombinant vaccines in bacteria, such as *Escherichia coli*, that act as mini factories for the production of an inexhaustible and renewable supply of pure vaccine product. The recombinant process, termed Protein Glycan Coupling Technology (PGCT) or bioconjugation, offers a low-cost option for the production of pure glycoconjugate vaccines, with the in-built flexibility of adding different glycan/protein combinations for custom made vaccines. Numerous vaccine candidates have now been made using PGCT, which include those improving existing licensed vaccines (e.g., pneumococcal), entirely new vaccines for both Gram-positive and Gram-negative bacteria, and (because of the low production costs) veterinary pathogens. Given the continued threat of antimicrobial resistance and the potential peril of bioterrorist agents, the production of new glycoconjugate vaccines against old and new bacterial foes is particularly timely. This article reviews the component parts of bacterial PGCT, including recent advances, the advantages and limitations of the technology, and future applications and perspectives.

Glycosylation can occur via N-linkage (at asparagine residues) or via O-linkage (at serine or threonine residues)[5]. It is now very clear that N- and O-linked glycosylation systems are also encoded in many different bacterial lineages, but not in all of them. For example, the model bacterium *Escherichia coli* K12, the preeminent workhorse for protein production at an industrial scale particularly soluble (cytoplasmic) proteins, lacks such glycosylation systems.

Bacterial N-glycosylation systems have been extensively studied and re-engineered. However, these systems typically operate at the membrane because the donor sugar molecule is synthesized on a lipid carrier. A such membrane-anchored topology of the glycosylation reaction poses challenges for industrial production of glycosylated proteins in *E. coli*, soluble systems are in high demand and actively being developed. Recently, a soluble version of a bacterial N-glycosylation system has been engineered that can function in the *E. coli* cytoplasm[6].

Since O-linked glycosylation is wide-spread among human peptide hormones and blood/coagulation factors which are soluble proteins or peptides, it would be desirable to have a soluble O-based glycosylation system allowing to perform the O-glycosylation of soluble proteins of interest. However, no such soluble O-glycosylation systems have been provided to date.

Soluble O-glycosylation exists naturally in several (but not all) flagellated bacteria where they serve to glycosylate flagellin proteins in the cytoplasm before they are exported and assembled into the flagellar filament. In these cases, the capacity to glycosylate flagellin with a specific sialic acid is needed for flagellin to be assembled into a flagellar filament. Only very recently have the proteins responsible for this O-glycosylation, the O-specific glycosyltransferases (OGTs), been implicated by virtue of their requirement for flagellar function[7,8].

However, no industrially usable glycosylation system allowing O-glycosylation of soluble proteins of interest in a bacterial host has ever been disclosed. There is a particular need for providing such a system in a bacteria that is well suited for industrial production of diverse proteins, such as *E. coli*. It is an object of the invention to solve this problem.

SUMMARY OF INVENTION

With the discovery of the founding member of the FlmG-family of soluble OGTs from the flagellated bacterium *Caulobacter crescentus*, the present inventors could demonstrate that FlmG uses a soluble sialic acid donor molecule, pseudaminic acid, to glycosylate flagellin (FljK) in the natural host *C. crescentus*. FlmG has a modular organization, with an N-terminal domain (NTD) that binds the flagellin and a C-terminal domain (CTD) suggesting that the NTD tethers the OGT to the acceptor to allow proximity-based glycosylation.

The simple modular domain organization of FlmG makes it a suitable system for being re-engineered into an efficient soluble O-glycosylation platform for the large scale production of glycosylated proteins in the cytoplasm of Gram-negative bacterial hosts, including *E. coli*.

The present invention provides an O-glycosylation systems allowing for O-glycosylation of an heterologous acceptor protein of interest in a Gram-negative bacterial host that produces the sugar donor pseudaminic acid and expresses an FlmG glycosyltransferase, wherein such Gram-negative bacteria is transformed with an acceptor protein to be glycosylated.

In a first aspect, the invention provides a polynucleotide flmG which encodes Flagellin Modification Protein (FlmG) having a glycosyltransferase activity and being selected from the group consisting of the following (a) to (d):

a) a polynucleotide composed of SEQ ID NO: 26 or a polynucleotide encoding SEQ ID NO: 27;
b) a polynucleotide that hybridizes under stringent conditions with a polynucleotide sequence complementary to SEQ ID NO: 26 or with a polynucleotide sequence encoding SEQ ID NO: 27, and which encode a protein having activity that transfers a soluble monosaccharide to the hydroxyl group on threonine residues of soluble acceptor proteins;
c) a polynucleotide that encodes a protein composed of an amino acid sequence in which one or a plurality of amino acids have been deleted, substituted, inserted and/or added in the amino acid sequence of SEQ ID NO: 27, and has activity that transfers a soluble monosaccharide to the hydroxyl group on threonine residues of soluble acceptor proteins; and,
d) a polynucleotide that encodes a protein that has an amino acid sequence having identity of 90% or more with the amino acid sequence of SEQ ID NO: 27 and has activity that transfers a soluble monosaccharide to the hydroxyl group on threonine residues of soluble acceptor proteins;

wherein glycosylation is a O-based glycosylation of said soluble acceptor proteins in the presence of said monosaccharide which is performed within the cytoplasm of bacterial Gram-negative cells.

A second object of the invention is to provide a recombinant expression vector for bacterial expression comprising the polynucleotide flmG of the invention.

A third object of the invention is to provide a prokaryotic protein glycosylation kit for soluble O-based glycosylation comprising a bacterial Gram-negative host that produces a soluble monosaccharide donor and expresses an Flagellin Modification Protein (FlmG), wherein such Gram-negative host expresses at least one copy of a recombinant expression vector comprising a polynucleotide sequence encoding a soluble acceptor protein of interest.

A fourth object of the present invention is a process for for O-glycosylation of a soluble acceptor protein, comprising:

a) transforming a bacterial Gram-negative host that produces a soluble monosaccharide donor and expresses Flagellin Modification Protein (FlmG) with at least one copy of a recombinant expression vector comprising a polynucleotide sequence encoding a soluble acceptor protein of interest;
b) growing the Gram-negative host under conditions suitable to the expression of the soluble acceptor protein of interest; and
c) isolating the glycosylated soluble protein of interest from the host.

Other objects and advantages of the invention will become apparent to those skilled in the art from a review of the ensuing detailed description, which proceeds with reference to the following illustrative drawings, and the attendant claims.

BRIEF DESCRIPTION OF DRAWINGS

FIG. 1: FIG. 1 is a scheme of 3 different glycosylation systems:

System 1 (*Caulobacter crescentus*, native):

Donor: Pseudaminic acid produced naturally from Flm biosynthetic enzymes encoded in the flm genes on the *C. crescentus* chromosome Acceptor: FljK flagellin protein produced naturally from fljK gene encoded on the *C. crescentus* chromosome.

Transferase: FlmG protein produced naturally from flmG gene encoded on on the *C. crescentus* chromosome.

System 2 (*Sinorhizobium fredii* NGR234, artificial):

Donor: Pseudaminic acid produced naturally from enzymes encoded on chromosome.

Acceptor: FljK flagellin protein produced from synthetic fljK gene encoded on pSRK-Gm fljK(syn)-flmG.

Transferase: FlmG protein produced from flmG gene encoded on pSRK-Gm fljK(syn)-flmG.

System 3 (*E. coli*, artificial):

Donor: Pseudaminic acid produced from synthetic Flm enzymes encoded on plasmid pUCIDT-flm-operon syn.

Acceptor: FljK flagellin protein produced from synthetic fljK gene encoded on pSRK-Gm fljK(syn)-flmG.

Transferase: FlmG protein produced from flmG gene encoded on pSRK-Gm fljK(syn)-flmG.

FIG. 2 illustrates the biosynthetic operon encoding pseudaminic acid biosynthesis pathway of *Caulobacter crescentus* encoded on its chromosome. These steps are catalyzed by the following enzymes starting with UDP-N-acetylglucosamine to yield CMP-pseudaminic acid (CMP-Pse), 1 FlmA, 2 FlmB, 3 FlmH, 4 FlmD, 5 NeuB and 6 FlmC.

FIG. 3 represents a list of possible donors of soluble monosaccharides.

FIG. 4 illustrates the glycosylation of the FljK flagellin (circle) in the cytoplasm by the FlmG OGT which binds the FljK directly via a flagellin binding domain located at the N-terminus of FlmG. Once flagellin is glycoslyted (indicated by the star in the circle), then FljK is exported via the flagellar secretion apparatus and can assemble into the flagellar filament on the surface of bacterial cells.

FIG. 5 illustrates the two plasmids used for reconstitution of FljK glycosylation by FlmG (plasmid 1) s, pSRK-Gm-fljK(syn)-flmG, in *E. coli* cells producing pseudaminic acid. Pseudaminic acid production is achieved by *E. coli* cells in the presence of plasmid 2, pUCIDT-flm_operon_syn which encodes all six genes required for pseudaminic acid synthesis from the *E. coli* phage T5 promoter that can be induced by the addition of isopropyl-β-D-thiogalactopyranosid (IPTG).

FIG. 6 illustrates an immunoblot showing the difference in migration of Fljk expressed in the presence of FlmG (plasmid 1) in *E. coli* cells harbouring or not plasmid 2 (pUCIDT-flm_operon_syn). Protein expression was induced by the addition of isopropyl-β-D-thiogalactopyranosid (IPTG).

FIG. 7 illustrates an immunoblot showing the difference in migration of FLjK in the wild-type *Caulobacter Crescentus* (A), in mutant cells in which the in-frame deletion in flmG (ΔflmG) (B) and in ΔflmG mutant cells further transformed with a plasmid comprising the sequence of the variant FlmG having the sequence SEQ ID NO: 27 (C). Protein glycosylation was induced by the variant FlmG having the sequence SEQ ID NO: 27, in a similar extent as in the wild-type *Caulobacter crescentus.*

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control.

Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

As used in the specification and claims, the singular forms "a", "an" and "the" include plural references unless the context clearly dictates otherwise.

"A purified and isolated DNA molecule or sequence" refers to the state in which the nucleic acid molecule is free or substantially free of material with which it is naturally associated such as other polypeptides or nucleic acids with which it is found in its natural environment, or the environment in which it is prepared (e.g. cell culture) when such preparation is by recombinant nucleic acid technology practiced in vitro or in vivo.

The terms "nucleic acid", "polynucleotide," and "oligonucleotide" are used interchangeably and refer to any kind of deoxyribonucleotide (e.g. DNA, cDNA, . . . ) or ribonucleotide (e.g. RNA, miRNA, . . . ) polymer or a combination of deoxyribonucleotide and ribonucleotide (e.g. DNA RNA) polymer, in linear or circular conformation, and in either single- or double-stranded form. These terms are not to be construed as limiting with respect to the length of a polymer and can encompass known analogues of natural nucleotides, as well as nucleotides that are chemically modified in the base, sugar and/or phosphate moieties.

In addition, the DNA according to the present invention can be obtained by a method known among persons with ordinary skill in the art, such as methods in which DNA is synthesized chemically such as the phosphoamidide method, or nucleic acid amplification methods that use a nucleic acid sample of a plant as a template and use primers designed based on the nucleotide sequence of a target gene.

With "variants" or "variants of a sequence" is meant a nucleic acid sequence that vary form the reference sequence by conservative nucleic acid substitutions, whereby one or more nucleic acids are substituted by another with same characteristics. Variants encompass as well degenerated sequences, sequences with deletions and insertions, as long as such modified sequences exhibit the same function (functionally equivalent) as the reference sequence.

"Fragments" refer to sequences sharing at least 40% amino acids in length with the respective sequence of the substrate active site. These sequences can be used as long as they exhibit the same biological properties as the native sequence from which they derive. Preferably these sequences share more than 70%, preferably more than 80%, in particular more than 90%, and even more than 95% amino acids in length with the respective sequence the substrate active site. These fragments can be prepared by a variety of methods and techniques known in the art such as for example chemical synthesis.

The present invention also includes variants of the aforementioned sequences, that is nucleotide sequences that vary from the reference sequence by conservative nucleotide substitutions, whereby one or more nucleotides are substituted by another with same characteristics. Variants encompass as well degenerated sequences, sequences with deletions and insertions, as long as such modified sequences exhibit the same biological function (functionally equivalent) as the reference sequence.

Molecular chimera of the aforementioned sequences are also considered in the present invention. By molecular chimera is intended a nucleotide sequence that may include a functional portion of the isolated DNA molecule according to the invention and that will be obtained by molecular biology methods known by those skilled in the art.

Particular combinations of isolated DNA molecules or fragments or sub-portions thereof are also considered in the present invention. These fragments can be prepared by a variety of methods known in the art. These methods include, but are not limited to, digestion with restriction enzymes and recovery of the fragments, chemical synthesis or polymerase chain reactions (PCR).

The term "functionally or operably linked" refers to a juxtaposition wherein the components are in a relationship permitting them to function in their intended manner (e.g. functionally linked).

As used herein, the term "promoter" refers to a nucleic acid sequence that regulates expression of a gene. A promoter sequence is a DNA regulatory region capable of binding RNA polymerase in a cell and initiating transcription of a downstream (3' direction) coding sequence. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine Dalgarno sequences in addition to the −10 and −35 consensus sequences.

A "hybrid promoter" as used herein refers to a promoter comprising two or more regulatory regions or domains, which are from different origins, i.e. which do not occur together in the nature.

An "enhancer" is a nucleotide acid sequence that acts to potentiate the transcription of genes independent of the identity of the gene, the position of the sequence in relation to the gene, or the orientation of the sequence.

An "operon" is a group of closely linked genes that produces a single messenger RNA molecule in transcription and that consists of structural genes and regulating elements (such as an operator and promoter).

The terms "vector" and "plasmid" are used interchangeably, as the plasmid is the most commonly used vector form. However, the invention is intended to include such other forms of expression vectors, including, but not limited to, viral vectors (e.g., retroviruses (including lentiviruses), adenoviruses and adeno-associated viruses), which serve equivalent functions. Preferably, the expression vector according to the invention is a retroviral expression vector.

The expression vector of the invention can be in the form of a linear or a circular DNA sequence. "Linear DNA" denotes non-circular DNA molecules having free 5' and 3' ends. Linear DNA can be prepared from closed circular DNA molecules, such as plasmids, by enzymatic digestion or physical disruption. "Circular DNA" denotes non-circular DNA molecules having free 5' and 3' ends. The vectors or constructs as used herein broadly encompass any recombinant DNA material that is capable of transferring DNA from one cell to another.

Those skilled in the art will appreciate that a variety of enhancers, promoters, and genes are suitable for use in the constructs of the invention, and that the constructs will contain the necessary start, termination, and control sequences for proper transcription and processing of the gene of interest when the construct is introduced into a host cell. The constructs may be introduced into cells by a variety of gene transfer methods known to those skilled in the art, for example, gene transfection, lipofection, microinjection, electroporation, transduction and infection. It is preferred that the constructs of the invention integrate stably into the genome of specific and targeted cell types.

A "gene" is a deoxyribonucleotide (DNA) sequence coding for a given mature protein. As used herein, the term "gene" shall not include untranslated flanking regions such as RNA transcription initiation signals, polyadenylation addition sites, promoters or enhancers.

The polynucleotide (nucleic acid, gene) of the present invention is that which "encodes" a protein of interest. Here, the term "encode" refers to expressing a protein of interest in a state in which it retains its activity. In addition, the term "encode" includes both the meanings of encoding a protein of interest in the form of a contiguous structural sequence (exon) and encoding a protein of interest mediated by an inclusion sequence (intron).

The "gene of interest" or "transgene" is preferably a gene which encodes a protein (structural or regulatory protein). The proteins may be "homologous" to the host (i.e., endogenous to the host cell being utilized), or "heterologous," (i.e., foreign to the host cell being utilized), such as a human protein produced by a bacteria. The protein may be produced as a soluble protein in the cytoplasm of a bacteria. Examples of proteins include soluble proteins such as antibodies, hormones such as growth hormone, growth factors such as epidermal growth factor, analgesic substances like enkephalin, enzymes like chymotrypsin, and receptors to hormones or growth factors and includes as well proteins usually used as a visualizing marker e.g. green fluorescent protein.

The gene of interest may also code for a polypeptide of diagnostic use or therapeutic use. The polypeptide may be produced in bioreactors in vitro using various host cells (e.g., prokaryote cells) containing the expression vector of the invention.

The gene of interest may also code for an antigenic polypeptide for use as a vaccine. Antigenic polypeptides or nucleic acid molecules are derived form pathogenic organisms such as, for example, a bacterium or a virus.

Further, the genes may encode a precursor of a particular protein, or the like, which is modified intracellularly after translation to yield the molecule of interest.

Further examples of genes to be used in the invention may include, but are not limited to enzyme-encoding genes.

A "recombinant" prokaryotic cell according to the present invention is a prokaryotic cell containing a transgene as defined above.

As used herein, the terms "peptide", "protein", "polypeptide", "polypeptidic" and "peptidic" are used interchangeably to designate a series of amino acid residues connected to the other by peptide bonds between the alpha-amino and carboxy groups of adjacent residues.

A "part" or fragment of a peptide of the invention refers to a sequence containing less amino acids in length than the sequence of the peptide. This sequence can be used as long as it exhibits the same properties as the native sequence from which it derives. Preferably this sequence contains less than 90%, preferably less than 60%, in particular less than 30% amino acids in length than the respective sequence of the peptide of the invention.

The present invention also includes a variant of the peptide of the invention. The term "variant" refers to a peptide having an amino acid sequence that differ to some extent from a native sequence peptide, that is an amino acid sequence that vary from the native sequence by conservative amino acid substitutions, whereby one or more amino acids are substituted by another with same characteristics and conformational roles. The amino acid sequence variants possess substitutions, deletions, and/or insertions at certain positions within the amino acid sequence of the native amino acid sequence. Conservative amino acid substitutions are herein defined as exchanges within one of the following five groups: I. Small aliphatic, nonpolar or slightly polar residues: Ala, Ser, Thr, Pro, Gly II. Polar, positively charged residues: His, Arg, Lys III. Polar, negatively charged residues; and their amides: Asp, Asn, Glu, Gin IV. Large, aromatic residues: Phe, Tyr, Trp V. Large, aliphatic, nonpolar residues: Met, Leu, Ile, Val, Cys.

In the present description, the term "stringent conditions" refers to conditions that allow a polynucleotide or oligonucleotide to selectively, detectably and specifically bind with genomic DNA. Stringent conditions are defined by a suitable combination of salt concentration, organic solvent (such as formamide) concentration, temperature and other known conditions. Namely, stringency is increased by reducing salt concentration, increasing organic solvent concentration or raising hybridization temperature. Moreover, washing conditions following hybridization also have an effect on stringency. These washing conditions are also defined by salt concentration and temperature, and washing stringency increases as a result of reducing salt concentration and raising temperature. Thus, the term "stringent conditions" refers to conditions under which there is specific hybridization only between base sequences having a high degree of identity such that the degree of identity between each base sequence is, for example, about 80% or more on average overall, preferably about 90% or more, more preferably about 95% or more, even more preferably 97% or more, and most preferably 98% or more. Examples of "stringent conditions" include conditions such that sodium concentration is 150 mM to 900 mM and preferably 600 mM to 900 mM at a pH of 6 to 8 and temperature of 60° C. to 68° C. Specific examples include carrying out hybridization under conditions consisting of 5×SSC (750 mM NaCl, 75 mM trisodium citrate), 1% SDS, 5×Denhardt's solution, 50% formaldehyde and 42° C., and carrying out washing under conditions consisting of 0.1×SSC, (15 mM NaCl, 1.5 mM trisodium citrate), 0.1% SDS and 55° C.

"Hybridization" can be carried out in accordance with, for example, a method known in the art or a method in compliance therewith such as the method described in Current Protocols in Molecular Biology (edited by Frederick M. Ausubel et al.). In addition, in the case of using a commercially available library, hybridization can be carried out in accordance with the method described in the usage manual provided therewith. Genes selected by such hybridization may be naturally-occurring genes, such as plant-derived genes, or non-plant-derived genes. In addition, genes selected by hybridization may be cDNA, genomic DNA or chemically synthesized DNA.

The aforementioned phrase "amino acid sequence in which one or a plurality of amino acids have been deleted, substituted, inserted and/or added" refers to an amino acid sequence in which an arbitrary number of amino acids, such as 1 to 20, preferably 1 to 5 and more preferably 1 to 3, have been deleted, substituted, inserted and/or added. A type of genetic engineering technique in the form of site-specific mutagenesis is useful since it is a technique that enables a specific mutation to be introduced at a specific location, and can be carried out in compliance with the method described in Molecular Cloning: A Laboratory Manual, 2nd Ed., Cold Spring Harbor Laboratory Press, Cold Spring Harbor, N.Y., 1989. A protein composed of an amino acid sequence in which one or a plurality of amino acids have been deleted, substituted, inserted and/or added can be obtained by expressing this mutated DNA using a suitable expression system.

Nucleic acids and proteins having more than 50%, 60%, 70%, 75%, 80%, 85%, 90%, 95%, 96%, 97%, 98% or 99% "sequence identity" with the polynucleotides and proteins sequences disclosed herein, are also part of the present invention either alone or as part of any system (e.g. vectors and cells), cell, method and kit disclosed herein. Nucleic acids of the present invention may differ from any wild type sequence by at least one, two, three, four five, six, seven, eight, nine or more nucleotides.

The term "homology" between two sequences is determined by sequence identity. The term sequence identity refers to a measure of the identity of nucleotide sequences or amino acid sequences. In general, the sequences are aligned so that the highest order match is obtained. "Identity", per se, has recognized meaning in the art and can be calculated using published techniques. (See, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Grif fin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., SIAM J Applied Math 48:1073 (1988)).

Whether any particular nucleic acid molecule is at least 50%, 60%, 70%, 75%, 80%, 85%, 90%, 95%, 96%, 97%, 98% or 99% identical to, for instance, a certain nucleic acid sequence encoding MIP, or a part thereof, can be determined conventionally using known computer programs such as DNAs is software (Hitachi Software, San Bruno, Calif.) for initial sequence alignment followed by ESEE version 3.0 DNA/protein sequence software for multiple sequence alignments. Whether the amino acid sequence is at least 50%, 60%, 70%, 75%, 80%, 85%, 90%, 95%, 96%, 97%, 98% or 99% identical to, for instance a MIP in form of a protein, or a part thereof, can be determined conventionally using known computer programs such the BESTFIT pro gram (Wisconsin Sequence Analysis Package, Version 8 for Unix, Genetics Computer Group, University Research Park, 575 Science Drive, Madison, Wis. 5371 1). BESTFIT uses the local homology algorithm of Smith and Waterman, Advances in Applied Mathematics 2:482-489 (1981), to find the best segment of homology between two sequences. Many of the MIPs are well studied and have one, but often more than one conserved region. As the person skilled in the art will appreciate a variation in a nucleic acid/protein sequence is preferably, if not exclusively, outside such conserved region(s) of the respective MIP.

When using DNAs is, ESEE, BESTFIT or any other sequence alignment program to determine whether a particular sequence is, for instance, 95% identical to a reference sequence according to the present invention, the parameters are set such that the percentage of identity is calculated over the full length of the reference nucleic acid or amino acid sequence and that gaps in homology of up to 5% of the total number of nucleotides in the reference sequence are allowed.

IPTG refer to isopropyl-β-D-thiogalactopyranosid (IPTG) which is used as inducer for the T5 and Plac promoters in *E. coli.*

As used herein, "glycosyltransferase" (GT) refers to a polypeptide having an enzymatic capability of transferring glycosyl residues from an activated sugar donor to monomeric and polymeric acceptor molecules.

As used herein, "glycosylation" refers to the formation of a glycosidic linkage between a glycosyl residue and an acceptor molecule.

As used herein, "glucosylation" refers to the formation of a glycosidic linkage between a glucose residue and an acceptor molecule.

Glycosylation is the most common posttranslational modification (PTM) of proteins and it can occurs in several amino acid residues, but the most commonly modified residues are asparagine (N-glycosylation), threonine, and serine (O-glycosylation). In N-glycosylation, the glycan is attached to the amide nitrogen of Asn and in O-glycosylation, the glycosides are attached to the hydroxyl oxygen of the Ser or Thr residues.

As used herein, "flagellin" refers to a protein that is required to assemble the monopolar flagellum of a bacteria, preferably the monopolar flagellum of *Caulobacter crescentus*. Preferably the flagellin is an FljK, more preferably derived from *Caulobacter crescentus*, or a variant thereof.

As used herein, "flm operon" refers to an operon encoding for the proteins involved in the production of the soluble monosaccharide donor, preferably an operon encoding for proteins involved in the biosynthesis of pseudaminic acid. Preferably it refers to the enzymes involved in the pseudaminic acid biosynthesis pathway of *Caulobacter crescentus* and more preferably refers to the enzymes FlmA, FlmB, FlmH, FlmD, NeuB and FlmC.

One object of the invention is to provide a polynucleotide flmG, which encodes a Flagellin Modification Protein (FlmG) having a glycosyltransferase activity and being selected from the group consisting of the following (a) to (d):

a) a polynucleotide composed of SEQ ID NO: 26 or a polynucleotide encoding SEQ ID NO: 27;
b) a polynucleotide that hybridizes under stringent conditions with a polynucleotide sequence complementary to SEQ ID NO: 26 or with a polynucleotide sequence encoding SEQ ID NO: 27, and which encodes a protein having activity that transfers a soluble monosaccharide to the hydroxyl group on threonine residues of soluble acceptor proteins;
c) a polynucleotide that encodes a protein composed of an amino acid sequence in which one or a plurality of amino acids have been deleted, substituted, inserted and/or added in the amino acid sequence of SEQ ID NO: 27, and has activity that transfers a soluble monosaccharide to the hydroxyl group on threonine residues of soluble acceptor proteins; and,
d) a polynucleotide that encodes a protein that has an amino acid sequence having identity of 90% or more with the amino acid sequence of SEQ ID NO: 27 and has activity that transfers a soluble monosaccharide to the hydroxyl group on threonine residues of soluble acceptor proteins;

wherein glycosylation is a O-based glycosylation of said soluble acceptor proteins in the presence of said monosaccharide which is performed within the cytoplasm of bacterial Gram-negative cells.

Preferably, said bacterial Gram-negative cells are selected from the group comprising *Caulobacter crescentus, Sinorhizobium fredii* NGR234 or *Escherichia coli.*

According to an embodiment of the invention, the soluble monosaccharide to be transferred to the hydroxyl group on threonine residues of soluble acceptor proteins is selected from the group consisting of pseudaminic acid, sialic acid and legionamic acid.

Another object of the invention is to provide a recombinant expression vector for bacterial expression comprising the polynucleotide flmG of the invention and optionally a polynucleotide sequence encoding an flm operon, and/or a polynucleotide sequence encoding a flagellin protein, preferably an FLJK protein, optionally fused to a soluble acceptor protein of interest.

The flm operon is the operon encoding for the proteins involved in the production of the soluble monosaccharide donor. According to a preferred embodiment, the flm operon is a sequence selected from the group comprising or consisting of:

a) a polynucleotide sequence of SEQ ID NO: 19 or a polynucleotide that hybridizes under stringent conditions with a polynucleotide sequence complementary to SEQ ID NO: 19, and wherein said polynucleotide sequences encode the soluble monosaccharide donor from the flm biosynthetic operon;
b) a polynucleotide that encodes a protein composed of the amino acid sequence SEQ ID NO: 25; or a polynucleotide that encodes a protein composed of an amino acid sequence in which one or a plurality of amino acids have been deleted, substituted, inserted and/or added in the amino acid sequence of SEQ ID NO: 25, and has activity for production of the soluble monosaccharide donor in bacterial Gram-negative cells; and, c) a polynucleotide that encodes a protein that has an amino acid sequence having identity of 90% or more with the amino acid sequence of SEQ ID NO: 25 and has activity for production of the soluble monosaccharide donor in bacterial Gram-negative cells.

Preferably, the recombinant expression vector comprising the polynucleotide flmG and the flm operon has the sequence SEQ ID NO: 29.

In a preferred embodiment, the polynucleotide sequence encoding a flagellin protein is a) a polynucleotide sequence of SEQ ID NO: 4, SEQ ID NO: 5, SEQ ID NO: 30 or SEQ ID NO: 32 or a polynucleotide that hybridizes under stringent conditions with a polynucleotide sequence complementary to SEQ ID NO: 3, SEQ ID NO: 24, SEQ ID NO: 31 or SEQ ID NO: 33, and wherein said polynucleotide sequences encode a flagellin protein;

b) a polynucleotide that encodes a protein composed of the amino acid sequence SEQ ID NO: 3, SEQ ID NO: 24, SEQ ID NO: 31 or SEQ ID NO: 33; or a polynucleotide that encodes a protein composed of an amino acid sequence in which one or a plurality of amino acids have been deleted, substituted, inserted and/or added in the amino acid sequence of SEQ ID NO: 3, SEQ ID NO: 24, SEQ ID NO: 31 or SEQ ID NO: 33, and has activity as a flagellin; and, c) a polynucleotide that encodes a protein that has an amino acid sequence having identity of 90% or more with the amino acid sequence of SEQ ID NO: 3, SEQ ID NO: 24, SEQ ID NO: 31 or SEQ ID NO: 33 and has activity as a flagellin.

In a preferred embodiment, the flagellin protein is of SEQ ID NO: 4, SEQ ID NO: 5, SEQ ID NO: 30 or SEQ ID NO: 32, preferably SEQ ID NO: 4 or SEQ ID NO: 5, or a polynucleotide that encodes a protein composed of an amino acid sequence of SEQ ID NO: 3, SEQ ID NO: 24, SEQ ID NO: 31 or SEQ ID NO: 33, preferably SEQ ID NO: 3 or SEQ ID NO: 24, wherein said polynucleotide sequences encode a flagellin FLJK protein or a biological active fragment thereof or a FLJK protein composed of an amino acid sequence in which one or a plurality of amino acids have been deleted, substituted, inserted and/or added in the amino acid sequence of SEQ ID NO: 3, SEQ ID NO: 24, SEQ ID NO: 31 or SEQ ID NO: 33.

Preferably, said flagellin protein as defined above, is the acceptor of FlmG-dependent glycosylation on threonine residues of said flagellin protein or biological active fragment thereof.

Preferably, the recombinant expression vector comprising the nucleic acid of the invention and a polynucleotide sequence encoding a flagellin protein has the polynucleotide sequence of SEQ ID NO: 21.

According to a preferred embodiment, the recombinant expression vector of the invention, wherein said polynucleotide sequences encoding a flagellin protein is an FLJK protein, preferably derived from *Caulobacter crescentus*, or a biological active fragment thereof is fused to a polynucleotide sequence encoding a soluble acceptor protein of interest.

For example, the soluble acceptor protein of interest is selected from the group comprising Alpha-1-Antitrypsin, Interferon-beta, insulin, or antimicrobial peptides such as cecropin B, attacin, diptericin, drosocin.

Advantageously, the soluble acceptor protein of interest further comprises an amino acid sequence of a short hexahistidine or Flag tag epitope genetically appended on the N-terminus of said soluble acceptor protein of interest. In doing so, the soluble acceptor protein also defined simply as the acceptor can easily be collected from the cytoplasm of the bacterial Gram-negative host or cell with affinity purification using this short epitope (hexahistidine or Flag tag) genetically appended on the N-terminus of the acceptor.

The person skilled in the art will understand that the recombinant expression vector of the invention is inducible by the addition of Isopropyl-β-D-thiogalactopyranoside (IPTG).

Another object of the invention is to provide a transformed prokaryotic host cell transformed with at least one copy of the recombinant expression vector of the invention as described above.

Another object of the invention is to provide prokaryotic protein glycosylation kit for soluble O-based glycosylation comprising a bacterial Gram-negative host that produces a soluble monosaccharide donor, and expresses a Flagellin Modification Protein (FlmG), wherein such Gram-negative host expresses at least one copy of a recombinant expression vector comprising a polynucleotide sequence encoding a soluble acceptor protein of interest.

The host can naturally produce the soluble monosaccharide donor and express the Flagellin Modification Protein (FlmG) or alternatively it can be an engineered host, which produces the soluble monosaccharide donor and/or expresses the Flagellin Modification Protein (FlmG) recombinantly.

Thus, in one embodiment, the host naturally produces the soluble monosaccharide donor and expresses the Flagellin Modification Protein (FlmG). This is for example the case of *Caulobacter crescentus*, which is a suitable host for the prokaryotic glycosylation kit of the invention. Even though *Caulobacter crescentus* already expresses a Flagellin Modification Protein (FlmG), it can be advantageous to further transform this host with an expression vector comprising a polynucleotide sequence encoding a variant of such FlmG. Indeed, such variants can have a slightly different activity, and may exhibit different specificity for particular soluble monosaccharide donors and/or acceptor proteins. Thus, depending on the donor and acceptor involved it can be useful to express more than one variant of FlmG. This is in particular the case when more than one acceptor protein of interest is expressed and intended to be glycosylated. Therefore, in a particular embodiment of the invention, *Caulobacter crescentus* further comprises at least one copy of an expression vector of the invention, as defined above, comprising the synthetic FlmG chimera.

In an alternative embodiment, the host naturally produces the soluble monosaccharide donor and is transformed to recombinantly express the Flagellin Modification Protein (FlmG). This is for example the case of *Sinorhizobium fredii* NGR234, a *Sinorhizobium fredii* HH103 or a *Shewanella oneidensis* MR-1. These organism express an flm operon and therefore naturally produce the soluble monosaccharide donor pseudaminic acid.

Such hosts that naturally produce the soluble monosaccharide donor are transformed with at least one copy of an expression vector comprising a polynucleotide flmG which encodes a Flagellin Modification Protein (FlmG) having a glycosyltransferase activity, preferably selected from the group consisting of the following (a) to (d):

a) a polynucleotide composed of SEQ ID NO: 2, SEQ ID NO: 26 or a polynucleotide encoding SEQ ID NO: 1, SEQ ID NO: 23 or SEQ ID NO: 27;

b) a polynucleotide that hybridizes under stringent conditions with a polynucleotide sequence complementary to SEQ ID NO: 2 or SEQ ID NO: 26 or with a polynucleotide sequence encoding SEQ ID NO: 1, SEQ ID NO: 23 or SEQ ID NO: 27, and which encode a protein having activity that transfers a soluble monosaccharide to the hydroxyl group on threonine residues of soluble acceptor proteins;

c) a polynucleotide that encodes a protein composed of an amino acid sequence in which one or a plurality of amino acids have been deleted, substituted, inserted and/or added in the amino acid sequence of SEQ ID NO: 1, SEQ ID NO: 23 or SEQ ID NO: 27, and has activity that transfers a soluble monosaccharide to the hydroxyl group on threonine residues of soluble acceptor proteins; and, d) a polynucleotide that encodes a protein that has an amino acid sequence having identity of 90% or more with the amino acid sequence of SEQ ID NO: 1, SEQ ID NO: 23 or SEQ ID NO: 27 and has activity that transfers a soluble monosaccharide to the hydroxyl group on threonine residues of soluble acceptor proteins;

wherein glycosylation is a O-based glycosylation of said soluble acceptor proteins in the presence of said monosaccharide which is performed within the cytoplasm of bacterial Gram-negative cells.

Other suitable hosts are those that neither naturally produce the soluble monosaccharide donor, nor express the FlmG protein. Such hosts a perfectly suitable for use in the prokaryotic glycosylation kit of the invention, provided that they are transformed to recombinantly produce the soluble monosaccharide donor and express the FlmG protein. The use of such hosts is particularly advantageous when such hosts are easily grown and suitable for industrial use, such as *Escherichia coli.*

Such hosts comprise:

(1) at least one copy of an expression vector comprising a polynucleotide flmG which encodes Flagellin Modification Protein (FlmG) having a glycosyltransferase activity, preferably selected from the group consisting of the following (a) to (d):

a) a polynucleotide composed of SEQ ID NO: 2, SEQ ID NO: 26 or a polynucleotide encoding SEQ ID NO: 1, SEQ ID NO: 23 or SEQ ID NO: 27;

b) a polynucleotide that hybridizes under stringent conditions with a polynucleotide sequence complementary to SEQ ID NO: 2 or SEQ ID NO: 26 or with a polynucleotide sequence encoding SEQ ID NO: 1, SEQ ID NO: 23 or SEQ ID NO: 27, and which encode a protein having activity that transfers a soluble monosaccharide to the hydroxyl group on threonine residues of soluble acceptor proteins;

c) a polynucleotide that encodes a protein composed of an amino acid sequence in which one or a plurality of amino acids have been deleted, substituted, inserted and/or added in the amino acid sequence of SEQ ID NO: 1, SEQ ID NO: 23 or SEQ ID NO: 27, and has activity that transfers a soluble monosaccharide to the hydroxyl group on threonine residues of soluble acceptor proteins; and, d) a polynucleotide that encodes a protein that has an amino acid sequence having identity of 90% or more with the amino acid sequence of SEQ ID NO: 1, SEQ ID NO: 23 or SEQ ID NO: 27 and has activity that transfers a soluble monosaccharide to the hydroxyl group on threonine residues of soluble acceptor proteins;

wherein glycosylation is a O-based glycosylation of said soluble acceptor proteins in the presence of said monosaccharide which is performed within the cytoplasm of bacterial Gram-negative cells;

(2) at least one copy of a recombinant expression vector comprising a sequence encoding an flm operon, preferably selected from the group consisting of:

a) a polynucleotide sequence of SEQ ID NO: 19 or a polynucleotide that hybridizes under stringent conditions with a polynucleotide sequence complementary to SEQ ID NO: 19, and wherein said polynucleotide sequences encode the soluble monosaccharide donor flm biosynthetic operon;

b) a polynucleotide that encodes a protein composed of the amino acid sequence SEQ ID NO: 25; or a polynucleotide that encodes a protein composed of an amino acid sequence in which one or a plurality of amino acids have been deleted, substituted, inserted and/or added in the amino acid sequence of SEQ ID NO: 25, and has activity for production of the soluble monosaccharide donor in bacterial Gram-negative cells; and c) a polynucleotide that encodes a protein that has an amino acid sequence having identity of 90% or more with the amino acid sequence of SEQ ID NO: 25 and has activity for production of the soluble monosaccharide donor in bacterial Gram-negative cells.

In a preferred embodiment, the soluble monosaccharide donor is selected from the group consisting of pseudaminic acid, sialic acid and legionamic acid.

In preferred embodiments, the soluble acceptor protein is selected from a) a flagellin;

b) a protein selected from the group consisting of Alpha-1-Antitrypsin, Interferon-beta, insulin and antimicrobial peptides such as cecropin B, attacin, diptericin or drosocin; and c) a flagellin fused to another soluble protein of interest, preferably fused to a protein selected from the group consisting of Alpha-1-Antitrypsin, Interferon-beta, insulin and antimicrobial peptides such as cecropin B, attacin, diptericin or drosocin.

A still further object of the invention is to provide a prokaryotic protein glycosylation kit for soluble O-based glycosylation comprising a bacterial Gram-negative host expressing at least one copy of a recombinant expression vector comprising the polynucleotide sequence flmG derived from *Caulobacter crescentus* as defined above. Preferably, the kit further comprises at least one copy of a recombinant expression vector comprising a polynucleotide sequence encoding the soluble monosaccharide donor flm biosynthetic operon as described above.

According to another embodiment, the kit further comprises at least one copy of a recombinant expression vector comprising a polynucleotide sequence encoding a flagellin FLJK protein derived from *Caulobacter crescentus* as described above.

Preferably, said polynucleotide sequence encoding a flagellin FLJK protein derived from *Caulobacter crescentus* is fused to a polynucleotide sequence encoding a soluble acceptor protein of interest, said soluble acceptor protein of interest optionally comprises an amino acid sequence of a short hexahistidine or Flag tag epitope genetically appended on the N-terminus of said soluble acceptor protein of interest.

Preferably, the bacterial Gram-negative host is selected from the group comprising *Caulobacter crescentus, Sinorhizobium fredii* NGR234 or *Escherichia coli.*

In a further embodiment, the invention provides a process for O-glycosylation of a soluble acceptor protein, comprising:

a) transforming a bacterial Gram-negative host that produces a soluble monosaccharide donor, such as pseudaminic acid, sialic acid and legionamic acid, and expresses a Flagellin Modification Protein (FlmG) with at least one copy of a recombinant expression vector comprising a polynucleotide sequence encoding a soluble acceptor protein of interest;

b) growing the Gram-negative host under conditions suitable to the expression of the soluble acceptor protein of interest; and c) isolating the glycosylated soluble protein of interest from the host.

The Gram-negative host that produces a soluble monosaccharide donor and expresses flagellin modification protein FlmG is preferably as defined in any of the above-described embodiments of the prokaryotic glycosylation kit.

Understanding how specificity is programmed into post-translational modification of proteins is of major importance in biology and still poorly understood for bacterial protein glycosylation systems, especially for soluble O-glycosylation systems operating in the bacterial cytoplasm.

In example 1, Applicants dissected and reconstituted the O-glycosylation pathway that modifies all six paralogous flagellins, five structural and one regulatory flagellin, that are required to assemble the monopolar flagellum of the alpha-proteobacterium *Caulobacter crescentus* (FIG. 1), Applicants identified the biosynthetic pathway (FIG. 2) for the sialic acid-like sugar pseudaminic acid (FIG. 3) and demonstrated its requirement for motility, flagellation and flagellin modification (see FIGS. 4 and 6). The cognate NeuB enzyme that condenses phosphoenolpyruvate with a hexose into pseudaminic acid, rather than sialic acid (FIG. 2), is functionally interchangeable with other pseudaminic acid synthases. Using *Sinorhizobium fredii* NGR234, a bacterium producing a pseudaminic acid-based K-antigen capsule, as heterologous host, Applicants surprisingly found that the uncharacterized FlmG protein of *C. crescentus* is the glycosyltransferase required and sufficient for flagellin modification when expressed from plasmid 1 pSRK-Gm-fljK(syn)-flmG (FIGS. 5 and 6) introduced into *Sinorhizobium fredii* NGR234. Importantly, glycosylation specificity is conferred by a direct interaction of FlmG with FljK mediated via the N terminal domain, while the C-terminal domain in FlmG uses the pseudaminic acid donor molecule to modify the Fljk acceptor.

In example 2, Applicants first transformed *E. coli* to ampicillin resistance with a plasmid 2, pUCIDT-flm_operon_syn (FIG. 5), expressing six biosynthesis pathway enzymes for the sugar pseudaminic acid from synthetic genes. Then, the resulting *E. coli* cells were transformed to gentamycin resistance with plasmid 2 pSRK-Gm-fljK(syn)-flmG (FIG. 5). The resulting *E. coli* cells were grown in the presence of ampicillin and gentamycin, and expression of the genes on the plasmid was induced by the addition of 1 mM IPTG. When immunoblots were performed with antibodies to FljK the typical migration change (decrease) was observed, but only in the presence of plasmid 2, that is indicative of glycosylated FljK (FIG. 6)

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practising the present invention and are not intended to limit the scope of the invention.

EXAMPLES

Material and Methods:

Strains and Growth Conditions

*Caulobacter crescentus* NA1000 and derivatives were grown at 30° C. in PYE (peptone-yeast extract) or M2G (minimal glucose). *Sinorhizobium fredii* NGR234 was grown at 30° C. in TY (tryptone-yeast extract). *Escherichia coli* EC100D were grown at 30° C. in LB. Antibiotics were used at the following concentrations gentamicin 1 μg/mL for *C. crescentus* and 20 μg/mL for *E. coli* and *S. fredii*, ampicillin 100 μg/mL for *E. coli* and *S. fredii*. Plasmids were introduced into *S. fredii* by bi-parental mating and into *C. crescentus* by electroporation.

Immunoblots

For immunoblots, protein samples were separated on SDS polyacrylamide gel, transferred to polyvinylidene difluoride (PVDF) Immobilon-P membranes (Merck Millipore) and blocked in TBS (Tris-buffered saline) 0.1% Tween20 and 5% dry milk. The anti-sera were used at the following dilutions: anti-NeuB (1:10'000), anti-FlmG (1:10'000), anti-FljK (1:10'000). Protein-primary antibody complexes were visualized using horseradish peroxidase-labelled anti-rabbit antibodies and ECL detection reagents (Merck Millipore).

Example 1

Flagellin glycosylation occurs at serine or threonine resides by O-linking glycosyl-transferases (henceforth OGTs). Glycosylation usually occurs at the two surface-exposed central domains of flagellin and is therefore ideally positioned to influence the immunogenicity of the filament and the virulence in pathogens. Since no consensus sequence determinant in the primary structure of flagellin acceptor (apart from the serine or threonine modification site) has been identified, OGTs likely recognize the tertiary structure of the glycosyl acceptor in a highly specific manner, as shown here via specific of the acceptor through an N-terminal recognition domain on the OGT polypeptide. Glycosylation precedes secretion of the flagellin via the flagellar export machinery (FIG. 4) to the tip of the growing flagellar filament, indicating that flagellin glycosylation by the OGT must occur in the cytoplasm.

During flagellar assembly in Gram-negative (diderm) bacteria, the basal body harbouring the export apparatus is assembled first in the cytoplasmic membrane, followed by envelope-spanning structures along with the external hook structure that serves as universal joint between the flagellar filament and the envelope-spanning parts. The flagellins are assembled last by polymerization on the hook into the flagellar filament (FIG. 4) and they are usually the last proteins to be expressed during assembly.

Here Applicants establish, dissect and reconstitute the O-linked flagellin glycosylation pathway of *C. crescentus* that expresses six flagellin paralogs: five (FljKLMNO) are sufficient for flagellar filament formation and motility[11], while the regulatory flagellin FljJ controls translation of the others. Applicants show that all six flagellins in *C. crescentus* are glycosylated in a manner that requires pseudaminic acid and the OGT FlmG. Reconstitution in a heterologous system, *Sinorhizobium fredii* NGR234, reveals that FlmG is sufficient for flagellin glycosylation and that the underling specificity of glycosylation resides in the modular organization of FlmG: an N-terminal substrate (flagellin) binding domain and a C-terminal glycosyltransferase domain. Applicants demonstrated that both domains are required for flagellin glycosylation, formation of the flagellar filament and motility, but not for flagellin export. Finally, Applicants studies reveal how flagellin glycosylation is tuned with the progression of the *C. crescentus* cell cycle.

Results

NeuB is required for flagellar filament assembly.

A previously assembled library of *C. crescentus* transposon (Tn) motility mutants included four mutants each harbouring a Tn insertion in the uncharacterized gene, CCNA_02961, predicted to encode a NeuB-like sialic acid synthase (henceforth neuB). Three Tn mutants harbour a himar1 insertion (NS7, NS44 and NS388) at different locations in neuB, while in the other (NS150) neuB is disrupted by an Ez-Tn5 insertion. All four mutants are non-motile on soft (0.3%) agar plates and do not swim when observed by phase contrast light microscopy. An in-frame deletion of neuB (ΔneuB) recapitulated the motility defect of the Tn insertions. Expression of NeuB from a plasmid/vector (pMT335 [12]) corrected the motility defect of in ΔneuB cells, indicating that neuB function is required for motility (FIG. 1C). Transmission electron microscopy (TEM) reveals a flagellar filament on the new pole of WT cells, whereas ΔneuB cells lack a flagellar filament and only harbour a short protrusion corresponding to a hook structure (FIG. 1D). The neuB gene is predicted to encode a 38-kDa protein belonging to the NeuB-family of acetylneuraminate synthases, suggesting that biosynthesis of sugars of the sialic acid family is required for flagellation in *C. crescentus.*

To gain further insights into the flagellar assembly defect of ΔneuB cells, Applicants investigated whether flagellins are synthesized and exported in the absence of NeuB by immunoblotting using antibodies to the FljK flagellin (that also cross-react with other flagellins, see below, FIG. 6).

NeuB family members are phosphoenolpyruvate (PEP)-dependent synthases that catalyse the condensation of PEP with hexoses to form sialic acid or pseudaminic acid, sometimes in the same species, for example in *C. jejuni* encoding the sialic acid synthase NeuB1 and the pseudaminic acid synthase NeuB3[13]. Applicants sought to clarify whether *C. crescentus* NeuB is a sialic acid or a pseudaminic acid synthase. To resolve this question, conducted heterologous complementation with the three NeuB variants from *C. jejuni* whose enzymatic activities are known: NeuB1 synthesize sialic acid, NeuB2 produces legionaminic acid and NeuB3 is pseudaminic acid synthase[13]. Using motility and flagellin modification as a read-out for NeuB activity, Applicants discovered that only NeuB3 can substitute for *C. crescentus* NeuB, indicating that it functions as a pseudaminic acid synthase.

Since *C. jejuni* NeuB3 also functions in the control of motility, Applicants sought to corroborate their conclusion with a pseudaminic acid synthase that does not act in the flagellation pathway and test whether this enzyme can also support flagellation in *C. crescentus* ΔneuB cells. Conversely, if *C. crescentus* NeuB is indeed a pseudaminic acid synthase, then it should be able to support another pseudaminic acid-dependent function. Applicants therefore turned to the symbiotic alpha-proteobacterium *Sinorhizobium fredii* NGR234 that synthetizes as K-antigen capsule, a polymer composed of pseudaminic and glucuronic acid units[9]. *S. fredii* NeuB (called RkpQ) is encoded in the K-antigen capsular polysaccharide biosynthesis (rpk3) locus rkp3 on the pNGR234b megaplasmid. As observed for NeuB3 from *C. jejuni*, RkpQ was able to functionally replace NeuB in *C. crescentus*, restoring motility and flagellin migration to *C. crescentus* ΔneuB cells. To confirm that *C. crescentus* NeuB is indeed a pseudaminic acid synthase, Applicants constructed an rkpQ deletion mutant (ΔrkpQ) in *S. fredii* and observed that this mutation blocks synthesis of the K-antigen capsule 14. Capsule synthesis was restored by complementation of *S. fredii* ΔrkpQ cells with a plasmid expressing either RkpQ, *C. crescentus* NeuB or *C. jejuni* NeuB3. By contrast, *C. jejuni* NeuB1 and NeuB2 could not restore capsular polysaccharide production. Thus, pseudaminic synthesis is required for motility and flagellin modification in *C. crescentus* and its biosynthesis proteins function interchangeably with K-antigen production in *S. fredii* NGR234 and *C. crescentus* motility.

The OGT FlmG is required and sufficient for flagellin modification.

Knowing that pseudaminic acid synthesis is required for motility and modification of all six flagellins in *C. crescentus*, Applicants predicted that their Tn library of motility mutants should also contain Tn insertions in a gene encoding a cognate OGT. Inspection of the Tn insertion sites, revealed ten mutants with a Tn insertion in the CCNA_01524 (henceforth flmG) gene: six bear a himar1 Tn insertion at different positions in flmG (strains NS25, NS55, NS81, NS128, NS157 and NS192), while an Ez-Tn5 insertion disrupts flmG (NS149, NS211, NS322 and NS327). The flmG gene is predicted to encoded a 596-residue protein of 65 kDa containing an N-terminal domain (NTD) with tetratricopeptide (TPR) repeats, known to be involved in protein-protein interactions, and a C-terminal domain (CTD) resembling glycosyltransferases (GT-B superfamily). Applicants constructed an in-frame deletion in flmG (ΔflmG) and found the resulting mutant cells have a defect in motility (FIG. 4A) and flagellin modification (FIG. 4B) and found that the defect was corrected upon expression of FlmG in trans from $P_{van}$ on pMT335 (FIG. 4A). Thus, FlmG acts in the same pathway as NeuB as predicted for an OGT responsible for the post-translational O-glycosylation of flagellins in *C. crescentus.*

Furthermore, the activity of the variant FlmG having the sequence SEQ ID NO: 27 was assessed by immunoblotting. The mutant cells in which the in-frame deletion in flmG (ΔflmG) was present was transformed with the synthetic flmG having the nucleotide sequence SEQ ID NO: 26 and performed an immunoblot assay (FIG. 7). It can be observed that in the wild-type *Caulobacter crescentus* FljK is glycosylated (A), whereas in the ΔflmG *Caulobacter crescentus*, FljK is not glycosylated (B), as demonstrated by the difference in migration. When the ΔflmG *Caulobacter crescentus* is transformed with a plasmid bearing the synthetic FlmG having the nucleic acid sequence SEQ ID NO: 26 (D), FljK is again glycosylated as shown by its migration close to that of the FljK produced in the wild-type *Caulobacter crescentus* (A).

To prove that FlmG is indeed the OGT in this modification pathway, Applicants probed for sufficiency of flagellin modification by expression of FlmG in a heterologous system producing pseudaminic acid. Applicants therefore chose to (co-)express FljK with or without FlmG in *S. fredii* NGR234 and probed for flagellin modification by immunoblotting using antibodies to *C. crescentus* FljK (FIG. 4C). In the absence of FlmG, FljK showed the same mobility on SDS-PAGE as in *C. crescentus* ΔneuB cells. However, upon co-expression of FlmG, FljK shifted to a species with higher molecular mass and identical apparent migration on SDS-PAGE to that observed FljK in *C. crescentus* WT cells. Importantly, this shift was dependent on the presence of pseudaminic acid, since FljK co-expressed with FlmG in *S. fredii* cells lacking pseudaminic acid (ΔrkpQ or Δrkp3_013, see below) had the same mobility by SDS-PAGE as FljK expressed in *C. crescentus* ΔneuB or ΔflmG cells or in WT *S. fredii* cells without FlmG (FIG. 4C). Applicants concluded that FlmG is required and sufficient for flagellin modification in the presence of pseudaminic acid.

A major question in glycosylation is how substrate specificity is programmed into the OGTs of the system. Based on the domain organization of FlmG, Applicants reasoned that the NTD might hold the specificity determinant towards the flagellins, perhaps by directly interacting with flagellins. By contrast, the CTD might confer OGT activity, but would not function without the NTD specificity determinant. Indeed, expression of the CTD alone did nor restore motility or flagellin modification to *C. crescentus* ΔflmG cells (FIG. 4D). Applicants next probed for a direct interaction of NTD with flagellins using the bacterial two-hybrid assay (BACTH, FIG. 4E). This assay is based on the functional reconstitution of the adenylate cyclase from *Bordetella pertussis*, composed of two fragments, T25 and T18[15]. When the two proteins of interest fused to each fragment interact, adenylate cyclase is reconstituted and produces cyclic AMP, which in turn induces the expression of the lacZ gene. Applicants tested combinations of the FlmG NTD and CTD together with the flagellins FljJ, FljK and FljM as probes. Notably, a strong interaction was observed between each of the flagellins and the FlmG NTD, but not FlmG CTD (FIG. 4E). These BACTH results along with the domain analysis show the TPR-containing NTD is required for FlmG and sufficient for a specific interaction with multiple flagellins performing structural or regulatory functions, consistent with Applicants' finding that all flagellins are modified with pseudaminic acid by FlmG.

Applicants sought to identify the other enzymatic components in pseudaminic acid biosynthesis using a combination of genetics and bioinformatics. The first two enzymes of the pathway elucidated in *C. jejuni* are PseB (UDP-N-acetylglucosamine 4,6-dehydratase) and PseC (UDP-4-amino-4,6-dideoxy-N-acetyl-beta-L-altrosamine transaminase). Since genes that act in the same *C. crescentus* should be required for motility, Applicants scanned their library of Tn mutants for insertions in orthologous genes. Indeed, the gene products of flmA (CCNA_00233) and flmB (CCNA_00234) resemble PseB and PseC, respectively. This search mutants with Tn insertions in flmA (NS235, NS246 and NS294 had HyperMu insertions, NS148 harboured an Ez-Tn5 insertion and NS102 a Tn5 insertion) and three mutants with Tn insertions in flmB (Himar1 insertion in NS76 and Hyper Mu insertions in NS132 and NS255). Importantly, these mutants recapitulate the motility and flagellin modification defect of neuB and flmG mutant cells (FIGS. 5B-5E) and the corresponding orthologs of *S. fredii*, RkpL and RkpM, can functionally replace *C. crescentus* FlmA and FlmB (FIG. 5B, 50, 5E).

For the third step of the pathway, Applicants found that at least a fourfold enzymatic redundancy or promiscuity exists in *C. crescentus* as inactivation of the predicted ortholog (flmH, CCNA_01523), as well as paralogous genes CCNA_01531 and CCNA_01537, i.e. a ΔflmH ΔCCNA_01531 ACCNA_01537 triple mutant, did not phenocopy the effects of neuB, flmA, flmB or flmG disruption. Conversely, however, Applicants demonstrated that inactivation of the flmH ortholog in *S. fredii*, rkp3_013, led to a defect in K-antigen capsule synthesis which could be restored by expression of *C. crescentus* flmH in trans (FIG. 3E). Thus, FlmH can execute the corresponding acetylating step in pseuedaminic acid synthesis, at least in *S. fredii*.

Bioinformatics predicts that the fourth step in pseudaminic acid biosynthesis is executed by FlmD (CCNA_02947) in *C. crescentus* and RkpO in *S. fredii* NGR234. To verify this prediction, Applicants engineered and in-frame deletion in flmD (AflmD) and found that the resulting cells are non-motile consistent with a previous report[11] and unable to modify flagellins (FIG. 5F, 5G). Importantly, Applicants found that *S. fredii* RkpO can functionally replace FlmD, restoring motility and flagellin modification to *C. crescentus* AflmD cells (FIG. 5F). Thus, the FlmD enzyme is also required pseudaminic acid synthesis. Immediately downstream of and co-encoded with flmD lies flmC whose gene product ensembles cytidylyltransferases. Since the pseudaminic acid must usually be activated with cytidine 5'-monophosphate (CMP) before being incorporated into a polysaccharide or protein 13, FlmC likely executes this last event In *C. crescentus*.

Discussion

The molecular basis underlying the specificity of bacterial protein glycosylation systems, especially those operating in the cytoplasm is poorly understood. These cytoplasmic systems can be engineered into custom-designed protein modification technologies for a particular protein of interest Post-translational modification and specificity of FlmG Rewiring FlmG-dependent glycosylation.

*C. crescentus* Flagellins are Glycosylated by a Dedicated OGT

There are two different mechanisms for the transfer of the sugar moiety onto the acceptor protein. The oligosaccharide can be synthesized on a lipid carrier and then transferred on the acceptor protein by an oligosaccharyl-transferase (OTase)-dependent mechanism,[5]. Glycosylation of flagellin subunits are unusual and potentially more versatile as it occurs by an OTase-independent mechanism in which monosaccharidic units are sequentially transferred on the acceptor protein by a glycosyltransferase. Glycosyltransferases responsible for flagellin modification are usually not conserved at the sequence level and are probably specific for the flagellin and soluble monosaccharide(s) used by a given species. Applicants identified FlmG, which has an N-terminal TPR repeat domain, required for the interaction for the flagellin substrate, and a C-terminal enzymatic glycosyltransferase domain. Some genes encoded in flagellin modification loci of *Campylobacter, Helicobacter* and *Aeromo-*

*nas* (called Maf for motility associated factor) have been proposed to play a role in transferring the sugars on the flagellin protein [7,8]. In particular *A. caviae* SchN3 encodes only one maf gene, maf1, whose mutation has been shown to affect polar flagellin glycosylation but not lateral flagellin or LPS biosynthesis, suggesting that Maf1 is a glycosyltransferase specific for *A. caviae* polar flagellin.

Based on phenotype and BACTH assay, FlmG is able to glycosylate all flagellins encoded by *C. crescentus*. FlmG is conserved only in *Caulobacter* species and close alpha-proteobacteria.

The Role of Flagellin Glycosylation

The presence of carbohydrates related to sialic acid on the surface of pathogenic strains is often considered as a way to evade the host immune system. However, as flagellin glycosylation appears to be common also in environmental strains, there must be other reasons for this post-translational modification.

In *C. crescentus*, the lack of glycosylation also determines the absence of the flagellar filament, although flagellin can be detected in the culture supernatant of ΔneuB or ΔflmG mutants. These data support the hypothesis that glycosylation plays a structural role in filament polymerization rather than representing a signal for flagellin secretion, in agreement with what observed in *A. caviae* Sch3N, where in a maf1 (glycosyltransferase) mutant flagellin is also still exported, but not it *Magnetospirillum magneticum* AMB-1 maf mutants[7,8]. However, flagellins seem actually to be less efficiently exported when unglycosylated (in ΔneuB or ΔflmG cells), suggesting that the interaction with the secretion chaperone is less efficient or the solubility is reduced in the absence of glycosylation, Example 2

To confirm that these six enzymatic steps are necessary and sufficient for pseudaminic acid synthesis, Applicants reconstituted FlmG-dependent glycosylation in *E. coli* K12 cells using a plasmid with a synthetic flm operon expressing all six enzymes (FlmA-FlmB-FlmH-FlmD-NeuB-FlmC) from open reading frames that had been codon-optimized for expression in *E. coli* (plasmid 2, pUCIDT-flm_operon_syn, FIGS. 5 and 6). Applicants also introduced a second, compatible plasmid co-expressing FljK and FlmG (plasmid 1, pSRK-Gm-fljK(syn)-flmG into these cells and then probed for FljK by immunoblotting using antibodies to FljK and the production of donor, acceptor and transferase was induced with IPTG. Upon addition of IPTG the acceptor is expressed and glycosylated. (FIGS. 5 and 6). Fig. shows an immunoblot with anti-FljK antibodies on whole cell lysates from *E. coli* expressing fljK and flmG from Plac on plasmid 1, in presence or absence of the plasmid carrying the complete set of *Caulobacter* genes for the pseudaminic acid biosynthetic pathway (pUCIDT-flm_operon_syn, plasmid 2). In the absence of pUCIDT-flm, FljK shows the same migration profile as in *Caulobacter crescentus* ΔneuB cells, whereas in the presence of pUCITD-flm FljK migration is shifted towards higher molecular weight, as in *Caulobacter crescentus* wild-type (WT) cells. The values above the panel indicate the concentration of the inducer for Plac-fljK-flmG on plasmid 1 (mM IPTG). The blue line indicates the migration of the molecular size standard, with the corresponding size in kDa. This immunblot was done by blotting cell extracts that had been separated 12.5% SDS-PAGE on a PVDF immobilin membrane. The cell extracts were from *E. coli* cells grown in LB as described and induced for 2 hours with IPTG.

Sequence Listing Free Text

SEQ ID NO: 1 corresponds to FlmG (aka FlbA, CC_1457): glycosylates flagellin using CMP-linked pseudaminic acid as donor (CMP-Pse), from *Caulobacter crescentus* (Accession number ACL94989, www.ncbi.nlm-.nih.gov/protein/ACL94989.1) SEQ ID NO: 2 corresponds to flmG Nucleotide sequence *Caulobacter crescentus* (natural)

SEQ ID NO: 3 corresponds to Fljk, CC_1461, the Flagellin protein, from *Caulobacter crescentus* (Accession: ACL94993, www.ncbi.nlm.nih.gov/protein/220963637). FIJK is the acceptor of FlmG-dependent glycosylation on T143, T158, T163, T196.

SEQ ID NO: 4 corresponds to fljK nucleotide (natural) from *Caulobacter crescentus.*

SEQ ID NO: 5 corresponds to a synthetic fljK nucleotide sequence.

SEQ ID NO: 6 corresponds to a synthetic linker with the *E. coli* phage T5 promoter.

SEQ ID NO: 7 corresponds to flmA_synthetic nucleotide sequence.

SEQ ID NO: 8 corresponds to FlmA protein sequence (CCNA_00233, accession ACL93700).

SEQ ID NO: 9 corresponds to flmB_synthetic nucleotide sequence.

SEQ ID NO: 10 corresponds to FlmB protein sequence (CCNA_00234, accession ACL93701).

SEQ ID NO: 11 corresponds to flmH_synthetic nucleotide sequence.

SEQ ID NO: 12 corresponds to FlmH protein sequence (CCNA_01523, accession ACL94988).

SEQ ID NO: 13 corresponds to flmD_synthetic nucleotide sequence.

SEQ ID NO: 14 corresponds to FlmD protein sequence (CCNA_02947, accession ACL96412).

SEQ ID NO: 15 corresponds to neuB synthetic nucleotide sequence.

SEQ ID NO: 16 corresponds to NeuB protein sequence (CCNA_02961, accession ACL96426).

SEQ ID NO: 17 corresponds to flmC synthetic nucleotide sequence.

SEQ ID NO: 18 corresponds to FlmC protein sequence (CCNA_02946, accession ACL96411).

SEQ ID NO: 19 corresponds to an artificial operon of codon optimized genes encoding 6 enzymes for synthesis of pseudaminic acid (the soluble monosaccharide donor). The operon consists of flmA-flmB-flmH-flmD-neuB-flmC synthetic coding sequences. The filmA, flmB, flmD and neuB (and flmG) gene were discovered in *Caulobacter crescentus* as reported herein and their functions was assigned because of the mutant defect (glycosylation defect, inability to glycosylate FljK).

SEQ ID NO: 19 full synthetic operon nucleotide sequence.

The biosynthesis pathway for pseudaminic requires flmA-flmB-flmH-flmD-neuB-flmC in *Caulobacter crescentus*. To prove this Applicants engineered a plasmid pUCIDT-flm_operon_syn expressing flmA-flmB-flmH-flmD-neuB-flmC from the *E. coli* phage T5 promoter. SEQ ID NO: 20 corresponds to the nucleotide sequence of flm operon synthetic with pUCIDT plasmid sequence (pUCIDT-flm-operon-syn). pUCIDT-flm-operon-syn is a plasmid harboring synthetic flm operon that is inducible (by the addition of IPTG (Isopropyl-β-D-thiogalactopyranosid) and used to make Pseudmaninic acid donor in *E. coli.*

SEQ ID NO: 21 corresponds to the fljK(syn)-flmG nucleotide sequence inserted into pSRK-Gm. pSRK-Gm fljK(syn)-flmG is a plasmid harboring synthetic FljK (flagellin, acceptor)-encoding gene and the gene encoding wild-type FlmG (glycosyltransferase). This plasmid is a derivative of pSRK-Gm described by Khan et al, 2008 (PMID: 18606801 PMCID: PMC2519271 DOI: 10.1128/AEM.01098-08) 10. Expression of FljK and FlmG can be induced by the addition of IPTG. This plasmid works in *Caulobacter crescentus* (system 1), *Sinorhizobium fredii* NGR234 (system 2) and *E. coli* (system 3).

Applicants have also constructed a pSRK-Gm derivative with the synthetic flm operon, called pSRK-Gm flm operon syn. SEQ ID NO: 22 corresponds to flm operon sequence that was inserted.

SEQ ID NO: 23 corresponds to mutated FlmG protein sequences.

SEQ ID NO: 24 corresponds to an active fragment of the FljK (flagellin) protein sequence.

SEQ ID NO: 25 corresponds to the full synthetic operon protein sequence.

SEQ ID NO: 26: corresponds to the polynucleotide sequence of the synthetic variant flmG-syn-V553A.

SEQ ID NO: 27: corresponds to the amino acid sequence of the synthetic variant flmG-syn-V553A, which is 88% identical and 92% similar to the natural FlmG. The chimV553A is a chimeric protein in which the first 296 residues (so from 1-296) are identical to the natural FlmG, but the remaining residues (297-596) were replaced with the flmG from *Caulobacter* species YL. Additionally, a mutation was introduced, V553A (valine to alanine at position 553) that enhances activity towards FljK from (and in) *Caulobacter crescentus.*

Applicants also engineered a plasmid pUCIDT-flm-operon-syn-flmG expressing flmA-flmB-flmH-flmD-neuB-flmC and the flmG derived from *Caulobacter crescentus* from the *E. coli* phage T5 promoter. SEQ ID NO: 28 corresponds to the nucleotide sequence of flm operon synthetic and flmG with pUCIDT plasmid sequence (pUCIDT-flm-operon-syn-flmG. pUCIDT-flm-operon-syn-flmG is a plasmid harboring the synthetic flm operon and the native *Caulobacter crescentus* flmG that are inducible (by the addition of IPTG (Isopropyl-β-D-thiogalactopyranosid) and used to make Pseudmaninic acid donor and express FlmG in *E. coli.*

Applicants also engineered a plasmid pUCIDT-flm-operon-syn-flmG (chimV553A) expressing flmA-flmB-flmH-flmD-neuB-flmC and the synthetic flmG designated as SEQ ID NO: 26 from the *E. coli* phage T5 promoter. SEQ ID NO: 29 corresponds to the nucleotide sequence of flm operon synthetic and flmG with pUCIDT plasmid sequence (pUCIDT-flm-operon-syn-flmG (chimV553A). pUCIDT-flm-operon-syn-flmG (chimV553A) is a plasmid harboring the synthetic flm operon and the synthetic flmG that are inducible (by the addition of IPTG (Isopropyl-3-D-thiogalactopyranosid) and used to make Pseudmaninic acid donor and express FlmG in *E. coli.*

The Applicants further developed two fljK mutants fljK_Cc_Bs_flap_syn and fljK_BS_Cc_flap_syn. SEQ ID NO:30 corresponds to the nucleotide sequence of fljK_Cc_Bs_flap_syn and SEQ ID NO:31 corresponds to the amino acid sequence of fljK_Cc_Bs_flap_syn. SEQ ID NO: 32 corresponds to the nucleotide sequence of fljK_Bs_Cc_flap_syn and SEQ ID NO: 33 corresponds to the amino acid sequence of fljK_Bs_Cc_flap_syn.

The appended sequence listing forms part of the application.

CITATION LIST

Non Patent Literature

NPL1: Lairson, L. L., Henrissat, B., Davies, G. J. & Withers, S. G. Glycosyltransferases: structures, functions, and mechanisms. *Annual review of biochemistry* 77, 521-555 (2008).

Lalonde, M. E. & Durocher, Y. Therapeutic glycoprotein production in mammalian cells. *J Biotechnol* 251, 128-140 (2017).

Breyer, C. A., de Oliveira, M. A. & Pessoa, A., Jr. Expression of Glycosylated Proteins in Bacterial System and Purification by Affinity Chromatography. *Methods Mol Biol* 1674, 183-191 (2018).

Kay, E., Cuccui, J. & Wren, B. W. Recent advances in the production of recombinant glycoconjugate vaccines. npj *Vaccines* 4, 16 (2019).

Keys, T. G. & Aebi, M. Engineering protein glycosylation in prokaryotes. *Current Opinion in Systems Biology* 5, 23-31 (2017).

Tytgat, H. L. P., et al. Cytoplasmic glycoengineering enables biosynthesis of nanoscale glycoprotein assemblies. *Nature communications* 10, 5403 (2019).

Parker, J. L., et al. Maf-dependent bacterial flagellin glycosylation occurs before chaperone binding and flagellar T3SS export. *Mol Microbiol* 92, 258-272 (2014).

Sulzenbacher, G., et al. Glycosylate and move! The glycosyltransferase Maf is involved in bacterial flagella formation. *Environmental microbiology* 20, 228-240 (2018).

Le Quere, A. J., et al. Structural characterization of a K-antigen capsular polysaccharide essential for normal symbiotic infection in *Rhizobium* sp. NGR234: deletion of the rkpMNO locus prevents synthesis of 5,7-diacetamido-3,5,7,9-tetradeoxy-non-2-ulosonic acid. *J Biol Chem* 281, 28981-28992 (2006).

Khan, S. R., Gaines, J., Roop, n., R Martin & Farrand, S. K. Broad-host-range expression vectors with tightly regulated promoters and their use to examine the influence of TraR and TraM expression on Ti plasmid quorum sensing. *Appl Environ Microbiol* 74, 5053-5062 (2008).

Faulds-Pain, A., et al. Flagellin redundancy in *Caulobacter crescentus* and its implications for flagellar filament assembly. *J Bacteriol* 193, 2695-2707 (2011).

Thanbichler, M., Iniesta, A. A. & Shapiro, L. A comprehensive set of plasmids for vanillate- and xylose-inducible gene expression in *Caulobacter crescentus. Nucleic Acids Research* 35, e137 (2007).

Schoenhofen, I. C., Vinogradov, E., Whitfield, D. M., Brisson, J. R. & Logan, S. M. The CMP-legionaminic acid pathway in *Campylobacter*: biosynthesis involving novel GDP-linked precursors. *Glycobiology* 19, 715-725 (2009).

Margaret, I., et al. *Sinorhizobium fredii* HH103 rkp-3 genes are required for K-antigen polysaccharide biosynthesis, affect lipopolysaccharide structure and are essential for infection of legumes forming determinate nodules. *Mol Plant Microbe Interact* 25, 825-838 (2012).

Karimova, G., Pidoux, J., Ullmann, A. & Ladant, D. A bacterial two-hybrid system based on a reconstituted signal transduction pathway. *Proc Natl Acad Sci USA* 95, 5752-5756 (1998).

The invention claimed is:

1. A polynucleotide flmG which encodes a Flagellin Modification Protein (FlmG) having glycosyltransferase activity and being selected from the group consisting of a), b), and c):

a) the polynucleotide composed of SEQ ID NO: 26 or the polynucleotide encoding the protein composed of SEQ ID NO: 27;

b) a polynucleotide having 95% or more sequence identity with the polynucleotide sequence of SEQ ID NO: 26 or with the polynucleotide sequence encoding the protein composed of SEQ ID NO: 27, and which encodes a protein having activity that transfers a soluble monosaccharide to the hydroxyl group on a threonine residue of a soluble acceptor protein of interest; and c) a polynucleotide that encodes a protein that has an amino acid sequence having 95% or more sequence identity with the amino acid sequence of SEQ ID NO: 27 and has activity that transfers a soluble monosaccharide to the hydroxyl group on a threonine residue of the soluble acceptor protein of interest;

wherein glycosylation is an O-glycosylation of the soluble acceptor protein of interest in the presence of the monosaccharide which is performed within the cytoplasm of a bacterial Gram-negative cell; and wherein the soluble acceptor protein of interest is selected from the group consisting of:

i. a flagellin;

ii. a protein selected from the group consisting of Alpha-1-Antitrypsin, Interferon-beta, insulin, and an antimicrobial peptide; and iii. a flagellin fused to another soluble protein of interest.

2. A recombinant expression vector for bacterial expression comprising the polynucleotide flmG according to claim 1.

3. A prokaryotic host cell transformed with at least one copy of the recombinant expression vector according to claim 2.

* * * * *

SEQUENCE LISTING

<160> NUMBER OF SEQ ID NOS: 33

<210> SEQ ID NO 1
<211> LENGTH: 596
<212> TYPE: PRT
<213> ORGANISM: Caulobacter crescentus

<400> SEQUENCE: 1

```
Met Ser Arg Lys Ser Ala Leu Glu Ser Ser Ala Ser Val Leu Ala Gln
1               5                   10                  15

Ala Asp Val Gly Ala Ser Gly Ile His Pro Ser Val Ile Ala Asp Ala
            20                  25                  30

Met Gly Asp Ser Ala Ser Ala Glu Ala Leu Glu Arg Leu Asn Arg Ala
        35                  40                  45

Ala Gln Asp Thr Lys Asn Val Asp Asn Ala Lys His Leu Ala Arg Ala
    50                  55                  60

Ile Gln Ala Val Gln Leu Gln Asp Tyr Ala Lys Ala Asp Lys Leu Ala
65                  70                  75                  80

Leu Lys Leu Leu Glu Lys Asp Glu Arg Leu Gly Leu Ala Trp His Ile
                85                  90                  95

Leu Ala Ile Ala Arg Glu Lys Thr Gly Asp Phe Ala Ser Ser Leu Arg
            100                 105                 110

Ala Tyr Glu Ala Ala Leu Ala Leu Leu Pro Asp His Gly Pro Val Ala
        115                 120                 125

Gly Asp Leu Gly Arg Leu Ala Phe Arg Met Asn Met Pro Glu Leu Ala
    130                 135                 140

Ala Lys Phe Phe Ala His Tyr Arg Leu Ala Arg Pro Asp Asp Val Glu
145                 150                 155                 160

Gly Ala Asn Asn Leu Ala Cys Ala Leu Arg Glu Leu Asn Arg Glu Ser
                165                 170                 175

Glu Ala Ile Glu Val Leu Lys Ala Ala Leu Gly Ala Asn Pro Glu Ala
            180                 185                 190

Ala Val Leu Trp Asn Thr Leu Gly Thr Val Leu Cys Asn Ile Gly Asp
        195                 200                 205

Ala Ala Gly Ser Ile Val Phe Phe Asp Glu Ser Leu Arg Leu Ala Pro
    210                 215                 220

Asp Phe Ser Lys Ala Tyr His Asn Arg Ala Phe Ala Arg Leu Asp Leu
225                 230                 235                 240

Gly Glu Ile Glu Ala Ala Leu Ala Asp Cys Glu Ala Ala Met Arg Ser
                245                 250                 255

Pro Gly Ser Pro Glu Asp Leu Ala Met Met Gln Phe Ala Arg Ala Thr
            260                 265                 270

Ile Leu Leu Ala Leu Gly Arg Val Gly Glu Gly Trp Glu Ala Tyr Glu
        275                 280                 285

Ser Arg Phe Ser Pro Ala Leu Ser Asp Ala Pro Arg Phe Gln Ile Pro
    290                 295                 300

Gly Val Arg Trp Ser Gly Gln Asp Leu Arg Gly Lys Arg Leu Met Ile
305                 310                 315                 320

Thr Thr Glu Gln Gly Leu Gly Asp Glu Val Met Phe Ala Asn Met Leu
                325                 330                 335

Pro Asp Ile Val Glu Ala Leu Gly Pro Asp Gly Phe Leu Ser Leu Ala
            340                 345                 350

Val Glu Arg Arg Leu Ala Pro Leu Phe Glu Arg Thr Phe Pro Lys Val
        355                 360                 365
```

```
Glu Val Thr Ala His Arg Thr Ile Ala Tyr Glu Gly Arg Val Phe Arg
    370                 375                 380

Ala Ala Pro Tyr Ile Glu Asn Trp Asp Arg Phe Asp Tyr Trp Ala Ala
385                 390                 395                 400

Ile Gly Asp Phe Leu Pro Ser Leu Arg Pro Thr Ala Glu Ala Phe Pro
                405                 410                 415

Lys Arg Asn Ala Phe Leu Gln Pro Asp Pro Ala Arg Val Ala His Trp
            420                 425                 430

Lys Ala Gln Leu Glu Lys Leu Gly Pro Gly Pro Lys Val Gly Leu Leu
        435                 440                 445

Trp Lys Ser Leu Lys Leu Asn Ala Glu Arg Ala Arg Gln Phe Ser Pro
    450                 455                 460

Phe His Leu Trp Glu Pro Val Leu His Thr Pro Gly Val Val Phe Val
465                 470                 475                 480

Asn Leu Gln Tyr Gly Asp Cys Glu Glu Glu Ile Ala Phe Ala Lys Glu
                485                 490                 495

Glu Leu Gly Val Glu Ile Trp Gln Pro Glu Gly Ile Asp Leu Lys Ala
            500                 505                 510

Asp Leu Asp Asp Val Ala Ala Leu Cys Ala Ala Val Asp Leu Val Ile
        515                 520                 525

Gly Phe Ser Asn Ala Thr Ile Asn Leu Ala Gly Ala Val Gly Thr Pro
    530                 535                 540

Ile Phe Met Leu Thr Gly Ala Ser Ser Trp Thr Arg Leu Gly Thr Glu
545                 550                 555                 560

Tyr Tyr Pro Trp Tyr Pro Ser Val Arg Cys Phe Val Thr Glu Gln Tyr
                565                 570                 575

Gly Val Trp Glu Pro Thr Met Gly Arg Val Ala Thr Ala Leu Arg Asp
            580                 585                 590

Phe Ala Ala Ser
        595
```

<210> SEQ ID NO 2
<211> LENGTH: 1791
<212> TYPE: DNA
<213> ORGANISM: Caulobacter crescentus

<400> SEQUENCE: 2

```
atgtcccgta aaagcgccct ggaatcctcg gcaagcgtcc tggcccaggc cgatgtcggc      60

gcttcgggca tccaccccag cgttatcgcc gacgccatgg gcgattcggc gtccgccgag     120

gcgctggagc gcctgaatcg ggcggcgcag gacaccaaga acgtcgacaa cgccaagcac     180

ttggcgcgcg cgatccaggc cgtgcagctg caggactacg ccaaggccga caagctggcc     240

ctgaagctgc tggagaagga cgagcgactg ggcctagcct ggcacatcct ggcgattgca     300

cgcgagaaga ccggcgattt cgcctcctcg ctgcgggcct atgaagccgc gctggctctg     360

ctgcccgacc atggccccgt cgccggcgac ctgggccgct tggccttccg catgaacatg     420

ccggagctgg cggccaagtt cttcgcacac taccgtctcg ctcggcccga cgacgtcgag     480

ggcgccaaca acctggcgtg cgccctgcgc gagcttaatc gcgaaagcga agccatcgaa     540

gtcctcaagg ccgccctggg cgccaacccc gaggctgcgg tgctgtggaa cacgctgggc     600

acggtgcttt gcaatatcgg cgacgcggcg ggctcgatcg tgttcttcga cgagtccctg     660

cgcctcgcgc ccgacttttc gaaagcctat cacaaccgcg ccttcgccag gctcgatctg     720

ggcgagatag aggccgcgct ggccgattgc gaagccgcca tgcgcagccc cggctcaccg     780
```

-continued

```
gaagatctgg cgatgatgca gttcgcccgc gccacgattc tcctggctct gggccgcgtc    840

ggcgaaggct gggaggctta tgagtcacgc ttctcgccgg cgctgagcga cgcgccacgg    900

ttccagattc ctggcgtccg ctggtcagga caggacctca ggggcaagcg tttgatgatc    960

accaccgagc agggcctcgg cgacgaggtg atgttcgcca acatgttgcc cgacatcgtc   1020

gaagccttgg gcccagacgg cttcctgtcc ctggcggtcg agcgccgtct ggcgccgctg   1080

ttcgagcgca ccttcccgaa ggtcgaggtg accgcccacc gtacgatcgc ctacgaaggc   1140

cgcgtgttcc gggccgcgcc ctatatcgag aactgggacc gcttcgacta ttgggcggcc   1200

atcggcgact tcctgccgag ccttcgcccc accgccgagg cgtttcccaa gcgcaacgcc   1260

ttcctgcagc cggatccggc gcgggtggcc cactggaagg cccaactcga gaagcttggc   1320

cccggcccga aagtcggcct gctctggaag agcctgaaac tgaacgcgga acgcgcgcgg   1380

cagttttcgc ccttccacct gtgggagccg gttttgcaca cgccaggcgt ggtgttcgtg   1440

aacctgcagt atggcgactg cgaggaagag atcgccttcg ccaaggaaga gctgggcgtg   1500

gagatctggc agccggaagg cattgatctg aaggccgacc tcgacgacgt ggccgctctc   1560

tgcgcggcgg tggacctggt gatcgggttc tccaacgcca cgatcaatct ggccggtgcg   1620

gtggggacgc cgatcttcat gctgaccggc gcctcgtcct ggacccgcct cggcaccgaa   1680

tattacccct ggtatccgag cgttcgctgc ttcgtcaccg agcagtacgg ggtctgggaa   1740

ccgaccatgg gtcgcgtcgc caccgctctg cgcgatttcg ccgcatcctg a            1791


<210> SEQ ID NO 3
<211> LENGTH: 273
<212> TYPE: PRT
<213> ORGANISM: Caulobacter crescentus

<400> SEQUENCE: 3

Met Ala Leu Asn Ser Ile Asn Thr Asn Ala Gly Ala Met Ile Ala Leu
1               5                   10                  15

Gln Asn Leu Asn Gly Thr Asn Ser Glu Leu Thr Thr Val Gln Gln Arg
            20                  25                  30

Ile Asn Thr Gly Lys Lys Ile Ala Ser Ala Lys Asp Asn Gly Ala Ile
        35                  40                  45

Trp Ala Thr Ala Lys Asn Gln Ser Ala Thr Ala Ala Ser Met Asn Ala
    50                  55                  60

Val Lys Asp Ser Leu Gln Arg Gly Gln Ser Thr Ile Asp Val Ala Leu
65                  70                  75                  80

Ala Ala Gly Asp Thr Ile Thr Asp Leu Leu Gly Lys Met Lys Glu Lys
                85                  90                  95

Ala Leu Ala Ala Ser Asp Thr Ser Leu Asn Thr Ala Ser Phe Asn Ala
            100                 105                 110

Leu Lys Ser Asp Phe Asp Ser Leu Arg Asp Gln Ile Glu Lys Ala Ala
        115                 120                 125

Thr Asn Ala Lys Phe Asn Gly Val Ser Ile Ala Asp Gly Ser Thr Thr
    130                 135                 140

Lys Leu Thr Phe Leu Ala Asn Ser Asp Gly Ser Gly Phe Thr Val Asn
145                 150                 155                 160

Ala Lys Thr Ile Ser Leu Ala Gly Ile Gly Leu Thr Thr Thr Ser Thr
                165                 170                 175

Phe Thr Thr Ala Ala Ala Ala Lys Thr Met Ile Gly Thr Ile Asp Thr
            180                 185                 190

Ala Leu Gln Thr Ala Thr Asn Lys Leu Ala Ser Leu Gly Thr Ser Ser
```

195                 200                 205

Val Gly Leu Asp Thr His Leu Thr Phe Val Gly Lys Leu Gln Asp Ser
    210                 215                 220

Leu Asp Ala Gly Val Gly Asn Leu Val Asp Ala Asp Leu Ala Lys Glu
225                 230                 235                 240

Ser Ala Lys Leu Gln Ser Leu Gln Thr Lys Gln Gln Leu Gly Val Gln
                245                 250                 255

Ala Leu Ser Ile Ala Asn Gln Ser Ser Ser Ser Ile Leu Ser Leu Phe
            260                 265                 270

Arg

<210> SEQ ID NO 4
<211> LENGTH: 822
<212> TYPE: DNA
<213> ORGANISM: Caulobacter crescentus

<400> SEQUENCE: 4
atggcgctga acagcatcaa tacgaacgcg ggcgcgatga tcgccctgca aaatctgaat 60
ggcacgaatt ccgagctgac gaccgttcag cagcggatca ataccggcaa gaagatcgcc 120
agcgccaagg acaatggcgc catctgggcg accgccaaga accagtcggc caccgccgcc 180
agcatgaacg ccgtgaagga ctcgctgcaa cgcggccagt cgacgatcga cgtcgcgctc 240
gccgccggcg acaccatcac cgacctgctc ggcaagatga aggaaaaggc cctggccgct 300
tccgacacct cgctgaacac cgcctcgttc aacgccctga agtcggactt cgactcgctg 360
cgtgaccaaa tcgaaaaggc cgcgacgaac gccaagttca acggtgtcag catcgcggac 420
ggttcgacca ccaagctgac cttcctggcc aactcggacg gcagcggctt cacggtcaac 480
gccaagacca tctccctggc gggtatcggt ctgacgacca cctcgacctt caccacggcc 540
gccgccgcca agacgatgat cggcaccatc gacacggcgc tgcagacggc gaccaacaag 600
ctggcctcgc tgggcaccag ctcggtcggt ctggacactc acctgacctt cgtcggcaag 660
ctgcaagaca gcctggacgc gggtgtgggc aacctggtgg acgccgacct cgccaaggaa 720
agcgccaagc tgcagtcgct gcaaaccaag cagcagctgg gcgtccaggc gctgtcgatc 780
gccaaccagt cttcgtcctc gatcctgagc ctgttccgtt aa 822

<210> SEQ ID NO 5
<211> LENGTH: 821
<212> TYPE: DNA
<213> ORGANISM: Artificial Sequence
<220> FEATURE:
<223> OTHER INFORMATION: synthetic sequence

<400> SEQUENCE: 5
atggctctga actctattaa caccaacgcc ggcgctatga ttgcactgca gaacctgaat 60
ggtaccaact ccgagctgac gactgttcag cagcgtatca acaccggtaa gaaaattgcg 120
tccgccaaag ataacggcgc aatctgggct accgcaaaaa accaatctgc cactgcagct 180
agcatgaacg ctgttaaaga ctccctgcag cgtggccagt ctaccatcga cgttgccctg 240
gccgccggtg acactatcac cgatctgctg ggtaaaatga aagaaaaggc tctggccgcg 300
tctgacacct ccctgaatac cgcgtctttt aacgccctga aatctgactt cgatagcctg 360
cgtgaccaga tcgagaaggc agcgactaat gctaaattca acggtgttag catcgccgac 420
ggctctacca ctaaactgac cttcctggcc aactctgacg gttctggttt caccgttaac 480
gccaaaacta tttctctggc tggtatcggc ctgaccacta cctccacctt taccaccgcg 540
gcggcggcga agaccatgat cggcactatc gatactgcgc tgcagactgc caccaacaaa 600
ctggcctctc tgggtacctc ctctgtgggt ctggacacgc atctgacttt tgtgggcaaa 660
ctgcaggata gcctggatgc gggcgttggt aacctggtgg atgctgacct ggcaaaggag 720
tctgctaagc tgcaatctct gcagactaaa caacagctgg gcgttcaggc actgtccatc 780
gccaaccaat cttcttcctc tattctgtct ctgtttcgct g 821

<210> SEQ ID NO 6
<211> LENGTH: 107
<212> TYPE: DNA
<213> ORGANISM: Artificial Sequence
<220> FEATURE:
<223> OTHER INFORMATION: Synthetic sequence

<400> SEQUENCE: 6
ggatccagga tccggatgtg agcggataac aattacgagc ttcatgcaca gtgaaatcat 60
gaaaaattta ttggctttgt gagcggataa caattataat atgtgga 107

<210> SEQ ID NO 7
<211> LENGTH: 1068
<212> TYPE: DNA
<213> ORGANISM: Artificial Sequence
<220> FEATURE:
<223> OTHER INFORMATION: Synthetic sequence

<400> SEQUENCE: 7
aagaaggaga taccatatgg ggcgttttag cccaaagagt ttggatctgg acggaaaggt 60
tatcttggta acgggcggta ctggaagctt cgggcgtcgt ttcatcgaga ctgtcttgcg 120
ccgttacgat ccccgcaaag ttatcgtcta ttcgcgcgat gaattaaaac agagtgacat 180
gcaaattgag cttcgcgagc aattcgatga ggccaccgta gcaaagatgc gtttttttct 240
gggcgacgtg cgtgatcgtg agcgtttaac gttagcgctt cgtggagtcg acattgtcat 300
tcatgcagcc gcacttaaac aggtaccagc ggcagaatat aatccctccg aatgtatcca 360
cacgaatgtg ttgggtgcgg aaaacgtagt atgggcgtca ctggctaacg ccgttaagca 420
ggtggtcgcc ttatctacgg acaaagcttg taatccgact aacctgtatg gtgcaacgaa 480
gttggcctct gacaagacgt tcgtggctgc caacaatctg agtggagaca tcgggacccg 540
cttttgcgtg gttcgctatg gtaacgtagt cgggtctcgc ggctcagtag taccacttta 600
tcgtcgtctg ttgagccaag ggcgacggga gttgccagtc acggaccctc gcatgacccg 660
cttctggatt acgttgaatg agggcgtgga cttcgtactt tcttcattga ccatgatgcg 720
cggaggcgag atttttgtgc cgaagatccc cagtatggca atgcctgatt tggtaaaagc 780
catgtctagc actgctgcaa tgaaggtaat cggtatccgc ccaggagaga aacttcatga 840
aatcatgatc agcgcggatg atgcccgcag caccgtggag ttcgatgacc gctatgcaat 900
cgaaccgaat ttcgcagaat ttggccgtga gccctacgca gcaagtgacg gcgctaaacc 960
cgtggccgag gacttcagct acagctcaga caataatcat gactggttgt ctcccgaagg 1020
cttgttagcc atgttagaag agaaggccac gtgaagatct cccccggg 1068

<210> SEQ ID NO 8
<211> LENGTH: 345
<212> TYPE: PRT
<213> ORGANISM: Artificial Sequence
<220> FEATURE:
<223> OTHER INFORMATION: Synthetic sequence

<400> SEQUENCE: 8

```
Met Gly Arg Phe Ser Pro Lys Ser Leu Asp Leu Asp Gly Lys Val Ile
1               5                   10                  15

Leu Val Thr Gly Gly Thr Gly Ser Phe Gly Arg Arg Phe Ile Glu Thr
            20                  25                  30

Val Leu Arg Arg Tyr Asp Pro Arg Lys Val Ile Val Tyr Ser Arg Asp
        35                  40                  45

Glu Leu Lys Gln Ser Asp Met Gln Ile Glu Leu Arg Glu Gln Phe Asp
    50                  55                  60

Glu Ala Thr Val Ala Lys Met Arg Phe Phe Leu Gly Asp Val Arg Asp
65                  70                  75                  80

Arg Glu Arg Leu Thr Leu Ala Leu Arg Gly Val Asp Ile Val Ile His
                85                  90                  95

Ala Ala Ala Leu Lys Gln Val Pro Ala Ala Glu Tyr Asn Pro Ser Glu
            100                 105                 110

Cys Ile His Thr Asn Val Leu Gly Ala Glu Asn Val Val Trp Ala Ser
        115                 120                 125

Leu Ala Asn Ala Val Lys Gln Val Val Ala Leu Ser Thr Asp Lys Ala
    130                 135                 140

Cys Asn Pro Thr Asn Leu Tyr Gly Ala Thr Lys Leu Ala Ser Asp Lys
145                 150                 155                 160

Thr Phe Val Ala Ala Asn Asn Leu Ser Gly Asp Ile Gly Thr Arg Phe
                165                 170                 175

Cys Val Val Arg Tyr Gly Asn Val Val Gly Ser Arg Gly Ser Val Val
            180                 185                 190

Pro Leu Tyr Arg Arg Leu Leu Ser Gln Gly Ala Thr Glu Leu Pro Val
        195                 200                 205

Thr Asp Pro Arg Met Thr Arg Phe Trp Ile Thr Leu Asn Glu Gly Val
    210                 215                 220

Asp Phe Val Leu Ser Ser Leu Thr Met Met Arg Gly Gly Glu Ile Phe
225                 230                 235                 240

Val Pro Lys Ile Pro Ser Met Ala Met Pro Asp Leu Val Lys Ala Met
                245                 250                 255

Ser Ser Thr Ala Ala Met Lys Val Ile Gly Ile Arg Pro Gly Glu Lys
            260                 265                 270

Leu His Glu Ile Met Ile Ser Ala Asp Asp Ala Arg Ser Thr Val Glu
        275                 280                 285

Phe Asp Asp Arg Tyr Ala Ile Glu Pro Asn Phe Ala Glu Phe Gly Arg
    290                 295                 300

Glu Pro Tyr Ala Ala Ser Asp Gly Ala Lys Pro Val Ala Glu Asp Phe
305                 310                 315                 320

Ser Tyr Ser Ser Asp Asn Asn His Asp Trp Leu Ser Pro Glu Gly Leu
                325                 330                 335

Leu Ala Met Leu Glu Glu Lys Ala Thr
            340                 345
```

<210> SEQ ID NO 9
<211> LENGTH: 1190
<212> TYPE: DNA
<213> ORGANISM: Artificial Sequence
<220> FEATURE:
<223> OTHER INFORMATION: Synthetic sequence

<400> SEQUENCE: 9

```
aagaaggaga tataccatga caggcggatt tttaccttat gggcgtcaga ctattgagga     60
```

```
ggatgacatc gctgcggtag cggaagcatt gcgcggcgac tttctgacga ctggccctac    120

agtggaagct ttcgagacag cgttcgccgc taaagtcggc gctgatcacg caatcgcggt    180

atcgaacgga acagctacct tgcaccttgc catgatggct cttggtattg gtgaaggtga    240

tgtatgcgta gcaccaagtg tgacttttct ggcaaccgct aactgtgcac gttatgtagg    300

tgcggaagta gtgttcgccg acgttgaccc ggacagtggt cttatgacac cagacaccct    360

ggcgcgcgct ttggcaggtg cacgtgataa gcgtgttaaa gctgtacttc cagtacatct    420

gcgtggggac gtatgtgatc ttcccgcgtt gaaagcaatg gcatcagcga gcggcgccgt    480

gcttgtggaa gatgccccgc atgccctggg ttcgatcgct acctttgatg gcgtagcgca    540

tccagtcgga gatggtgcgt acagttcatt cgcaagtttc tcctttcacc ccgtaaagac    600

gctggccaca ggggagggag ggatgttgac caccaacgac cccgcactgg ccgcaaaggc    660

gcgtttgctt cgcagtcacg ggatggtccg ccagccgggt ggagatccgt ggtggtacga    720

gatgcccgaa ctgggattca attaccgcat tcctgatgtt ttatgtgcct taggtttatc    780

ccaactggcg aaacttgacc gttttgttgc acgccgtcgt gaccttactg ccctttacgc    840

tcgcttattg gcggagcgcg ctccccgtgc gcgtttagcc accagcccgg accactcaga    900

cgctgcctta cacctgttga cggttttaat tgatttcgag gccgagggta tttcccgccg    960

taccgtagtt gaatccctta aaactcaagg agtaggaacg caggtgcact acatcccggt   1020

gcaccgtcag ccatattatg cacagcgcta cggggtcgcc gacttgcccg gagctgacgc   1080

gtggtacgcc cgttgcttaa ccttgccgct gtatccagct atgactaatg gagacgttga   1140

gcgcgttgtc ggtgctttag ccactgtttt agggtgagct agcggagctc              1190
```

<210> SEQ ID NO 10
<211> LENGTH: 386
<212> TYPE: PRT
<213> ORGANISM: Artificial Sequence
<220> FEATURE:
<223> OTHER INFORMATION: Synthetic sequence

<400> SEQUENCE: 10

```
Met Thr Gly Gly Phe Leu Pro Tyr Gly Arg Gln Thr Ile Glu Glu Asp
1               5                   10                  15

Asp Ile Ala Ala Val Ala Glu Ala Leu Arg Gly Asp Phe Leu Thr Thr
            20                  25                  30

Gly Pro Thr Val Glu Ala Phe Glu Thr Ala Phe Ala Ala Lys Val Gly
        35                  40                  45

Ala Asp His Ala Ile Ala Val Ser Asn Gly Thr Ala Thr Leu His Leu
    50                  55                  60

Ala Met Met Ala Leu Gly Ile Gly Glu Gly Asp Val Cys Val Ala Pro
65                  70                  75                  80

Ser Val Thr Phe Leu Ala Thr Ala Asn Cys Ala Arg Tyr Val Gly Ala
                85                  90                  95

Glu Val Val Phe Ala Asp Val Asp Pro Asp Ser Gly Leu Met Thr Pro
            100                 105                 110

Asp Thr Leu Ala Arg Ala Leu Ala Gly Ala Arg Asp Lys Arg Val Lys
        115                 120                 125

Ala Val Leu Pro Val His Leu Arg Gly Asp Val Cys Asp Leu Pro Ala
    130                 135                 140

Leu Lys Ala Met Ala Ser Ala Ser Gly Ala Val Leu Val Glu Asp Ala
145                 150                 155                 160
```

```
Pro His Ala Leu Gly Ser Ile Ala Thr Phe Asp Gly Val Ala His Pro
                165                 170                 175

Val Gly Asp Gly Ala Tyr Ser Ser Phe Ala Ser Phe Ser Phe His Pro
            180                 185                 190

Val Lys Thr Leu Ala Thr Gly Glu Gly Gly Met Leu Thr Thr Asn Asp
        195                 200                 205

Pro Ala Leu Ala Ala Lys Ala Arg Leu Leu Arg Ser His Gly Met Val
    210                 215                 220

Arg Gln Pro Gly Gly Asp Pro Trp Trp Tyr Glu Met Pro Glu Leu Gly
225                 230                 235                 240

Phe Asn Tyr Arg Ile Pro Asp Val Leu Cys Ala Leu Gly Leu Ser Gln
                245                 250                 255

Leu Ala Lys Leu Asp Arg Phe Val Ala Arg Arg Arg Asp Leu Thr Ala
            260                 265                 270

Leu Tyr Ala Arg Leu Leu Ala Glu Arg Ala Pro Arg Ala Arg Leu Ala
        275                 280                 285

Thr Ser Pro Asp His Ser Asp Ala Ala Leu His Leu Leu Thr Val Leu
    290                 295                 300

Ile Asp Phe Glu Ala Glu Gly Ile Ser Arg Arg Thr Val Val Glu Ser
305                 310                 315                 320

Leu Lys Thr Gln Gly Val Gly Thr Gln Val His Tyr Ile Pro Val His
                325                 330                 335

Arg Gln Pro Tyr Tyr Ala Gln Arg Tyr Gly Val Ala Asp Leu Pro Gly
            340                 345                 350

Ala Asp Ala Trp Tyr Ala Arg Cys Leu Thr Leu Pro Leu Tyr Pro Ala
        355                 360                 365

Met Thr Asn Gly Asp Val Glu Arg Val Val Gly Ala Leu Ala Thr Val
    370                 375                 380

Leu Gly
385
```

```
<210> SEQ ID NO 11
<211> LENGTH: 612
<212> TYPE: DNA
<213> ORGANISM: Artificial sequence
<220> FEATURE:
<223> OTHER INFORMATION: Synthetic sequence

<400> SEQUENCE: 11

aagaaggaga tataccatgg ttgcggtgcg ccttcgtaac ctggtcgaat ctgatcgcga      60

acgccttctt atttggcgca acagtccaga tgttagcgca tatatgtact cagatcataa     120

gattggtcac gaagaacatg accactggtt cgacgtcgcg cgtcatgacc cacgtcgtcg     180

ctactggatt atcgaggctg acggggagcc ggtcggtctt gccaatcttg ctgacattga     240

tttggttcac cgtcgctgtg cttgggccta ctacttggca agccccaaag tgcgtggact     300

gggtgtcggc agttttgttg agttccaaat tatcgaatac gttttcaatc agttgcacct     360

gaacaaattg tggtgcgaag tccttatcag taatgaatcc gtatggcgtc tgcatgaact     420

ttacggcttc cagcgcgagg ctttatttcg ccagcatgtt atgaaacagg gccatgaagt     480

ggacgtaatt ggtttaggac tgcttgccag tgactgggcc gctcgccgcg atgccatggc     540

cgaacgcttg tgtgcgaaag gatatacaat ccccgacttg acctgccgcg cggcctgaga     600

tatcgcggcc gc                                                         612

<210> SEQ ID NO 12
```

<211> LENGTH: 193
<212> TYPE: PRT
<213> ORGANISM: Artificial Sequence
<220> FEATURE:
<223> OTHER INFORMATION: Synthetic sequence

<400> SEQUENCE: 12

```
Met Val Ala Val Arg Leu Arg Asn Leu Val Glu Ser Asp Arg Glu Arg
1               5                   10                  15

Leu Leu Ile Trp Arg Asn Ser Pro Asp Val Ser Ala Tyr Met Tyr Ser
            20                  25                  30

Asp His Lys Ile Gly His Glu Glu His Asp His Trp Phe Asp Val Ala
        35                  40                  45

Arg His Asp Pro Arg Arg Arg Tyr Trp Ile Ile Glu Ala Asp Gly Glu
    50                  55                  60

Pro Val Gly Leu Ala Asn Leu Ala Asp Ile Asp Leu Val His Arg Arg
65                  70                  75                  80

Cys Ala Trp Ala Tyr Tyr Leu Ala Ser Pro Lys Val Arg Gly Leu Gly
                85                  90                  95

Val Gly Ser Phe Val Glu Phe Gln Ile Ile Glu Tyr Val Phe Asn Gln
            100                 105                 110

Leu His Leu Asn Lys Leu Trp Cys Glu Val Leu Ile Ser Asn Glu Ser
        115                 120                 125

Val Trp Arg Leu His Glu Leu Tyr Gly Phe Gln Arg Glu Ala Leu Phe
    130                 135                 140

Arg Gln His Val Met Lys Gln Gly His Glu Val Asp Val Ile Gly Leu
145                 150                 155                 160

Gly Leu Leu Ala Ser Asp Trp Ala Ala Arg Arg Asp Ala Met Ala Glu
                165                 170                 175

Arg Leu Cys Ala Lys Gly Tyr Thr Ile Pro Asp Leu Thr Cys Arg Ala
            180                 185                 190

Ala
```

<210> SEQ ID NO 13
<211> LENGTH: 1018
<212> TYPE: DNA
<213> ORGANISM: Artificial Sequence
<220> FEATURE:
<223> OTHER INFORMATION: synthetic sequence

<400> SEQUENCE: 13

```
aagaaggaga tataccatgt ccttacgcat cgtctttgta tgcgcagccg gcccatctgt     60

gggtggtgga catgtcatgc gttccttgac acttgcacgc gcgttagcgg cgcgcggagc    120

gacatgtgcg tttttgggaa cacccgaggt agcagcagtc ttagacgcct tcggtcctga    180

tatggcgcgt gccgacaccg ccgagccctt cgaagctgta gtctttgact cctatgcact    240

taccgcggac gaccatcgcc gtatcgcggc gggacgtccc gcgttagtaa tcgacgattt    300

agccgaccgc cctcttgcag cagacctggt gcttgatgct ggaccggctc gccgcgccga    360

ggattacgca ggactggtgc ccgcacatgc acgtcttctg ctgggtccga atcacgcacc    420

ggtccgtcca gcttttgttg cgttacgcga ggcagcctta gcacgccgtg cgcagcaggg    480

accggtacgt cgcattcttg tatctctggg catgacggac gtggggggaa ttacaggacg    540

tgtggtcgca cttcttgccc caatccttgg ggaggtcact ctggatcttg tggtgggagc    600

gggagccccg agcttgcctg ctctgcgtgc attagccgct gaagaccctc gccttgttct    660

tcatattgac acgcaggata tgccacgcct tgttcttgaa gccgacttgg ccatcggcgc    720
```

```
aggaggttcc acgacgtggg agcgctgtgt ccttgccttg ccagctttga ctcttatctt    780

agccgataac caaattgccg cggcacgtgc tcttgaagca gctggcgtaa ccccttgttt    840

ggacgtaaca gccccggatt ttgacacggc ctttgcagct cttgcgcaga acctgattgc    900

tgatccggat cgtcgtgccg cacttagtgc tgcctcagct acggtctgtg atggacgtgg    960

cgcggagcgc gtggctgaag cattcttggg agtcaccacc acatgacaat tgctgcag     1018


<210> SEQ ID NO 14
<211> LENGTH: 329
<212> TYPE: PRT
<213> ORGANISM: Artificial sequence
<220> FEATURE:
<223> OTHER INFORMATION: Synthetic sequence

<400> SEQUENCE: 14

Met Ser Leu Arg Ile Val Phe Val Cys Ala Ala Gly Pro Ser Val Gly
1               5                   10                  15

Gly Gly His Val Met Arg Ser Leu Thr Leu Ala Arg Ala Leu Ala Ala
            20                  25                  30

Arg Gly Ala Thr Cys Ala Phe Leu Gly Thr Pro Glu Val Ala Ala Val
        35                  40                  45

Leu Asp Ala Phe Gly Pro Asp Met Ala Arg Ala Asp Thr Ala Glu Pro
    50                  55                  60

Phe Glu Ala Val Val Phe Asp Ser Tyr Ala Leu Thr Ala Asp Asp His
65                  70                  75                  80

Arg Arg Ile Ala Ala Gly Arg Pro Ala Leu Val Ile Asp Asp Leu Ala
                85                  90                  95

Asp Arg Pro Leu Ala Ala Asp Leu Val Leu Asp Ala Gly Pro Ala Arg
            100                 105                 110

Arg Ala Glu Asp Tyr Ala Gly Leu Val Pro Ala His Ala Arg Leu Leu
        115                 120                 125

Leu Gly Pro Asn His Ala Pro Val Arg Pro Ala Phe Val Ala Leu Arg
    130                 135                 140

Glu Ala Ala Leu Ala Arg Arg Ala Gln Gln Gly Pro Val Arg Arg Ile
145                 150                 155                 160

Leu Val Ser Leu Gly Met Thr Asp Val Gly Gly Ile Thr Gly Arg Val
                165                 170                 175

Val Ala Leu Leu Ala Pro Ile Leu Gly Glu Val Thr Leu Asp Leu Val
            180                 185                 190

Val Gly Ala Gly Ala Pro Ser Leu Pro Ala Leu Arg Ala Leu Ala Ala
        195                 200                 205

Glu Asp Pro Arg Leu Val Leu His Ile Asp Thr Gln Asp Met Pro Arg
    210                 215                 220

Leu Val Leu Glu Ala Asp Leu Ala Ile Gly Ala Gly Gly Ser Thr Thr
225                 230                 235                 240

Trp Glu Arg Cys Val Leu Ala Leu Pro Ala Leu Thr Leu Ile Leu Ala
                245                 250                 255

Asp Asn Gln Ile Ala Ala Ala Arg Ala Leu Glu Ala Ala Gly Val Thr
            260                 265                 270

Pro Cys Leu Asp Val Thr Ala Pro Asp Phe Asp Thr Ala Phe Ala Ala
        275                 280                 285

Leu Ala Gln Asn Leu Ile Ala Asp Pro Asp Arg Arg Ala Ala Leu Ser
    290                 295                 300

Ala Ala Ser Ala Thr Val Cys Asp Gly Arg Gly Ala Glu Arg Val Ala
```

305 310 315 320

Glu Ala Phe Leu Gly Val Thr Thr Thr
325

<210> SEQ ID NO 15
<211> LENGTH: 1101
<212> TYPE: DNA
<213> ORGANISM: Artificial Sequence
<220> FEATURE:
<223> OTHER INFORMATION: Synthetic sequence

<400> SEQUENCE: 15
aagaaggaga tataccatgt ccgctccgag taccgagatc cccccttcga ttgagattgc 60
tggacgcaag atcggggccg atcacagccc ctacgttatc tgtgagttgt cgggcaatca 120
taatgggtcc cttgaacgtt gcttagctat ggtagacgct gccgcagata ccggatgcga 180
cgccatcaaa attcaaactt acacagccga cacaatcacc ttggatgtag atcgtccgga 240
gttcaaaatc cacgggggat tgtgggatgg acgcactctg tatgagcttt atgaggaagc 300
tcatactccc tttgagtggc acgcggccat cttcgaacgc gctcgtcagc gcggtgtcac 360 gatttttct tctccatttg acgagactgc cgtcgacctt ttagattcgc tgggggcgcc 420
agcttttaaa attgcaagct ttgaagcggt agaccttccg cttatcaaat acgcggcagc 480
caaagggaaa cccttaatta tttccactgg aatggcgaac cttacggaga tgcaaaccgc 540
ccttgataca gctttgtcag caggcgctcc gggagtgtta cttttacact gtgtttcttc 600
ataccctgct acgttcgcag acgcgaacgt ccgcaccgtg ccggatatgg cggcacgctt 660
cggatgcccg attggccttt ccgatcacac gcccggtaca gcagctagtg tcgccgctgt 720
gagcttaggg gcgtgtgcag tagaaaaaca tttcacgctt gcccgtgccg atggtggtcc 780
ggacgccgca ttctctcttg aacctgcgga gtttaaggca ttagttgatg acacaaagaa 840
tgcttgggct gcgttgggac gtgcacacta cgatgtgctg gggtcagagg caacatcact 900
gttattccgc cgttctctgt acgttacagc cgacgtgaag gctggcgaac ctttaacgcg 960
cgcgaatgtt cgttcagtgc gtcccggcaa tgggttgcca cctgcggatt tggataaagt 1020
tctggcggga aaggcaaccc gcgatcttgc gcgcggcgag cctcttgact ggtcaatggt 1080
cggttgaaac tagtacttaa g 1101

<210> SEQ ID NO 16
<211> LENGTH: 356
<212> TYPE: PRT
<213> ORGANISM: Artificial sequence
<220> FEATURE:
<223> OTHER INFORMATION: Synthetic sequence

<400> SEQUENCE: 16

Met Ser Ala Pro Ser Thr Glu Ile Pro Pro Ser Ile Glu Ile Ala Gly
1 5 10 15

Arg Lys Ile Gly Ala Asp His Ser Pro Tyr Val Ile Cys Glu Leu Ser
20 25 30

Gly Asn His Asn Gly Ser Leu Glu Arg Cys Leu Ala Met Val Asp Ala
35 40 45

Ala Ala Asp Thr Gly Cys Asp Ala Ile Lys Ile Gln Thr Tyr Thr Ala
50 55 60

Asp Thr Ile Thr Leu Asp Val Asp Arg Pro Glu Phe Lys Ile His Gly
65 70 75 80

Gly Leu Trp Asp Gly Arg Thr Leu Tyr Glu Leu Tyr Glu Glu Ala His

```
                85                  90                  95

Thr Pro Phe Glu Trp His Ala Ala Ile Phe Glu Arg Ala Arg Gln Arg
            100                 105                 110

Gly Val Thr Ile Phe Ser Ser Pro Phe Asp Glu Thr Ala Val Asp Leu
        115                 120                 125

Leu Asp Ser Leu Gly Ala Pro Ala Phe Lys Ile Ala Ser Phe Glu Ala
    130                 135                 140

Val Asp Leu Pro Leu Ile Lys Tyr Ala Ala Ala Lys Gly Lys Pro Leu
145                 150                 155                 160

Ile Ile Ser Thr Gly Met Ala Asn Leu Thr Glu Met Gln Thr Ala Leu
                165                 170                 175

Asp Thr Ala Leu Ser Ala Gly Ala Pro Gly Val Leu Leu Leu His Cys
            180                 185                 190

Val Ser Ser Tyr Pro Ala Thr Phe Ala Asp Ala Asn Val Arg Thr Val
        195                 200                 205

Pro Asp Met Ala Ala Arg Phe Gly Cys Pro Ile Gly Leu Ser Asp His
    210                 215                 220

Thr Pro Gly Thr Ala Ala Ser Val Ala Ala Val Ser Leu Gly Ala Cys
225                 230                 235                 240

Ala Val Glu Lys His Phe Thr Leu Ala Arg Ala Asp Gly Gly Pro Asp
                245                 250                 255

Ala Ala Phe Ser Leu Glu Pro Ala Glu Phe Lys Ala Leu Val Asp Asp
            260                 265                 270

Thr Lys Asn Ala Trp Ala Ala Leu Gly Arg Ala His Tyr Asp Val Leu
        275                 280                 285

Gly Ser Glu Ala Thr Ser Leu Leu Phe Arg Arg Ser Leu Tyr Val Thr
    290                 295                 300

Ala Asp Val Lys Ala Gly Glu Pro Leu Thr Arg Ala Asn Val Arg Ser
305                 310                 315                 320

Val Arg Pro Gly Asn Gly Leu Pro Pro Ala Asp Leu Asp Lys Val Leu
                325                 330                 335

Ala Gly Lys Ala Thr Arg Asp Leu Ala Arg Gly Glu Pro Leu Asp Trp
            340                 345                 350

Ser Met Val Gly
        355


<210> SEQ ID NO 17
<211> LENGTH: 759
<212> TYPE: DNA
<213> ORGANISM: Artificial sequence
<220> FEATURE:
<223> OTHER INFORMATION: Synthetic sequence

<400> SEQUENCE: 17

aagaaggaga tataccatga tcttggccat cctgcaagcc cgcatgtcat ccacgcgcct      60

tcctggcaag gtactgatgc cctgcaacg ccagcccatg atcgttcgtc agatcgaacg      120

tgttgcccgc tcaaaacgca ttgataagtt agttgtggcc acgtcggacc gcccagagga     180

cgatgcaatc gaagcagccg ttcgccgtga aggtattgcg gtgtttcgcg ggtcattaga     240

caatgtccag cagcgtttta ttggggcatt ggatgcccac cctgccgacc atgtagtacg     300

tctgaccgcc gattgtcccc ttgccgaccc gacacttatt gatgccacaa tcgatttatg     360

tctttcaaag ggcgcggact acgtatctaa tacaccggag ggtcacgccc atccaaaagg     420

gaccgatgta gaggtaatga ccgcagcggc attgcgtcgc gcggctgctg aagccacgac     480
```

```
caaagaagca tttgaacacg ttacttggga cctttggaac caacctcaac gctggacgtg    540

tgcatggttg ccgtgcttcc cagatcaagg agcggtacgc tggactgtgg atcgtccgga    600

tgattatgct tttgtcgctg ctgtatacga tgccctgtac ccagcaaatc gcgcctttac    660

gtcggatgac atccgtgcgt ttgtcgctgg tcgccccgac ctgcaagatt atggtggtga    720

tcgccgtgca tgagaattcc tcggcctcta gaactcgag                           759


<210> SEQ ID NO 18
<211> LENGTH: 238
<212> TYPE: PRT
<213> ORGANISM: Artificial sequence
<220> FEATURE:
<223> OTHER INFORMATION: Synthetic sequence

<400> SEQUENCE: 18

Met Ile Leu Ala Ile Leu Gln Ala Arg Met Ser Ser Thr Arg Leu Pro
1               5                   10                  15

Gly Lys Val Leu Met Pro Leu Gln Arg Gln Pro Met Ile Val Arg Gln
            20                  25                  30

Ile Glu Arg Val Ala Arg Ser Lys Arg Ile Asp Lys Leu Val Val Ala
        35                  40                  45

Thr Ser Asp Arg Pro Glu Asp Asp Ala Ile Glu Ala Ala Val Arg Arg
    50                  55                  60

Glu Gly Ile Ala Val Phe Arg Gly Ser Leu Asp Asn Val Gln Gln Arg
65                  70                  75                  80

Phe Ile Gly Ala Leu Asp Ala His Pro Ala Asp His Val Val Arg Leu
                85                  90                  95

Thr Ala Asp Cys Pro Leu Ala Asp Pro Thr Leu Ile Asp Ala Thr Ile
            100                 105                 110

Asp Leu Cys Leu Ser Lys Gly Ala Asp Tyr Val Ser Asn Thr Pro Glu
        115                 120                 125

Gly His Ala His Pro Lys Gly Thr Asp Val Glu Val Met Thr Ala Ala
    130                 135                 140

Ala Leu Arg Arg Ala Ala Ala Glu Ala Thr Thr Lys Glu Ala Phe Glu
145                 150                 155                 160

His Val Thr Trp Asp Leu Trp Asn Gln Pro Gln Arg Trp Thr Cys Ala
                165                 170                 175

Trp Leu Pro Cys Phe Pro Asp Gln Gly Ala Val Arg Trp Thr Val Asp
            180                 185                 190

Arg Pro Asp Asp Tyr Ala Phe Val Ala Ala Val Tyr Asp Ala Leu Tyr
        195                 200                 205

Pro Ala Asn Arg Ala Phe Thr Ser Asp Asp Ile Arg Ala Phe Val Ala
    210                 215                 220

Gly Arg Pro Asp Leu Gln Asp Tyr Gly Gly Asp Arg Arg Ala
225                 230                 235


<210> SEQ ID NO 19
<211> LENGTH: 5848
<212> TYPE: DNA
<213> ORGANISM: Artificial Sequence
<220> FEATURE:
<223> OTHER INFORMATION: Synthetic sequence

<400> SEQUENCE: 19

ggatccggat gtgagcggat aacaattacg agcttcatgc acagtgaaat catgaaaaat     60

ttattggctt tgtgagcgga taacaattat aatatgtgga aagaaggaga taccatatgg    120
```

-continued

```
ggcgttttag cccaaagagt ttggatctgg acggaaaggt tatcttggta acgggcggta    180
ctggaagctt cgggcgtcgt ttcatcgaga ctgtcttgcg ccgttacgat ccccgcaaag    240
ttatcgtcta ttcgcgcgat gaattaaaac agagtgacat gcaaattgag cttcgcgagc    300
aattcgatga ggccaccgta gcaaagatgc gtttttttct gggcgacgtg cgtgatcgtg    360
agcgtttaac gttagcgctt cgtggagtcg acattgtcat tcatgcagcc gcacttaaac    420
aggtaccagc ggcagaatat aatccctccg aatgtatcca cacgaatgtg ttgggtgcgg    480
aaaacgtagt atgggcgtca ctggctaacg ccgttaagca ggtggtcgcc ttatctacgg    540
acaaagcttg taatccgact aacctgtatg gtgcaacgaa gttggcctct gacaagacgt    600
tcgtggctgc caacaatctg agtggagaca tcgggacccg cttttgcgtg gttcgctatg    660
gtaacgtagt cgggtctcgc ggctcagtag taccacttta tcgtcgtctg ttgagccaag    720
gggcgacgga gttgccagtc acggaccctc gcatgacccg cttctggatt acgttgaatg    780
agggcgtgga cttcgtactt tcttcattga ccatgatgcg cggaggcgag atttttgtgc    840
cgaagatccc cagtatggca atgcctgatt tggtaaaagc catgtctagc actgctgcaa    900
tgaaggtaat cggtatccgc ccaggagaga aacttcatga aatcatgatc agcgcggatg    960
atgcccgcag caccgtggag ttcgatgacc gctatgcaat cgaaccgaat ttcgcagaat   1020
ttggccgtga gccctacgca gcaagtgacg gcgctaaacc cgtggccgag gacttcagct   1080
acagctcaga caataatcat gactggttgt ctcccgaagg cttgttagcc atgttagaag   1140
agaaggccac gtgaagatct cccccgggaa gaaggagata taccatgaca ggcggatttt   1200
taccttatgg gcgtcagact attgaggagg atgacatcgc tgcggtagcg gaagcattgc   1260
gcggcgactt tctgacgact ggccctacag tggaagcttt cgagacagcg ttcgccgcta   1320
aagtcggcgc tgatcacgca atcgcggtat cgaacggaac agctaccttg caccttgcca   1380
tgatggctct tggtattggt gaaggtgatg tatgcgtagc accaagtgtg acttttctgg   1440
caaccgctaa ctgtgcacgt tatgtaggtg cggaagtagt gttcgccgac gttgacccgg   1500
acagtggtct tatgacacca gacaccctgg cgcgcgcttt ggcaggtgca cgtgataagc   1560
gtgttaaagc tgtacttcca gtacatctgc gtggggacgt atgtgatctt cccgcgttga   1620
aagcaatggc atcagcgagc ggcgccgtgc ttgtggaaga tgccccgcat gccctgggtt   1680
cgatcgctac ctttgatggc gtagcgcatc cagtcggaga tggtgcgtac agttcattcg   1740
caagtttctc ctttcacccc gtaaagacgc tggccacagg ggagggaggg atgttgacca   1800
ccaacgaccc cgcactggcc gcaaaggcgc gtttgcttcg cagtcacggg atggtccgcc   1860
agccgggtgg agatccgtgg tggtacgaga tgcccgaact gggattcaat taccgcattc   1920
ctgatgtttt atgtgcctta ggtttatccc aactggcgaa acttgaccgt tttgttgcac   1980
gccgtcgtga ccttactgcc ctttacgctc gcttattggc ggagcgcgct ccccgtgcgc   2040
gtttagccac cagcccggac cactcagacg ctgccttaca cctgttgacg gttttaattg   2100
atttcgaggc cgagggtatt tcccgccgta ccgtagttga atcccttaaa actcaaggag   2160
taggaacgca ggtgcactac atcccggtgc accgtcagcc atattatgca cagcgctacg   2220
gggtcgccga cttgcccgga gctgacgcgt ggtacgcccg ttgcttaacc ttgccgctgt   2280
atccagctat gactaatgga gacgttgagc gcgttgtcgg tgctttagcc actgttttag   2340
ggtgagctag cggagctcaa gaaggagata taccatggtt gcggtgcgcc ttcgtaacct   2400
ggtcgaatct gatcgcgaac gccttcttat ttggcgcaac agtccagatg ttagcgcata   2460
tatgtactca gatcataaga ttggtcacga agaacatgac cactggttcg acgtcgcgcg   2520
```

```
tcatgaccca cgtcgtcgct actggattat cgaggctgac ggggagccgg tcggtcttgc   2580

caatcttgct gacattgatt tggttcaccg tcgctgtgct tgggcctact acttggcaag   2640

ccccaaagtg cgtggactgg gtgtcggcag ttttgttgag ttccaaatta tcgaatacgt   2700

tttcaatcag ttgcacctga acaaattgtg gtgcgaagtc cttatcagta atgaatccgt   2760

atggcgtctg catgaacttt acggcttcca gcgcgaggct ttatttcgcc agcatgttat   2820

gaaacagggc catgaagtgg acgtaattgg tttaggactg cttgccagtg actgggccgc   2880

tcgccgcgat gccatggccg aacgcttgtg tgcgaaagga tatacaatcc ccgacttgac   2940

ctgccgcgcg gcctgagata tcgcggccgc aagaaggaga tataccatgt ccttacgcat   3000

cgtctttgta tgcgcagccg gcccatctgt gggtggtgga catgtcatgc gttccttgac   3060

acttgcacgc gcgttagcgg cgcgcggagc gacatgtgcg tttttgggaa cacccgaggt   3120

agcagcagtc ttagacgcct tcggtcctga tatggcgcgt gccgacaccg ccgagccctt   3180

cgaagctgta gtctttgact cctatgcact taccgcggac gaccatcgcc gtatcgcggc   3240

gggacgtccc gcgttagtaa tcgacgattt agccgaccgc cctcttgcag cagacctggt   3300

gcttgatgct ggaccggctc gccgcgccga ggattacgca ggactggtgc ccgcacatgc   3360

acgtcttctg ctgggtccga atcacgcacc ggtccgtcca gcttttgttg cgttacgcga   3420

ggcagcctta gcacgccgtg cgcagcaggg accggtacgt cgcattcttg tatctctggg   3480

catgacggac gtggggggaa ttacaggacg tgtggtcgca cttcttgccc caatccttgg   3540

ggaggtcact ctggatcttg tggtgggagc gggagccccg agcttgcctg ctctgcgtgc   3600

attagccgct gaagaccctc gccttgttct tcatattgac acgcaggata tgccacgcct   3660

tgttcttgaa gccgacttgg ccatcggcgc aggaggttcc acgacgtggg agcgctgtgt   3720

ccttgccttg ccagctttga ctcttatctt agccgataac caaattgccg cggcacgtgc   3780

tcttgaagca gctggcgtaa ccccttgttt ggacgtaaca gccccggatt ttgacacggc   3840

ctttgcagct cttgcgcaga acctgattgc tgatccggat cgtcgtgccg cacttagtgc   3900

tgcctcagct acggtctgtg atggacgtgg cgcggagcgc gtggctgaag cattcttggg   3960

agtcaccacc acatgacaat tgctgcagaa gaaggagata taccatgtcc gctccgagta   4020

ccgagatccc cccttcgatt gagattgctg gacgcaagat cggggccgat cacagcccct   4080

acgttatctg tgagttgtcg ggcaatcata atgggtccct tgaacgttgc ttagctatgg   4140

tagacgctgc cgcagatacc ggatgcgacg ccatcaaaat tcaaacttac acagccgaca   4200

caatcacctt ggatgtagat cgtccggagt tcaaaatcca cgggggattg tgggatggac   4260

gcactctgta tgagctttat gaggaagctc atactccctt tgagtggcac gcggccatct   4320

tcgaacgcgc tcgtcagcgc ggtgtcacga ttttttcttc tccatttgac gagactgccg   4380

tcgacctttt agattcgctg gggcgccag ctttaaaat tgcaagcttt gaagcggtag   4440

accttccgct tatcaaatac gcggcagcca aagggaaacc cttaattatt tccactggaa   4500

tggcgaacct tacggagatg caaaccgccc ttgatacagc tttgtcagca ggcgctccgg   4560

gagtgttact tttacactgt gtttcttcat accctgctac gttcgcagac gcgaacgtcc   4620

gcaccgtgcc ggatatggcg gcacgcttcg gatgcccgat tggcctttcc gatcacacgc   4680

ccggtacagc agctagtgtc gccgctgtga gcttaggggc gtgtgcagta gaaaaacatt   4740

tcacgcttgc ccgtgccgat ggtggtccgg acgccgcatt ctctcttgaa cctgcggagt   4800

ttaaggcatt agttgatgac acaaagaatg cttgggctgc gttgggacgt gcacactacg   4860
```

```
atgtgctggg gtcagaggca acatcactgt tattccgccg ttctctgtac gttacagccg   4920

acgtgaaggc tggcgaacct ttaacgcgcg cgaatgttcg ttcagtgcgt cccggcaatg   4980

ggttgccacc tgcggatttg gataaagttc tggcgggaaa ggcaacccgc gatcttgcgc   5040

gcggcgagcc tcttgactgg tcaatggtcg gttgaaacta gtacttaaga agaaggagat   5100

ataccatgat cttggccatc ctgcaagccc gcatgtcatc cacgcgcctt cctggcaagg   5160

tactgatgcc cctgcaacgc cagcccatga tcgttcgtca gatcgaacgt gttgcccgct   5220

caaaacgcat tgataagtta gttgtggcca cgtcggaccg cccagaggac gatgcaatcg   5280

aagcagccgt tcgccgtgaa ggtattgcgg tgtttcgcgg gtcattagac aatgtccagc   5340

agcgttttat tggggcattg gatgcccacc ctgccgacca tgtagtacgt ctgaccgccg   5400

attgtcccct tgccgacccg acacttattg atgccacaat cgatttatgt ctttcaaagg   5460

gcgcggacta cgtatctaat acaccggagg gtcacgccca tccaaaaggg accgatgtag   5520

aggtaatgac cgcagcggca ttgcgtcgcg cggctgctga agccacgacc aaagaagcat   5580

ttgaacacgt tacttgggac ctttggaacc aacctcaacg ctggacgtgt gcatggttgc   5640

cgtgcttccc agatcaagga gcggtacgct ggactgtgga tcgtccggat gattatgctt   5700

ttgtcgctgc tgtatacgat gccctgtacc cagcaaatcg cgcctttacg tcggatgaca   5760

tccgtgcgtt tgtcgctggt cgccccgacc tgcaagatta tggtggtgat cgccgtgcat   5820

gagaattcct cggcctctag aactcgag                                     5848
```

```
<210> SEQ ID NO 20
<211> LENGTH: 8600
<212> TYPE: DNA
<213> ORGANISM: Artificial Sequence
<220> FEATURE:
<223> OTHER INFORMATION: Synthetic sequence

<400> SEQUENCE: 20

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accaaatgcg gtgtgaaata ccgcacagat gcgtaaggag aaaataccgc atcaggcgcc    240

attcgccatt caggctgcgc aactgttggg aagggcgatc ggtgcgggcc tcatcgctat    300

tacgccagct ggcgaaaggg ggatgtgctg caaggcgatt aagttgggta acgccagggt    360

tttcccagtc acgacgttgt aaaacgacgg ccagtgcaac gcgatgacga tggatagcga    420

ttcatcgatg agctgacccg atcgccgccg ccggagggtt gcgtttgaga cgggcgacag    480

atggatccgg atgtgagcgg ataacaatta cgagcttcat gcacagtgaa atcatgaaaa    540

atttattggc tttgtgagcg gataacaatt ataatatgtg gaaagaagga gataccatat    600

ggggcgtttt agcccaaaga gtttggatct ggacggaaag gttatcttgg taacgggcgg    660

tactggaagc ttcgggcgtc gtttcatcga gactgtcttg cgccgttacg atccccgcaa    720

agttatcgtc tattcgcgcg atgaattaaa acagagtgac atgcaaattg agcttcgcga    780

gcaattcgat gaggccaccg tagcaaagat gcgttttttt ctgggcgacg tgcgtgatcg    840

tgagcgttta acgttagcgc ttcgtggagt cgacattgtc attcatgcag ccgcacttaa    900

acaggtacca gcggcagaat ataatccctc cgaatgtatc cacacgaatg tgttgggtgc    960

ggaaaacgta gtatgggcgt cactggctaa cgccgttaag caggtggtcg ccttatctac   1020

ggacaaagct tgtaatccga ctaacctgta tggtgcaacg aagttggcct ctgacaagac   1080
```

```
gttcgtggct gccaacaatc tgagtggaga catcgggacc cgcttttgcg tggttcgcta   1140
tggtaacgta gtcgggtctc gcggctcagt agtaccactt tatcgtcgtc tgttgagcca   1200
aggggcgacg gagttgccag tcacggaccc tcgcatgacc cgcttctgga ttacgttgaa   1260
tgagggcgtg gacttcgtac tttcttcatt gaccatgatg cgcggaggcg agatttttgt   1320
gccgaagatc cccagtatgg caatgcctga tttggtaaaa gccatgtcta gcactgctgc   1380
aatgaaggta atcggtatcc gcccaggaga gaaacttcat gaaatcatga tcagcgcgga   1440
tgatgcccgc agcaccgtgg agttcgatga ccgctatgca atcgaaccga atttcgcaga   1500
atttggccgt gagccctacg cagcaagtga cggcgctaaa cccgtggccg aggacttcag   1560
ctacagctca gacaataatc atgactggtt gtctcccgaa ggcttgttag ccatgttaga   1620
agagaaggcc acgtgaagat ctcccccggg aagaaggaga tataccatga caggcggatt   1680
tttaccttat gggcgtcaga ctattgagga ggatgacatc gctgcggtag cggaagcatt   1740
gcgcggcgac tttctgacga ctggccctac agtggaagct ttcgagacag cgttcgccgc   1800
taaagtcggc gctgatcacg caatcgcggt atcgaacgga acagctacct tgcaccttgc   1860
catgatggct cttggtattg gtgaaggtga tgtatgcgta gcaccaagtg tgacttttct   1920
ggcaaccgct aactgtgcac gttatgtagg tgcggaagta gtgttcgccg acgttgaccc   1980
ggacagtggt cttatgacac cagacaccct ggcgcgcgct ttggcaggtg cacgtgataa   2040
gcgtgttaaa gctgtacttc cagtacatct gcgtggggac gtatgtgatc ttcccgcgtt   2100
gaaagcaatg gcatcagcga gcggcgccgt gcttgtggaa gatgccccgc atgccctggg   2160
ttcgatcgct acctttgatg gcgtagcgca tccagtcgga gatggtgcgt acagttcatt   2220
cgcaagtttc tcctttcacc ccgtaaagac gctggccaca ggggagggag ggatgttgac   2280
caccaacgac cccgcactgg ccgcaaaggc gcgtttgctt cgcagtcacg ggatggtccg   2340
ccagccgggt ggagatccgt ggtggtacga gatgcccgaa ctgggattca attaccgcat   2400
tcctgatgtt ttatgtgcct taggtttatc ccaactggcg aaacttgacc gttttgttgc   2460
acgccgtcgt gaccttactg ccctttacgc tcgcttattg gcggagcgcg ctccccgtgc   2520
gcgtttagcc accagcccgg accactcaga cgctgcctta cacctgttga cggttttaat   2580
tgatttcgag gccgagggta tttcccgccg taccgtagtt gaatccctta aaactcaagg   2640
agtaggaacg caggtgcact acatcccggt gcaccgtcag ccatattatg cacagcgcta   2700
cggggtcgcc gacttgcccg gagctgacgc gtggtacgcc cgttgcttaa ccttgccgct   2760
gtatccagct atgactaatg gagacgttga gcgcgttgtc ggtgctttag ccactgtttt   2820
agggtgagct agcggagctc aagaaggaga tataccatgg ttgcggtgcg ccttcgtaac   2880
ctggtcgaat ctgatcgcga acgccttctt atttggcgca acagtccaga tgttagcgca   2940
tatatgtact cagatcataa gattggtcac gaagaacatg accactggtt cgacgtcgcg   3000
cgtcatgacc cacgtcgtcg ctactggatt atcgaggctg acggggagcc ggtcggtctt   3060
gccaatcttg ctgacattga tttggttcac cgtcgctgtg cttgggccta ctacttggca   3120
agccccaaag tgcgtggact gggtgtcggc agttttgttg agttccaaat tatcgaatac   3180
gttttcaatc agttgcacct gaacaaattg tggtgcgaag tccttatcag taatgaatcc   3240
gtatggcgtc tgcatgaact ttacggcttc cagcgcgagg ctttatttcg ccagcatgtt   3300
atgaaacagg gccatgaagt ggacgtaatt ggtttaggac tgcttgccag tgactgggcc   3360
gctcgccgcg atgccatggc cgaacgcttg tgtgcgaaag gatatacaat ccccgacttg   3420
```

-continued

```
acctgccgcg cggcctgaga tatcgcggcc gcaagaagga gatataccat gtccttacgc   3480
atcgtctttg tatgcgcagc cggcccatct gtgggtggtg gacatgtcat gcgttccttg   3540
acacttgcac gcgcgttagc ggcgcgcgga gcgacatgtg cgtttttggg aacacccgag   3600
gtagcagcag tcttagacgc cttcggtcct gatatggcgc gtgccgacac cgccgagccc   3660
ttcgaagctg tagtctttga ctcctatgca cttaccgcgg acgaccatcg ccgtatcgcg   3720
gcgggacgtc ccgcgttagt aatcgacgat ttagccgacc gccctcttgc agcagacctg   3780
gtgcttgatg ctggaccggc tcgccgcgcc gaggattacg caggactggt gcccgcacat   3840
gcacgtcttc tgctgggtcc gaatcacgca ccggtccgtc cagcttttgt tgcgttacgc   3900
gaggcagcct tagcacgccg tgcgcagcag ggaccggtac gtcgcattct tgtatctctg   3960
ggcatgacgg acgtgggggg aattacagga cgtgtggtcg cacttcttgc cccaatcctt   4020
ggggaggtca ctctggatct tgtggtggga gcgggagccc cgagcttgcc tgctctgcgt   4080
gcattagccg ctgaagaccc tcgccttgtt cttcatattg acacgcagga tatgccacgc   4140
cttgttcttg aagccgactt ggccatcggc gcaggaggtt ccacgacgtg ggagcgctgt   4200
gtccttgcct tgccagcttt gactcttatc ttagccgata accaaattgc cgcggcacgt   4260
gctcttgaag cagctggcgt aaccccttgt ttggacgtaa cagccccgga ttttgacacg   4320
gcctttgcag ctcttgcgca gaacctgatt gctgatccgg atcgtcgtgc cgcacttagt   4380
gctgcctcag ctacggtctg tgatggacgt ggcgcggagc gcgtggctga agcattcttg   4440
ggagtcacca ccacatgaca attgctgcag aagaaggaga tataccatgt ccgctccgag   4500
taccgagatc ccccttcga ttgagattgc tggacgcaag atcggggccg atcacagccc   4560
ctacgttatc tgtgagttgt cgggcaatca taatgggtcc cttgaacgtt gcttagctat   4620
ggtagacgct gccgcagata ccggatgcga cgccatcaaa attcaaactt acacagccga   4680
cacaatcacc ttggatgtag atcgtccgga gttcaaaatc cacgggggat tgtgggatgg   4740
acgcactctg tatgagcttt atgaggaagc tcatactccc tttgagtggc acgcggccat   4800
cttcgaacgc gctcgtcagc gcggtgtcac gatttttttct tctccatttg acgagactgc   4860
cgtcgacctt ttagattcgc tgggggcgcc agcttttaaa attgcaagct ttgaagcggt   4920
agaccttccg cttatcaaat acgcggcagc caaagggaaa cccttaatta tttccactgg   4980
aatggcgaac cttacggaga tgcaaaccgc ccttgataca gctttgtcag caggcgctcc   5040
gggagtgtta cttttacact gtgtttcttc ataccctgct acgttcgcag acgcgaacgt   5100
ccgcaccgtg ccggatatgg cggcacgctt cggatgcccg attggccttt ccgatcacac   5160
gcccggtaca gcagctagtg tcgccgctgt gagcttaggg gcgtgtgcag tagaaaaaca   5220
tttcacgctt gcccgtgccg atggtggtcc ggacgccgca ttctctcttg aacctgcgga   5280
gtttaaggca ttagttgatg acacaaagaa tgcttgggct gcgttgggac gtgcacacta   5340
cgatgtgctg gggtcagagg caacatcact gttattccgc cgttctctgt acgttacagc   5400
cgacgtgaag gctggcgaac ctttaacgcg cgcgaatgtt cgttcagtgc gtcccggcaa   5460
tgggttgcca cctgcggatt tggataaagt tctggcggga aaggcaaccc gcgatcttgc   5520
gcgcggcgag cctcttgact ggtcaatggt cggttgaaac tagtacttaa gaagaaggag   5580
atataccatg atcttggcca tcctgcaagc ccgcatgtca tccacgcgcc ttcctggcaa   5640
ggtactgatg cccctgcaac gccagcccat gatcgttcgt cagatcgaac gtgttgcccg   5700
ctcaaaacgc attgataagt tagttgtggc cacgtcggac cgcccagagg acgatgcaat   5760
cgaagcagcc gttcgccgtg aaggtattgc ggtgtttcgc gggtcattag acaatgtcca   5820
```

```
gcagcgtttt attggggcat tggatgccca ccctgccgac catgtagtac gtctgaccgc   5880
cgattgtccc cttgccgacc cgacacttat tgatgccaca atcgatttat gtctttcaaa   5940
gggcgcggac tacgtatcta atacaccgga gggtcacgcc catccaaaag ggaccgatgt   6000
agaggtaatg accgcagcgg cattgcgtcg cgcggctgct gaagccacga ccaaagaagc   6060
atttgaacac gttacttggg acctttggaa ccaacctcaa cgctggacgt gtgcatggtt   6120
gccgtgcttc ccagatcaag gagcggtacg ctggactgtg gatcgtccgg atgattatgc   6180
ttttgtcgct gctgtatacg atgccctgta cccagcaaat cgcgccttta cgtcggatga   6240
catccgtgcg tttgtcgctg gtcgccccga cctgcaagat tatggtggtg atcgccgtgc   6300
atgagaattc ctcggcctct agaactcgag atcagttctg gaccagcgag ctgtgctgcg   6360
actcgtggcg taatcatggt catagctgtt tcctgtgtga aattgttatc cgctcacaat   6420
tccacacaac atacgagccg gaagcataaa gtgtaaagcc tggggtgcct aatgagtgag   6480
ctaactcaca ttaattgcgt tgcgctcact gcccgctttc cagtcgggaa acctgtcgtg   6540
ccagctgcat taatgaatcg gccaacgcgc ggggagaggc ggtttgcgta ttgggcgctc   6600
ttccgcttcc tcgctcactg actcgctgcg ctcggtcgtt cggctgcggc gagcggtatc   6660
agctcactca aaggcggtaa tacggttatc cacagaatca ggggataacg caggaaagaa   6720
catgtgagca aaaggccagc aaaaggccag gaaccgtaaa aaggccgcgt tgctggcgtt   6780
tttccatagg ctccgccccc ctgacgagca tcacaaaaat cgacgctcaa gtcagaggtg   6840
gcgaaacccg acaggactat aaagatacca ggcgtttccc cctggaagct ccctcgtgcg   6900
ctctcctgtt ccgaccctgt cgcttaccgg atacctgtcc gcctttctcc cttcgggaag   6960
cgtggcgctt tctcatagct cacgctgtag gtatctcagt tcggtgtagg tcgttcgctc   7020
caagctgggc tgtgtgcacg aaccccccgt tcagcccgac cgctgcgcct tatccggtaa   7080
ctatcgtctt gagtccaacc cggtaagaca cgacttatcg ccactggcag cagccactgg   7140
taacaggatt agcagagcga ggtatgtagg cggtgctaca gagttcttga agtggtggcc   7200
taactacggc tacactagaa gaacagtatt tggtatctgc gctctgctga agccagttac   7260
cttcggaaaa agagttggta gctcttgatc cggcaaacaa accaccgctg gtagcggtgg   7320
tttttttgtt tgcaagcagc agattacgcg cagaaaaaaa ggatctcaag aagatccttt   7380
gatcttttct acggggtctg acgctcagtg gaacgaaaac tcacgttaag ggattttggt   7440
catgagatta tcaaaaagga tcttcaccta gatcctttta aattaaaaat gaagttttaa   7500
atcaatctaa agtatatatg agtaaacttg gtctgacagt taccaatgct taatcagtga   7560
ggcacctatc tcagcgatct gtctatttcg ttcatccata gttgcctgac tccccgtcgt   7620
gtagataact acgatacggg agggcttacc atctggcccc agtgctgcaa tgataccgcg   7680
agacccacgc tcaccggctc cagatttatc agcaataaac cagccagccg gaagggccga   7740
gcgcagaagt ggtcctgcaa ctttatccgc ctccatccag tctattaatt gttgccggga   7800
agctagagta agtagttcgc cagttaatag tttgcgcaac gttgttgcca ttgctacagg   7860
catcgtggtg tcacgctcgt cgtttggtat ggcttcattc agctccggtt cccaacgatc   7920
aaggcgagtt acatgatccc ccatgttgtg caaaaaagcg gttagctcct tcggtcctcc   7980
gatcgttgtc agaagtaagt tggccgcagt gttatcactc atggttatgg cagcactgca   8040
taattctctt actgtcatgc catccgtaag atgcttttct gtgactggtg agtactcaac   8100
caagtcattc tgagaatagt gtatgcggcg accgagttgc tcttgcccgg cgtcaatacg   8160
```

```
ggataatacc gcgccacata gcagaacttt aaaagtgctc atcattggaa aacgttcttc   8220

ggggcgaaaa ctctcaagga tcttaccgct gttgagatcc agttcgatgt aacccactcg   8280

tgcacccaac tgatcttcag catcttttac tttcaccagc gtttctgggt gagcaaaaac   8340

aggaaggcaa aatgccgcaa aaaagggaat aagggcgaca cggaaatgtt gaatactcat   8400

actctacctt tttcaatatt attgaagcat ttatcagggt tattgtctca tgagcggata   8460

catatttgaa tgtatttaga aaaataaaca aataggggtt ccgcgcacat ttccccgaaa   8520

agtgccacct gacgtctaag aaaccattat tatcatgaca ttaacctata aaaataggcg   8580

tatcacgagg ccctttcgtc                                               8600
```

<210> SEQ ID NO 21
<211> LENGTH: 2639
<212> TYPE: DNA
<213> ORGANISM: Artificial Sequence
<220> FEATURE:
<223> OTHER INFORMATION: Synthetic sequence

<400> SEQUENCE: 21

```
catatggctc tgaactctat taacaccaac gccggcgcta tgattgcact gcagaacctg     60

aatggtacca actccgagct gacgactgtt cagcagcgta tcaacaccgg taagaaaatt    120

gcgtccgcca aagataacgg cgcaatctgg gctaccgcaa aaaaccaatc tgccactgca    180

gctagcatga acgctgttaa agactccctg cagcgtggcc agtctaccat cgacgttgcc    240

ctggccgccg gtgacactat caccgatctg ctgggtaaaa tgaaagaaaa ggctctggcc    300

gcgtctgaca cctccctgaa taccgcgtct tttaacgccc tgaaatctga cttcgatagc    360

ctgcgtgacc agatcgagaa ggcagcgact aatgctaaat tcaacggtgt tagcatcgcc    420

gacggctcta ccactaaact gaccttcctg gccaactctg acggttctgg tttcaccgtt    480

aacgccaaaa ctatttctct ggctggtatc ggcctgacca ctacctccac ctttaccacc    540

gcggcggcgg cgaagaccat gatcggcact atcgatactg cgctgcagac tgccaccaac    600

aaactggcct ctctgggtac ctcctctgtg ggtctggaca cgcatctgac ttttgtgggc    660

aaactgcagg atagcctgga tgcgggcgtt ggtaacctgg tggatgctga cctggcaaag    720

gagtctgcta agctgcaatc tctgcagact aaacaacagc tgggcgttca ggcactgtcc    780

atcgccaacc aatcttcttc ctctattctg tctctgtttc gctgaattca ggaggtaaaa    840

aaatgtcccg taaaagcgcc ctggaatcct cggcaagcgt cctggcccag gccgatgtcg    900

gcgcttcggg catccaccc agcgttatcg ccgacgccat gggcgattcg gcgtccgccg    960

aggcgctgga gcgcctgaat cgggcggcgc aggacaccaa gaacgtcgac aacgccaagc   1020

acttggcgcg cgcgatccag gccgtgcagc tgcaggacta cgccaaggcc gacaagctgg   1080

ccctgaagct gctggagaag gacgagcgac tgggcctagc ctggcacatc ctggcgattg   1140

cacgcgagaa gaccggcgat ttcgcctcct cgctgcgggc ctatgaagcc gcgctggctc   1200

tgctgcccga ccatggcccc gtcgccggcg acctgggccg cttggccttc cgcatgaaca   1260

tgccggagct ggcggccaag ttcttcgcac actaccgtct cgctcggccc gacgacgtcg   1320

agggcgccaa caacctggcg tgcgccctgc gcgagcttaa tcgcgaaagc gaagccatcg   1380

aagtcctcaa ggccgccctg ggcgccaacc ccgaggctgc ggtgctgtgg aacacgctgg   1440

gcacggtgct ttgcaatatc ggcgacgcgg cgggctcgat cgtgttcttc gacgagtccc   1500

tgcgcctcgc gcccgacttt tcgaaagcct atcacaaccg cgccttcgcc aggctcgatc   1560

tgggcgagat agaggccgcg ctggccgatt gcgaagccgc catgcgcagc cccggctcac   1620
```

cggaagatct ggcgatgatg cagttcgccc gcgccacgat tctcctggct ctgggccgcg 1680
tcggcgaagg ctgggaggct tatgagtcac gcttctcgcc ggcgctgagc gacgcgccac 1740
ggttccagat tcctggcgtc cgctggtcag gacaggacct caggggcaag cgtttgatga 1800
tcaccaccga gcagggcctc ggcgacgagg tgatgttcgc caacatgttg cccgacatcg 1860
tcgaagcctt gggcccagac ggcttcctgt ccctggcggt cgagcgccgt ctggcgccgc 1920
tgttcgagcg caccttcccg aaggtcgagg tgaccgccca ccgtacgatc gcctacgaag 1980
gccgcgtgtt ccgggccgcg ccctatatcg agaactggga ccgcttcgac tattgggcgg 2040
ccatcggcga cttcctgccg agccttcgcc ccaccgccga ggcgtttccc aagcgcaacg 2100
ccttcctgca gccggatccg gcgcgggtgg cccactggaa ggcccaactc gagaagcttg 2160
gccccggccc gaaagtcggc ctgctctgga agagcctgaa actgaacgcg gaacgcgcgc 2220
ggcagttttc gcccttccac ctgtgggagc cggttttgca cacgccaggc gtggtgttcg 2280
tgaacctgca gtatggcgac tgcgaggaag agatcgcctt cgccaaggaa gagctgggcg 2340
tggagatctg gcagccggaa ggcattgatc tgaaggccga cctcgacgac gtggccgctc 2400
tctgcgcggc ggtggacctg gtgatcgggt tctccaacgc cacgatcaat ctggccggtg 2460
cggtggggac gccgatcttc atgctgaccg gcgcctcgtc ctggacccgc ctcggcaccg 2520
aatattaccc ctggtatccg agcgttcgct gcttcgtcac cgagcagtac ggggtctggg 2580
aaccgaccat gggtcgcgtc gccaccgctc tgcgcgattt cgccgcatcc taatctaga 2639

<210> SEQ ID NO 22
<211> LENGTH: 5728
<212> TYPE: DNA
<213> ORGANISM: Artificial Sequence
<220> FEATURE:
<223> OTHER INFORMATION: Synthetic sequence

<400> SEQUENCE: 22
catatggggc gttttagccc aaagagtttg gatctggacg gaaaggttat cttggtaacg 60
ggcggtactg gaagcttcgg gcgtcgtttc atcgagactg tcttgcgccg ttacgatccc 120
cgcaaagtta tcgtctattc gcgcgatgaa ttaaaacaga gtgacatgca aattgagctt 180
cgcgagcaat tcgatgaggc caccgtagca aagatgcgtt tttttctggg cgacgtgcgt 240
gatcgtgagc gtttaacgtt agcgcttcgt ggagtcgaca ttgtcattca tgcagccgca 300
cttaaacagg taccagcggc agaatataat ccctccgaat gtatccacac gaatgtgttg 360
ggtgcggaaa acgtagtatg ggcgtcactg gctaacgccg ttaagcaggt ggtcgcctta 420
tctacggaca aagcttgtaa tccgactaac ctgtatggtg caacgaagtt ggcctctgac 480
aagacgttcg tggctgccaa caatctgagt ggagacatcg ggacccgctt ttgcgtggtt 540
cgctatggta acgtagtcgg gtctcgcggc tcagtagtac cactttatcg tcgtctgttg 600
agccaagggg cgacggagtt gccagtcacg gaccctcgca tgacccgctt ctggattacg 660
ttgaatgagg gcgtggactt cgtactttct tcattgacca tgatgcgcgg aggcgagatt 720
tttgtgccga agatccccag tatggcaatg cctgatttgg taaaagccat gtctagcact 780
gctgcaatga aggtaatcgg tatccgccca ggagagaaac ttcatgaaat catgatcagc 840
gcggatgatg cccgcagcac cgtggagttc gatgaccgct atgcaatcga accgaatttc 900
gcagaatttg gccgtgagcc ctacgcagca agtgacggcg ctaaacccgt ggccgaggac 960
ttcagctaca gctcagacaa taatcatgac tggttgtctc ccgaaggctt gttagccatg 1020

```
ttagaagaga aggccacgtg aagatctccc ccgggaagaa ggagatatac catgacaggc   1080
ggatttttac cttatgggcg tcagactatt gaggaggatg acatcgctgc ggtagcggaa   1140
gcattgcgcg gcgactttct gacgactggc cctacagtgg aagctttcga gacagcgttc   1200
gccgctaaag tcggcgctga tcacgcaatc gcggtatcga acggaacagc taccttgcac   1260
cttgccatga tggctcttgg tattggtgaa ggtgatgtat gcgtagcacc aagtgtgact   1320
tttctggcaa ccgctaactg tgcacgttat gtaggtgcgg aagtagtgtt cgccgacgtt   1380
gacccggaca gtggtcttat gacaccagac accctggcgc gcgctttggc aggtgcacgt   1440
gataagcgtg ttaaagctgt acttccagta catctgcgtg gggacgtatg tgatcttccc   1500
gcgttgaaag caatggcatc agcgagcggc gccgtgcttg tggaagatgc cccgcatgcc   1560
ctgggttcga tcgctacctt tgatggcgta gcgcatccag tcggagatgg tgcgtacagt   1620
tcattcgcaa gtttctcctt tcaccccgta aagacgctgg ccacagggga gggagggatg   1680
ttgaccacca acgaccccgc actggccgca aaggcgcgtt tgcttcgcag tcacgggatg   1740
gtccgccagc cgggtggaga tccgtggtgg tacgagatgc ccgaactggg attcaattac   1800
cgcattcctg atgttttatg tgccttaggt ttatcccaac tggcgaaact tgaccgtttt   1860
gttgcacgcc gtcgtgacct tactgccctt tacgctcgct tattggcgga gcgcgctccc   1920
cgtgcgcgtt tagccaccag cccggaccac tcagacgctg ccttacacct gttgacggtt   1980
ttaattgatt tcgaggccga gggtatttcc cgccgtaccg tagttgaatc ccttaaaact   2040
caaggagtag gaacgcaggt gcactacatc ccggtgcacc gtcagccata ttatgcacag   2100
cgctacgggg tcgccgactt gcccggagct gacgcgtggt acgcccgttg cttaaccttg   2160
ccgctgtatc cagctatgac taatggagac gttgagcgcg ttgtcggtgc tttagccact   2220
gttttagggt gagctagcgg agctcaagaa ggagatatac catggttgcg gtgcgccttc   2280
gtaacctggt cgaatctgat cgcgaacgcc ttcttatttg gcgcaacagt ccagatgtta   2340
gcgcatatat gtactcagat cataagattg gtcacgaaga acatgaccac tggttcgacg   2400
tcgcgcgtca tgacccacgt cgtcgctact ggattatcga ggctgacggg gagccggtcg   2460
gtcttgccaa tcttgctgac attgatttgg ttcaccgtcg ctgtgcttgg gcctactact   2520
tggcaagccc caaagtgcgt ggactgggtg tcggcagttt tgttgagttc caaattatcg   2580
aatacgtttt caatcagttg cacctgaaca aattgtggtg cgaagtcctt atcagtaatg   2640
aatccgtatg gcgtctgcat gaactttacg gcttccagcg cgaggcttta tttcgccagc   2700
atgttatgaa acagggccat gaagtggacg taattggttt aggactgctt gccagtgact   2760
gggccgctcg ccgcgatgcc atggccgaac gcttgtgtgc gaaaggatat acaatccccg   2820
acttgacctg ccgcgcggcc tgagatatcg cggccgcaag aaggagatat accatgtcct   2880
tacgcatcgt ctttgtatgc gcagccggcc catctgtggg tggtggacat gtcatgcgtt   2940
ccttgacact tgcacgcgcg ttagcggcgc gcggagcgac atgtgcgttt ttgggaacac   3000
ccgaggtagc agcagtctta gacgccttcg gtcctgatat ggcgcgtgcc gacaccgccg   3060
agcccttcga agctgtagtc tttgactcct atgcacttac cgcggacgac catcgccgta   3120
tcgcggcggg acgtcccgcg ttagtaatcg acgatttagc cgaccgccct cttgcagcag   3180
acctggtgct tgatgctgga ccggctcgcc gcgccgagga ttacgcagga ctggtgcccg   3240
cacatgcacg tcttctgctg ggtccgaatc acgcaccggt ccgtccagct tttgttgcgt   3300
tacgcgaggc agccttagca cgccgtgcgc agcagggacc ggtacgtcgc attcttgtat   3360
ctctgggcat gacggacgtg gggggaatta caggacgtgt ggtcgcactt cttgccccaa   3420
```

```
tccttgggga ggtcactctg gatcttgtgg tgggagcggg agccccgagc ttgcctgctc   3480
tgcgtgcatt agccgctgaa gaccctcgcc ttgttcttca tattgacacg caggatatgc   3540
cacgccttgt tcttgaagcc gacttggcca tcggcgcagg aggttccacg acgtgggagc   3600
gctgtgtcct tgccttgcca gctttgactc ttatcttagc cgataaccaa attgccgcgg   3660
cacgtgctct tgaagcagct ggcgtaaccc cttgtttgga cgtaacagcc ccggattttg   3720
acacggcctt tgcagctctt gcgcagaacc tgattgctga tccggatcgt cgtgccgcac   3780
ttagtgctgc ctcagctacg gtctgtgatg gacgtggcgc ggagcgcgtg gctgaagcat   3840
tcttgggagt caccaccaca tgacaattgc tgcagaagaa ggagatatac catgtccgct   3900
ccgagtaccg agatcccccc ttcgattgag attgctggac gcaagatcgg ggccgatcac   3960
agcccctacg ttatctgtga gttgtcgggc aatcataatg ggtcccttga acgttgctta   4020
gctatggtag acgctgccgc agataccgga tgcgacgcca tcaaaattca aacttacaca   4080
gccgacacaa tcaccttgga tgtagatcgt ccggagttca aatccacggg ggattgtgg    4140
gatggacgca ctctgtatga gctttatgag gaagctcata ctccctttga gtggcacgcg   4200
gccatcttcg aacgcgctcg tcagcgcggt gtcacgattt tttcttctcc atttgacgag   4260
actgccgtcg accttttaga ttcgctgggg gcgccagctt ttaaaattgc aagctttgaa   4320
gcggtagacc ttccgcttat caaatacgcg gcagccaaag ggaaaccctt aattatttcc   4380
actggaatgg cgaaccttac ggagatgcaa accgcccttg atacagcttt gtcagcaggc   4440
gctccgggag tgttactttt acactgtgtt tcttcatacc ctgctacgtt cgcagacgcg   4500
aacgtccgca ccgtgccgga tatggcggca cgcttcggat gcccgattgg cctttccgat   4560
cacacgcccg gtacagcagc tagtgtcgcc gctgtgagct taggggcgtg tgcagtagaa   4620
aaacatttca cgcttgcccg tgccgatggt ggtccggacg ccgcattctc tcttgaacct   4680
gcggagttta aggcattagt tgatgacaca aagaatgctt gggctgcgtt gggacgtgca   4740
cactacgatg tgctggggtc agaggcaaca tcactgttat tccgccgttc tctgtacgtt   4800
acagccgacg tgaaggctgg cgaacctttta acgcgcgcga atgttcgttc agtgcgtccc   4860
ggcaatgggt tgccacctgc ggatttggat aaagttctgg cgggaaaggc aacccgcgat   4920
cttgcgcgcg gcgagcctct tgactggtca atggtcggtt gaaactagta cttaagaaga   4980
aggagatata ccatgatctt ggccatcctg caagcccgca tgtcatccac gcgccttcct   5040
ggcaaggtac tgatgcccct gcaacgccag cccatgatcg ttcgtcagat cgaacgtgtt   5100
gcccgctcaa aacgcattga taagttagtt gtggccacgt cggaccgccc agaggacgat   5160
gcaatcgaag cagccgttcg ccgtgaaggt attgcggtgt ttcgcgggtc attagacaat   5220
gtccagcagc gttttattgg ggcattggat gcccaccctg ccgaccatgt agtacgtctg   5280
accgccgatt gtccccttgc cgacccgaca cttattgatg ccacaatcga tttatgtctt   5340
tcaaagggcg cggactacgt atctaataca ccggagggtc acgcccatcc aaaagggacc   5400
gatgtagagg taatgaccgc agcggcattg cgtcgcgcgg ctgctgaagc cacgaccaaa   5460
gaagcatttg aacacgttac ttgggacctt tggaaccaac ctcaacgctg gacgtgtgca   5520
tggttgccgt gcttcccaga tcaaggagcg gtacgctgga ctgtggatcg tccggatgat   5580
tatgcttttg tcgctgctgt atacgatgcc ctgtacccag caaatcgcgc ctttacgtcg   5640
gatgacatcc gtgcgtttgt cgctggtcgc cccgacctgc aagattatgg tggtgatcgc   5700
cgtgcatgag aattcctcgg cctctaga                                      5728
```

<210> SEQ ID NO 23
<211> LENGTH: 612
<212> TYPE: PRT
<213> ORGANISM: Artificial Sequence
<220> FEATURE:
<223> OTHER INFORMATION: Mutated FlmG protein sequence

<400> SEQUENCE: 23

```
Met Ser Arg Lys Arg Ala Leu Glu Leu Ser Ala Ser Ala Leu Ala Gln
1               5                   10                  15

Ala Asp Leu Gly Ala Ala Gly Ile His Arg Ala Val Ile Ala Gly Ala
            20                  25                  30

Val Gly Asp Ser Ala Ser Ala Glu Ala Ile Glu Arg Leu Lys Arg Ser
        35                  40                  45

Ala Gln Gln Ile Lys Asn Asn Asp Asn Ala Lys Ala Val Thr Arg Ala
    50                  55                  60

Ile Gln Ala Ile His Leu Arg Asp Tyr Ala Lys Ala Asp Lys Leu Ala
65                  70                  75                  80

Leu Ala Leu Leu Lys Lys Asp Glu His Leu Gly Leu Ala Trp His Ile
                85                  90                  95

Leu Gly Ile Ala Arg Glu Lys Gln Gly Asp Phe Ala Thr Ser Leu Arg
            100                 105                 110

Ala Tyr Glu Ala Ala Leu Lys Leu Leu Ala Asp His Gly Pro Val Ala
        115                 120                 125

Gly Asp Leu Gly Arg Leu Ala Phe Arg Met Asn Met Pro Glu Ile Ala
    130                 135                 140

Ala Gln Phe Phe Ala His Tyr Arg Leu Ala Lys Pro Asp Asp Val Glu
145                 150                 155                 160

Gly Ala Asn Asn Leu Ala Cys Ala Leu Arg Glu Leu Asn Arg Glu Gly
                165                 170                 175

Glu Ala Val Glu Val Leu Lys Ala Ala Ile Gly Ala Asn Pro Thr Ala
            180                 185                 190

Ala Leu Leu Trp Asn Thr Leu Gly Thr Val Leu Cys Asn Val Gly Asp
        195                 200                 205

Ala Gly Gly Ser Leu Val Phe Phe Asp Glu Ala Leu Arg Leu Arg Pro
    210                 215                 220

Asp Phe Ser Lys Ala His His Asn Arg Ala Phe Ala Lys Leu Asp Leu
225                 230                 235                 240

Gly Gln Val Glu Glu Ala Leu Val Asp Cys Glu Ala Ala Ile Lys Ser
                245                 250                 255

Pro Glu Ser Pro Glu Asp Leu Ala Met Met Gln Phe Ala Gln Ala Thr
            260                 265                 270

Ile Leu Leu Gly Leu Gly Arg Val Ala Glu Gly Trp Glu Ala Tyr Glu
        275                 280                 285

Ala Arg Phe Ala Pro Ala Leu Val Glu Ala Pro Arg Phe Gln Ile Pro
    290                 295                 300

Gly Thr Arg Trp Ser Gly Gln Asp Leu Ala Gly Lys Thr Leu Met Ile
305                 310                 315                 320

Ser Thr Glu Gln Gly Leu Gly Asp Glu Val Met Phe Ala Gly Met Leu
                325                 330                 335

Pro Asp Ile Leu Glu Arg Leu Gly Pro Asp Gly Ser Leu Ser Leu Ala
            340                 345                 350

Val Glu Arg Arg Leu Ile Pro Leu Phe Gln Arg Ser Phe Pro Gly Ile
        355                 360                 365
```

Glu Val Thr Ala His Arg Thr Val Ala Tyr Glu Gly Arg Thr Tyr Arg
370 375 380

Ala Ala Pro Glu Ile Glu Asp Trp Asp Arg Phe Asp Tyr Trp Ala Ala
385 390 395 400

Ile Gly Asp Phe Leu Pro Ser Leu Arg Gly Ser Val Glu Ala Phe Pro
405 410 415

Arg Arg Asp His Tyr Leu Thr Pro Asp Pro Glu Arg Val Ala His Trp
420 425 430

Lys Ala Glu Leu Glu Lys Leu Gly Pro Ala Pro Lys Val Gly Leu Leu
435 440 445

Trp Lys Ser Leu Lys Leu Gly Ala Glu Arg Gly Arg Gln Phe Ser Pro
450 455 460

Phe Glu Ala Trp Arg Ala Val Leu Gln Thr Pro Gly Ala Val Phe Val
465 470 475 480

Asn Leu Gln Tyr Gly Asp Cys Asp Glu Glu Ile Ala Tyr Ala Lys Glu
485 490 495

Thr Phe Gly Val Glu Ile Trp Gln Pro Pro Gly Ile Asp Leu Lys Lys
500 505 510

Asp Leu Asp Asp Val Ala Ala Leu Cys Ala Ala Val Asp Leu Ile Ile
515 520 525

Gly Phe Ser Asn Ala Thr Ile Asn Leu Ala Gly Ala Val Gly Ala Pro
530 535 540

Ile Trp Met Met Thr Ala Pro Lys Val Trp Thr Lys Leu Gly Thr Asp
545 550 555 560

Arg Tyr Pro Trp Tyr Pro Gln Ala Gln Val Phe Ser Pro Ala Asp Phe
565 570 575

Ser Asp Trp Glu Pro Val Met Glu Glu Val Ala Arg Ala Leu Ala Ala
580 585 590

Lys Ile Ala Gly Pro Val Met Glu Glu Val Ala Arg Ala Leu Ala Ala
595 600 605

Lys Ile Ala Gly
610

<210> SEQ ID NO 24
<211> LENGTH: 168
<212> TYPE: PRT
<213> ORGANISM: Artificial Sequence
<220> FEATURE:
<223> OTHER INFORMATION: Synthetic sequence

<400> SEQUENCE: 24

Met Ala Leu Asn Ser Ile Asn Thr Asn Ala Gly Ala Met Ile Ala Leu
1 5 10 15

Gln Asn Leu Asn Gly Thr Asn Ser Glu Leu Thr Thr Val Gln Gln Arg
20 25 30

Ile Asn Thr Gly Thr Ser Leu Asn Thr Ala Ser Phe Asn Ala Leu Lys
35 40 45

Ser Asp Phe Asp Ser Leu Arg Asp Gln Ile Glu Lys Ala Ala Thr Asn
50 55 60

Ala Lys Phe Asn Gly Val Ser Ile Ala Asp Gly Ser Thr Thr Lys Leu
65 70 75 80

Thr Phe Leu Ala Asn Ser Asp Gly Ser Gly Phe Thr Val Asn Ala Lys
85 90 95

Thr Ile Ser Leu Ala Gly Ile Gly Leu Thr Thr Thr Ser Thr Phe Thr
100 105 110

```
Thr Ala Ala Ala Ala Lys Thr Met Ile Gly Thr Ile Asp Thr Ala Leu
        115                 120                 125

Gln Thr Ala Thr Asn Lys Leu Ala Ser Leu Gly Thr Ser Ser Val Gly
    130                 135                 140

Leu Asp Thr His Leu Thr Phe Val Gly Lys Leu Gln Asp Ser Leu Asp
145                 150                 155                 160

Ala Gly Val Gly Asn Leu Val Asp
                165


<210> SEQ ID NO 25
<211> LENGTH: 1847
<212> TYPE: PRT
<213> ORGANISM: Artificial Sequence
<220> FEATURE:
<223> OTHER INFORMATION: Synthetic sequence

<400> SEQUENCE: 25

Met Gly Arg Phe Ser Pro Lys Ser Leu Asp Leu Asp Gly Lys Val Ile
1               5                   10                  15

Leu Val Thr Gly Gly Thr Gly Ser Phe Gly Arg Arg Phe Ile Glu Thr
            20                  25                  30

Val Leu Arg Arg Tyr Asp Pro Arg Lys Val Ile Val Tyr Ser Arg Asp
        35                  40                  45

Glu Leu Lys Gln Ser Asp Met Gln Ile Glu Leu Arg Glu Gln Phe Asp
    50                  55                  60

Glu Ala Thr Val Ala Lys Met Arg Phe Phe Leu Gly Asp Val Arg Asp
65                  70                  75                  80

Arg Glu Arg Leu Thr Leu Ala Leu Arg Gly Val Asp Ile Val Ile His
                85                  90                  95

Ala Ala Ala Leu Lys Gln Val Pro Ala Ala Glu Tyr Asn Pro Ser Glu
            100                 105                 110

Cys Ile His Thr Asn Val Leu Gly Ala Glu Asn Val Val Trp Ala Ser
        115                 120                 125

Leu Ala Asn Ala Val Lys Gln Val Val Ala Leu Ser Thr Asp Lys Ala
    130                 135                 140

Cys Asn Pro Thr Asn Leu Tyr Gly Ala Thr Lys Leu Ala Ser Asp Lys
145                 150                 155                 160

Thr Phe Val Ala Ala Asn Asn Leu Ser Gly Asp Ile Gly Thr Arg Phe
                165                 170                 175

Cys Val Val Arg Tyr Gly Asn Val Val Gly Ser Arg Gly Ser Val Val
            180                 185                 190

Pro Leu Tyr Arg Arg Leu Leu Ser Gln Gly Ala Thr Glu Leu Pro Val
        195                 200                 205

Thr Asp Pro Arg Met Thr Arg Phe Trp Ile Thr Leu Asn Glu Gly Val
    210                 215                 220

Asp Phe Val Leu Ser Ser Leu Thr Met Met Arg Gly Gly Glu Ile Phe
225                 230                 235                 240

Val Pro Lys Ile Pro Ser Met Ala Met Pro Asp Leu Val Lys Ala Met
                245                 250                 255

Ser Ser Thr Ala Ala Met Lys Val Ile Gly Ile Arg Pro Gly Glu Lys
            260                 265                 270

Leu His Glu Ile Met Ile Ser Ala Asp Asp Ala Arg Ser Thr Val Glu
        275                 280                 285

Phe Asp Asp Arg Tyr Ala Ile Glu Pro Asn Phe Ala Glu Phe Gly Arg
    290                 295                 300
```

-continued

```
Glu Pro Tyr Ala Ala Ser Asp Gly Ala Lys Pro Val Ala Glu Asp Phe
305                 310                 315                 320

Ser Tyr Ser Ser Asp Asn Asn His Asp Trp Leu Ser Pro Glu Gly Leu
                325                 330                 335

Leu Ala Met Leu Glu Glu Lys Ala Thr Met Thr Gly Gly Phe Leu Pro
            340                 345                 350

Tyr Gly Arg Gln Thr Ile Glu Glu Asp Asp Ile Ala Ala Val Ala Glu
        355                 360                 365

Ala Leu Arg Gly Asp Phe Leu Thr Thr Gly Pro Thr Val Glu Ala Phe
    370                 375                 380

Glu Thr Ala Phe Ala Ala Lys Val Gly Ala Asp His Ala Ile Ala Val
385                 390                 395                 400

Ser Asn Gly Thr Ala Thr Leu His Leu Ala Met Met Ala Leu Gly Ile
                405                 410                 415

Gly Glu Gly Asp Val Cys Val Ala Pro Ser Val Thr Phe Leu Ala Thr
            420                 425                 430

Ala Asn Cys Ala Arg Tyr Val Gly Ala Glu Val Val Phe Ala Asp Val
        435                 440                 445

Asp Pro Asp Ser Gly Leu Met Thr Pro Asp Thr Leu Ala Arg Ala Leu
    450                 455                 460

Ala Gly Ala Arg Asp Lys Arg Val Lys Ala Val Leu Pro Val His Leu
465                 470                 475                 480

Arg Gly Asp Val Cys Asp Leu Pro Ala Leu Lys Ala Met Ala Ser Ala
                485                 490                 495

Ser Gly Ala Val Leu Val Glu Asp Ala Pro His Ala Leu Gly Ser Ile
            500                 505                 510

Ala Thr Phe Asp Gly Val Ala His Pro Val Gly Asp Gly Ala Tyr Ser
        515                 520                 525

Ser Phe Ala Ser Phe Ser Phe His Pro Val Lys Thr Leu Ala Thr Gly
    530                 535                 540

Glu Gly Gly Met Leu Thr Thr Asn Asp Pro Ala Leu Ala Ala Lys Ala
545                 550                 555                 560

Arg Leu Leu Arg Ser His Gly Met Val Arg Gln Pro Gly Gly Asp Pro
                565                 570                 575

Trp Trp Tyr Glu Met Pro Glu Leu Gly Phe Asn Tyr Arg Ile Pro Asp
            580                 585                 590

Val Leu Cys Ala Leu Gly Leu Ser Gln Leu Ala Lys Leu Asp Arg Phe
        595                 600                 605

Val Ala Arg Arg Arg Asp Leu Thr Ala Leu Tyr Ala Arg Leu Leu Ala
    610                 615                 620

Glu Arg Ala Pro Arg Ala Arg Leu Ala Thr Ser Pro Asp His Ser Asp
625                 630                 635                 640

Ala Ala Leu His Leu Leu Thr Val Leu Ile Asp Phe Glu Ala Glu Gly
                645                 650                 655

Ile Ser Arg Arg Thr Val Val Glu Ser Leu Lys Thr Gln Gly Val Gly
            660                 665                 670

Thr Gln Val His Tyr Ile Pro Val His Arg Gln Pro Tyr Tyr Ala Gln
        675                 680                 685

Arg Tyr Gly Val Ala Asp Leu Pro Gly Ala Asp Ala Trp Tyr Ala Arg
    690                 695                 700

Cys Leu Thr Leu Pro Leu Tyr Pro Ala Met Thr Asn Gly Asp Val Glu
705                 710                 715                 720

Arg Val Val Gly Ala Leu Ala Thr Val Leu Gly Met Val Ala Val Arg
```

```
                725                 730                 735

Leu Arg Asn Leu Val Glu Ser Asp Arg Glu Arg Leu Leu Ile Trp Arg
            740                 745                 750

Asn Ser Pro Asp Val Ser Ala Tyr Met Tyr Ser Asp His Lys Ile Gly
        755                 760                 765

His Glu Glu His Asp His Trp Phe Asp Val Ala Arg His Asp Pro Arg
    770                 775                 780

Arg Arg Tyr Trp Ile Ile Glu Ala Asp Gly Glu Pro Val Gly Leu Ala
785                 790                 795                 800

Asn Leu Ala Asp Ile Asp Leu Val His Arg Arg Cys Ala Trp Ala Tyr
                805                 810                 815

Tyr Leu Ala Ser Pro Lys Val Arg Gly Leu Gly Val Gly Ser Phe Val
            820                 825                 830

Glu Phe Gln Ile Ile Glu Tyr Val Phe Asn Gln Leu His Leu Asn Lys
        835                 840                 845

Leu Trp Cys Glu Val Leu Ile Ser Asn Glu Ser Val Trp Arg Leu His
    850                 855                 860

Glu Leu Tyr Gly Phe Gln Arg Glu Ala Leu Phe Arg Gln His Val Met
865                 870                 875                 880

Lys Gln Gly His Glu Val Asp Val Ile Gly Leu Gly Leu Leu Ala Ser
                885                 890                 895

Asp Trp Ala Ala Arg Arg Asp Ala Met Ala Glu Arg Leu Cys Ala Lys
            900                 905                 910

Gly Tyr Thr Ile Pro Asp Leu Thr Cys Arg Ala Ala Met Ser Leu Arg
        915                 920                 925

Ile Val Phe Val Cys Ala Ala Gly Pro Ser Val Gly Gly Gly His Val
    930                 935                 940

Met Arg Ser Leu Thr Leu Ala Arg Ala Leu Ala Ala Arg Gly Ala Thr
945                 950                 955                 960

Cys Ala Phe Leu Gly Thr Pro Glu Val Ala Ala Val Leu Asp Ala Phe
                965                 970                 975

Gly Pro Asp Met Ala Arg Ala Asp Thr Ala Glu Pro Phe Glu Ala Val
            980                 985                 990

Val Phe Asp Ser Tyr Ala Leu Thr  Ala Asp Asp His Arg  Arg Ile Ala
        995                 1000                1005

Ala Gly  Arg Pro Ala Leu Val  Ile Asp Asp Leu Ala  Asp Arg Pro
    1010                 1015                 1020

Leu Ala  Ala Asp Leu Val Leu  Asp Ala Gly Pro Ala  Arg Arg Ala
    1025                 1030                 1035

Glu Asp  Tyr Ala Gly Leu Val  Pro Ala His Ala Arg  Leu Leu Leu
    1040                 1045                 1050

Gly Pro  Asn His Ala Pro Val  Arg Pro Ala Phe Val  Ala Leu Arg
    1055                 1060                 1065

Glu Ala  Ala Leu Ala Arg Arg  Ala Gln Gln Gly Pro  Val Arg Arg
    1070                 1075                 1080

Ile Leu  Val Ser Leu Gly Met  Thr Asp Val Gly Gly  Ile Thr Gly
    1085                 1090                 1095

Arg Val  Val Ala Leu Leu Ala  Pro Ile Leu Gly Glu  Val Thr Leu
    1100                 1105                 1110

Asp Leu  Val Val Gly Ala Gly  Ala Pro Ser Leu Pro  Ala Leu Arg
    1115                 1120                 1125

Ala Leu  Ala Ala Glu Asp Pro  Arg Leu Val Leu His  Ile Asp Thr
    1130                 1135                 1140
```

```
Gln Asp  Met Pro Arg Leu Val  Leu Glu Ala Asp Leu  Ala Ile Gly
    1145                 1150                 1155

Ala Gly  Gly Ser Thr Thr Trp  Glu Arg Cys Val Leu  Ala Leu Pro
    1160                 1165                 1170

Ala Leu  Thr Leu Ile Leu Ala  Asp Asn Gln Ile Ala  Ala Ala Arg
    1175                 1180                 1185

Ala Leu  Glu Ala Ala Gly Val  Thr Pro Cys Leu Asp  Val Thr Ala
    1190                 1195                 1200

Pro Asp  Phe Asp Thr Ala Phe  Ala Ala Leu Ala Gln  Asn Leu Ile
    1205                 1210                 1215

Ala Asp  Pro Asp Arg Arg Ala  Ala Leu Ser Ala Ala  Ser Ala Thr
    1220                 1225                 1230

Val Cys  Asp Gly Arg Gly Ala  Glu Arg Val Ala Glu  Ala Phe Leu
    1235                 1240                 1245

Gly Val  Thr Thr Thr Met Ser  Ala Pro Ser Thr Glu  Ile Pro Pro
    1250                 1255                 1260

Ser Ile  Glu Ile Ala Gly Arg  Lys Ile Gly Ala Asp  His Ser Pro
    1265                 1270                 1275

Tyr Val  Ile Cys Glu Leu Ser  Gly Asn His Asn Gly  Ser Leu Glu
    1280                 1285                 1290

Arg Cys  Leu Ala Met Val Asp  Ala Ala Ala Asp Thr  Gly Cys Asp
    1295                 1300                 1305

Ala Ile  Lys Ile Gln Thr Tyr  Thr Ala Asp Thr Ile  Thr Leu Asp
    1310                 1315                 1320

Val Asp  Arg Pro Glu Phe Lys  Ile His Gly Gly Leu  Trp Asp Gly
    1325                 1330                 1335

Arg Thr  Leu Tyr Glu Leu Tyr  Glu Glu Ala His Thr  Pro Phe Glu
    1340                 1345                 1350

Trp His  Ala Ala Ile Phe Glu  Arg Ala Arg Gln Arg  Gly Val Thr
    1355                 1360                 1365

Ile Phe  Ser Ser Pro Phe Asp  Glu Thr Ala Val Asp  Leu Leu Asp
    1370                 1375                 1380

Ser Leu  Gly Ala Pro Ala Phe  Lys Ile Ala Ser Phe  Glu Ala Val
    1385                 1390                 1395

Asp Leu  Pro Leu Ile Lys Tyr  Ala Ala Ala Lys Gly  Lys Pro Leu
    1400                 1405                 1410

Ile Ile  Ser Thr Gly Met Ala  Asn Leu Thr Glu Met  Gln Thr Ala
    1415                 1420                 1425

Leu Asp  Thr Ala Leu Ser Ala  Gly Ala Pro Gly Val  Leu Leu Leu
    1430                 1435                 1440

His Cys  Val Ser Ser Tyr Pro  Ala Thr Phe Ala Asp  Ala Asn Val
    1445                 1450                 1455

Arg Thr  Val Pro Asp Met Ala  Ala Arg Phe Gly Cys  Pro Ile Gly
    1460                 1465                 1470

Leu Ser  Asp His Thr Pro Gly  Thr Ala Ala Ser Val  Ala Ala Val
    1475                 1480                 1485

Ser Leu  Gly Ala Cys Ala Val  Glu Lys His Phe Thr  Leu Ala Arg
    1490                 1495                 1500

Ala Asp  Gly Gly Pro Asp Ala  Ala Phe Ser Leu Glu  Pro Ala Glu
    1505                 1510                 1515

Phe Lys  Ala Leu Val Asp Asp  Thr Lys Asn Ala Trp  Ala Ala Leu
    1520                 1525                 1530
```

-continued

Gly Arg Ala His Tyr Asp Val Leu Gly Ser Glu Ala Thr Ser Leu
    1535 1540 1545

Leu Phe Arg Arg Ser Leu Tyr Val Thr Ala Asp Val Lys Ala Gly
    1550 1555 1560

Glu Pro Leu Thr Arg Ala Asn Val Arg Ser Val Arg Pro Gly Asn
    1565 1570 1575

Gly Leu Pro Pro Ala Asp Leu Asp Lys Val Leu Ala Gly Lys Ala
    1580 1585 1590

Thr Arg Asp Leu Ala Arg Gly Glu Pro Leu Asp Trp Ser Met Val
    1595 1600 1605

Gly Met Ile Leu Ala Ile Leu Gln Ala Arg Met Ser Ser Thr Arg
    1610 1615 1620

Leu Pro Gly Lys Val Leu Met Pro Leu Gln Arg Gln Pro Met Ile
    1625 1630 1635

Val Arg Gln Ile Glu Arg Val Ala Arg Ser Lys Arg Ile Asp Lys
    1640 1645 1650

Leu Val Val Ala Thr Ser Asp Arg Pro Glu Asp Asp Ala Ile Glu
    1655 1660 1665

Ala Ala Val Arg Arg Glu Gly Ile Ala Val Phe Arg Gly Ser Leu
    1670 1675 1680

Asp Asn Val Gln Gln Arg Phe Ile Gly Ala Leu Asp Ala His Pro
    1685 1690 1695

Ala Asp His Val Val Arg Leu Thr Ala Asp Cys Pro Leu Ala Asp
    1700 1705 1710

Pro Thr Leu Ile Asp Ala Thr Ile Asp Leu Cys Leu Ser Lys Gly
    1715 1720 1725

Ala Asp Tyr Val Ser Asn Thr Pro Glu Gly His Ala His Pro Lys
    1730 1735 1740

Gly Thr Asp Val Glu Val Met Thr Ala Ala Ala Leu Arg Arg Ala
    1745 1750 1755

Ala Ala Glu Ala Thr Thr Lys Glu Ala Phe Glu His Val Thr Trp
    1760 1765 1770

Asp Leu Trp Asn Gln Pro Gln Arg Trp Thr Cys Ala Trp Leu Pro
    1775 1780 1785

Cys Phe Pro Asp Gln Gly Ala Val Arg Trp Thr Val Asp Arg Pro
    1790 1795 1800

Asp Asp Tyr Ala Phe Val Ala Ala Val Tyr Asp Ala Leu Tyr Pro
    1805 1810 1815

Ala Asn Arg Ala Phe Thr Ser Asp Asp Ile Arg Ala Phe Val Ala
    1820 1825 1830

Gly Arg Pro Asp Leu Gln Asp Tyr Gly Gly Asp Arg Arg Ala
    1835 1840 1845

<210> SEQ ID NO 26
<211> LENGTH: 1806
<212> TYPE: DNA
<213> ORGANISM: Artificial Sequence
<220> FEATURE:
<223> OTHER INFORMATION: Synthetic sequence

<400> SEQUENCE: 26
atgtcacgta agagcgcctt ggaaagttcc gcgtcagtct tagctcaggc ggatgtgggc 60
gctagtggca ttcacccttc ggtcatcgcg gacgcgatgg gcgactcagc gtcagccgag 120
gcgttagagc gcttgaatcg tgcggcacag gacacaaaaa atgtcgataa cgcgaaacac 180

-continued

```
ctggctcgcg caattcaagc tgttcaatta caagactacg caaaggcaga caagcttgca    240
ttgaaactgt tggaaaaaga cgagcgcctg ggccttgcct ggcacattct tgccattgct    300
cgcgaaaaaa cgggcgattt cgcttctagc cttcgcgcct acgaggctgc acttgcgctg    360
cttccggatc atggcccggt tgcgggcgac cttggtcgtc ttgcatttcg tatgaacatg    420
ccggagctgg ccgccaagtt cttcgctcac taccgtctgg cgcgtcccga tgacgtggaa    480
ggggcaaata acctggcctg tgccctgcgt gaacttaatc gcgagagcga agcaattgaa    540
gttttgaaag ccgctctggg cgcaaaccca gaggcagcag tgctgtggaa cacattaggg    600
acagtgttgt gcaacatcgg cgatgcggct ggatctatcg tcttctttga tgaatcactg    660
cgcttagccc ctgacttctc gaaagcttac cacaaccgcg cgttcgcccg cttagatctt    720
ggggagattg aagcggcgtt ggcggactgt gaagctgcca tgcgtagtcc cggctcacca    780
gaggacctgg caatgatgca gttcgctcgc gccacaattt tactggcact tgggcgcgtt    840
ggcgaagggt gggaagcgta cgagtcacgc ttttccccgg cattaagcga cgcacctcgt    900
ttccaaattc cgggaacccg ttggtcgggg caagaccttg ctggaaagac actgatgatc    960
tcaactgaac aagggttagg cgacgaagtg atgtttgcag gtatgttacc cgacatcctg   1020
gaacgtcttg gaccagacgg gtccctgtct ctggcagttg agcgccgcct gattccgctg   1080
tttcagcgta gctttcctgg tattgaagtg actgcccacc gcacggttgc atacgaaggt   1140
cgtacctatc gtgctgcccc agagattgag gattgggatc gcttcgatta ttgggccgcg   1200
attggagact tccttccctc cttacgcggg agtgttgaag cattcccgcg tcgcgatcac   1260
tacttgacgc cagatccgga gcgcgttgct cattggaagg cggaacttga aaagttgggc   1320
cctgccccta aagtagggtt attgtggaag agtctgaaat tgggagcaga acgcggacgt   1380
cagttctccc ctttcgaagc atggcgcgca gtacttcaaa cccctggcgc ggttttcgtg   1440
aatctgcagt atggtgattg tgacgaagag atcgcctacg caaaggagac gttcggagtt   1500
gaaatttggc agcccccagg tattgattta aaaaaggatt tggacgatgt tgcagcgtta   1560
tgtgcagcag tcgacttgat tatcggcttc tctaacgcaa ccattaattt ggcgggtgca   1620
gtaggtgcac cgatttggat gatgacagct cctaaggcat ggactaaatt aggaactgat   1680
cgttatccct ggtacccgca ggcgcaggta ttttcaccgg cagattttag cgactgggag   1740
ccagtcatgg aagaagtagc ccgtgcattg gcagctaaaa ttgcgggttg aattctagac   1800
tcgaga                                                              1806
```

<210> SEQ ID NO 27
<211> LENGTH: 596
<212> TYPE: PRT
<213> ORGANISM: Artificial Sequence
<220> FEATURE:
<223> OTHER INFORMATION: Synthetic sequence

<400> SEQUENCE: 27

```
Met Ser Arg Lys Ser Ala Leu Glu Ser Ser Ala Ser Val Leu Ala Gln
1               5                   10                  15

Ala Asp Val Gly Ala Ser Gly Ile His Pro Ser Val Ile Ala Asp Ala
            20                  25                  30

Met Gly Asp Ser Ala Ser Ala Glu Ala Leu Glu Arg Leu Asn Arg Ala
        35                  40                  45

Ala Gln Asp Thr Lys Asn Val Asp Asn Ala Lys His Leu Ala Arg Ala
    50                  55                  60

Ile Gln Ala Val Gln Leu Gln Asp Tyr Ala Lys Ala Asp Lys Leu Ala
```

-continued 65 70 75 80

Leu Lys Leu Leu Glu Lys Asp Glu Arg Leu Gly Leu Ala Trp His Ile
85 90 95

Leu Ala Ile Ala Arg Glu Lys Thr Gly Asp Phe Ala Ser Ser Leu Arg
100 105 110

Ala Tyr Glu Ala Ala Leu Ala Leu Leu Pro Asp His Gly Pro Val Ala
115 120 125

Gly Asp Leu Gly Arg Leu Ala Phe Arg Met Asn Met Pro Glu Leu Ala
130 135 140

Ala Lys Phe Phe Ala His Tyr Arg Leu Ala Arg Pro Asp Asp Val Glu
145 150 155 160

Gly Ala Asn Asn Leu Ala Cys Ala Leu Arg Glu Leu Asn Arg Glu Ser
165 170 175

Glu Ala Ile Glu Val Leu Lys Ala Ala Leu Gly Ala Asn Pro Glu Ala
180 185 190

Ala Val Leu Trp Asn Thr Leu Gly Thr Val Leu Cys Asn Ile Gly Asp
195 200 205

Ala Ala Gly Ser Ile Val Phe Phe Asp Glu Ser Leu Arg Leu Ala Pro
210 215 220

Asp Phe Ser Lys Ala Tyr His Asn Arg Ala Phe Ala Arg Leu Asp Leu
225 230 235 240

Gly Glu Ile Glu Ala Ala Leu Ala Asp Cys Glu Ala Ala Met Arg Ser
245 250 255

Pro Gly Ser Pro Glu Asp Leu Ala Met Met Gln Phe Ala Arg Ala Thr
260 265 270

Ile Leu Leu Ala Leu Gly Arg Val Gly Glu Gly Trp Glu Ala Tyr Glu
275 280 285

Ser Arg Phe Ser Pro Ala Leu Ser Asp Ala Pro Arg Phe Gln Ile Pro
290 295 300

Gly Thr Arg Trp Ser Gly Gln Asp Leu Ala Gly Lys Thr Leu Met Ile
305 310 315 320

Ser Thr Glu Gln Gly Leu Gly Asp Glu Val Met Phe Ala Gly Met Leu
325 330 335

Pro Asp Ile Leu Glu Arg Leu Gly Pro Asp Gly Ser Leu Ser Leu Ala
340 345 350

Val Glu Arg Arg Leu Ile Pro Leu Phe Gln Arg Ser Phe Pro Gly Ile
355 360 365

Glu Val Thr Ala His Arg Thr Val Ala Tyr Glu Gly Arg Thr Tyr Arg
370 375 380

Ala Ala Pro Glu Ile Glu Asp Trp Asp Arg Phe Asp Tyr Trp Ala Ala
385 390 395 400

Ile Gly Asp Phe Leu Pro Ser Leu Arg Gly Ser Val Glu Ala Phe Pro
405 410 415

Arg Arg Asp His Tyr Leu Thr Pro Asp Pro Glu Arg Val Ala His Trp
420 425 430

Lys Ala Glu Leu Glu Lys Leu Gly Pro Ala Pro Lys Val Gly Leu Leu
435 440 445

Trp Lys Ser Leu Lys Leu Gly Ala Glu Arg Gly Arg Gln Phe Ser Pro
450 455 460

Phe Glu Ala Trp Arg Ala Val Leu Gln Thr Pro Gly Ala Val Phe Val
465 470 475 480

Asn Leu Gln Tyr Gly Asp Cys Asp Glu Glu Ile Ala Tyr Ala Lys Glu
485 490 495

```
Thr Phe Gly Val Glu Ile Trp Gln Pro Pro Gly Ile Asp Leu Lys Lys
            500                 505                 510

Asp Leu Asp Asp Val Ala Ala Leu Cys Ala Ala Val Asp Leu Ile Ile
        515                 520                 525

Gly Phe Ser Asn Ala Thr Ile Asn Leu Ala Gly Ala Val Gly Ala Pro
    530                 535                 540

Ile Trp Met Met Thr Ala Pro Lys Ala Trp Thr Lys Leu Gly Thr Asp
545                 550                 555                 560

Arg Tyr Pro Trp Tyr Pro Gln Ala Gln Val Phe Ser Pro Ala Asp Phe
                565                 570                 575

Ser Asp Trp Glu Pro Val Met Glu Glu Val Ala Arg Ala Leu Ala Ala
            580                 585                 590

Lys Ile Ala Gly
        595


<210> SEQ ID NO 28
<211> LENGTH: 10397
<212> TYPE: DNA
<213> ORGANISM: Artificial Sequence
<220> FEATURE:
<223> OTHER INFORMATION: Synthetic sequence

<400> SEQUENCE: 28

tcgcgcgttt cggtgatgac ggtgaaaacc tctgacacat gcagctcccg gagacggtca      60

cagcttgtct gtaagcggat gccgggagca gacaagcccg tcagggcgcg tcagcgggtg     120

ttggcgggtg tcggggctgg cttaactatg cggcatcaga gcagattgta ctgagagtgc     180

accaaatgcg gtgtgaaata ccgcacagat gcgtaaggag aaaataccgc atcaggcgcc     240

attcgccatt caggctgcgc aactgttggg aagggcgatc ggtgcgggcc tcatcgctat     300

tacgccagct ggcgaaaggg ggatgtgctg caaggcgatt aagttgggta acgccagggt     360

tttcccagtc acgacgttgt aaaacgacgg ccagtgcaac gcgatgacga tggatagcga     420

ttcatcgatg agctgacccg atcgccgccg ccggagggtt gcgtttgaga cgggcgacag     480

atggatccgg atgtgagcgg ataacaatta cgagcttcat gcacagtgaa atcatgaaaa     540

atttattggc tttgtgagcg gataacaatt ataatatgtg gaaagaagga gataccatat     600

ggggcgtttt agcccaaaga gtttggatct ggacggaaag gttatcttgg taacgggcgg     660

tactggaagc ttcgggcgtc gtttcatcga gactgtcttg cgccgttacg atccccgcaa     720

agttatcgtc tattcgcgcg atgaattaaa acagagtgac atgcaaattg agcttcgcga     780

gcaattcgat gaggccaccg tagcaaagat gcgttttttt ctgggcgacg tgcgtgatcg     840

tgagcgttta acgttagcgc ttcgtggagt cgacattgtc attcatgcag ccgcacttaa     900

acaggtacca gcggcagaat ataatccctc cgaatgtatc cacacgaatg tgttgggtgc     960

ggaaaacgta gtatgggcgt cactggctaa cgccgttaag caggtggtcg ccttatctac    1020

ggacaaagct tgtaatccga ctaacctgta tggtgcaacg aagttggcct ctgacaagac    1080

gttcgtggct gccaacaatc tgagtggaga catcgggacc cgcttttgcg tggttcgcta    1140

tggtaacgta gtcgggtctc gcggctcagt agtaccactt tatcgtcgtc tgttgagcca    1200

aggggcgacg gagttgccag tcacggaccc tcgcatgacc cgcttctgga ttacgttgaa    1260

tgagggcgtg gacttcgtac tttcttcatt gaccatgatg cgcggaggcg agatttttgt    1320

gccgaagatc cccagtatgg caatgcctga tttggtaaaa gccatgtcta gcactgctgc    1380

aatgaaggta atcggtatcc gcccaggaga gaaacttcat gaaatcatga tcagcgcgga    1440
```

```
tgatgcccgc agcaccgtgg agttcgatga ccgctatgca atcgaaccga atttcgcaga   1500
atttggccgt gagccctacg cagcaagtga cggcgctaaa cccgtggccg aggacttcag   1560
ctacagctca gacaataatc atgactggtt gtctcccgaa ggcttgttag ccatgttaga   1620
agagaaggcc acgtgaagat ctcccccggg aagaaggaga tataccatga caggcggatt   1680
tttaccttat gggcgtcaga ctattgagga ggatgacatc gctgcggtag cggaagcatt   1740
gcgcggcgac tttctgacga ctggccctac agtggaagct ttcgagacag cgttcgccgc   1800
taaagtcggc gctgatcacg caatcgcggt atcgaacgga acagctacct tgcaccttgc   1860
catgatggct cttggtattg gtgaaggtga tgtatgcgta gcaccaagtg tgacttttct   1920
ggcaaccgct aactgtgcac gttatgtagg tgcggaagta gtgttcgccg acgttgaccc   1980
ggacagtggt cttatgacac cagacaccct ggcgcgcgct ttggcaggtg cacgtgataa   2040
gcgtgttaaa gctgtacttc cagtacatct gcgtggggac gtatgtgatc ttcccgcgtt   2100
gaaagcaatg gcatcagcga gcggcgccgt gcttgtggaa gatgccccgc atgccctggg   2160
ttcgatcgct acctttgatg gcgtagcgca tccagtcgga gatggtgcgt acagttcatt   2220
cgcaagtttc tcctttcacc ccgtaaagac gctggccaca ggggagggag ggatgttgac   2280
caccaacgac cccgcactgg ccgcaaaggc gcgtttgctt cgcagtcacg ggatggtccg   2340
ccagccgggt ggagatccgt ggtggtacga gatgcccgaa ctgggattca attaccgcat   2400
tcctgatgtt ttatgtgcct taggtttatc ccaactggcg aaacttgacc gttttgttgc   2460
acgccgtcgt gaccttactg ccctttacgc tcgcttattg gcggagcgcg ctccccgtgc   2520
gcgtttagcc accagcccgg accactcaga cgctgcctta cacctgttga cggttttaat   2580
tgatttcgag gccgagggta tttcccgccg taccgtagtt gaatccctta aaactcaagg   2640
agtaggaacg caggtgcact acatcccggt gcaccgtcag ccatattatg cacagcgcta   2700
cggggtcgcc gacttgcccg gagctgacgc gtggtacgcc cgttgcttaa ccttgccgct   2760
gtatccagct atgactaatg gagacgttga gcgcgttgtc ggtgctttag ccactgtttt   2820
agggtgagct agcggagctc aagaaggaga tataccatgg ttgcggtgcg ccttcgtaac   2880
ctggtcgaat ctgatcgcga acgccttctt atttggcgca acagtccaga tgttagcgca   2940
tatatgtact cagatcataa gattggtcac gaagaacatg accactggtt cgacgtcgcg   3000
cgtcatgacc cacgtcgtcg ctactggatt atcgaggctg acggggagcc ggtcggtctt   3060
gccaatcttg ctgacattga tttggttcac cgtcgctgtg cttgggccta ctacttggca   3120
agccccaaag tgcgtggact gggtgtcggc agttttgttg agttccaaat tatcgaatac   3180
gttttcaatc agttgcacct gaacaaattg tggtgcgaag tccttatcag taatgaatcc   3240
gtatggcgtc tgcatgaact ttacggcttc cagcgcgagg ctttatttcg ccagcatgtt   3300
atgaaacagg gccatgaagt ggacgtaatt ggtttaggac tgcttgccag tgactgggcc   3360
gctcgccgcg atgccatggc cgaacgcttg tgtgcgaaag gatatacaat ccccgacttg   3420
acctgccgcg cggcctgaga tatcgcggcc gcaagaagga gatataccat gtccttacgc   3480
atcgtctttg tatgcgcagc cggcccatct gtgggtggtg gacatgtcat gcgttccttg   3540
acacttgcac gcgcgttagc ggcgcgcgga gcgacatgtg cgtttttggg aacacccgag   3600
gtagcagcag tcttagacgc cttcggtcct gatatggcgc gtgccgacac cgccgagccc   3660
ttcgaagctg tagtctttga ctcctatgca cttaccgcgg acgaccatcg ccgtatcgcg   3720
gcgggacgtc ccgcgttagt aatcgacgat ttagccgacc gccctcttgc agcagacctg   3780
```

gtgcttgatg ctggaccggc tcgccgcgcc gaggattacg caggactggt gcccgcacat 3840
gcacgtcttc tgctgggtcc gaatcacgca ccggtccgtc cagcttttgt tgcgttacgc 3900
gaggcagcct tagcacgccg tgcgcagcag ggaccggtac gtcgcattct tgtatctctg 3960
ggcatgacgg acgtgggggg aattacagga cgtgtggtcg cacttcttgc cccaatcctt 4020
ggggaggtca ctctggatct tgtggtggga gcgggagccc cgagcttgcc tgctctgcgt 4080
gcattagccg ctgaagaccc tcgccttgtt cttcatattg acacgcagga tatgccacgc 4140
cttgttcttg aagccgactt ggccatcggc gcaggaggtt ccacgacgtg ggagcgctgt 4200
gtccttgcct tgccagcttt gactcttatc ttagccgata accaaattgc cgcggcacgt 4260
gctcttgaag cagctggcgt aaccccttgt ttggacgtaa cagccccgga ttttgacacg 4320
gcctttgcag ctcttgcgca gaacctgatt gctgatccgg atcgtcgtgc cgcacttagt 4380
gctgcctcag ctacggtctg tgatggacgt ggcgcggagc gcgtggctga agcattcttg 4440
ggagtcacca ccacatgaca attgctgcag aagaaggaga tataccatgt ccgctccgag 4500
taccgagatc ccccttcga ttgagattgc tggacgcaag atcggggccg atcacagccc 4560
ctacgttatc tgtgagttgt cgggcaatca taatgggtcc cttgaacgtt gcttagctat 4620
ggtagacgct gccgcagata ccggatgcga cgccatcaaa attcaaactt acacagccga 4680
cacaatcacc ttggatgtag atcgtccgga gttcaaaatc cacgggggat tgtgggatgg 4740
acgcactctg tatgagcttt atgaggaagc tcatactccc tttgagtggc acgcggccat 4800
cttcgaacgc gctcgtcagc gcggtgtcac gatttttct tctccatttg acgagactgc 4860
cgtcgacctt ttagattcgc tgggggcgcc agcttttaaa attgcaagct ttgaagcggt 4920
agaccttccg cttatcaaat acgcggcagc caaagggaaa cccttaatta tttccactgg 4980
aatggcgaac cttacggaga tgcaaaccgc ccttgataca gctttgtcag caggcgctcc 5040
gggagtgtta cttttacact gtgtttcttc ataccctgct acgttcgcag acgcgaacgt 5100
ccgcaccgtg ccggatatgg cggcacgctt cggatgcccg attggccttt ccgatcacac 5160
gcccggtaca gcagctagtg tcgccgctgt gagcttaggg gcgtgtgcag tagaaaaaca 5220
tttcacgctt gcccgtgccg atggtggtcc ggacgccgca ttctctcttg aacctgcgga 5280
gtttaaggca ttagttgatg acacaaagaa tgcttgggct gcgttgggac gtgcacacta 5340
cgatgtgctg gggtcagagg caacatcact gttattccgc cgttctctgt acgttacagc 5400
cgacgtgaag gctggcgaac ctttaacgcg cgcgaatgtt cgttcagtgc gtcccggcaa 5460
tgggttgcca cctgcggatt tggataaagt tctggcggga aaggcaaccc gcgatcttgc 5520
gcgcggcgag cctcttgact ggtcaatggt cggttgaaac tagtacttaa gaagaaggag 5580
atataccatg atcttggcca tcctgcaagc ccgcatgtca tccacgcgcc ttcctggcaa 5640
ggtactgatg cccctgcaac gccagcccat gatcgttcgt cagatcgaac gtgttgcccg 5700
ctcaaaacgc attgataagt tagttgtggc cacgtcggac cgcccagagg acgatgcaat 5760
cgaagcagcc gttcgccgtg aaggtattgc ggtgtttcgc gggtcattag acaatgtcca 5820
gcagcgtttt attggggcat tggatgccca ccctgccgac catgtagtac gtctgaccgc 5880
cgattgtccc cttgccgacc cgacacttat tgatgccaca atcgatttat gtctttcaaa 5940
gggcgcggac tacgtatcta atacaccgga gggtcacgcc catccaaaag ggaccgatgt 6000
agaggtaatg accgcagcgg cattgcgtcg cgcggctgct gaagccacga ccaaagaagc 6060
atttgaacac gttacttggg acctttggaa ccaacctcaa cgctggacgt gtgcatggtt 6120
gccgtgcttc ccagatcaag gagcggtacg ctggactgtg gatcgtccgg atgattatgc 6180

```
ttttgtcgct gctgtatacg atgccctgta cccagcaaat cgcgccttta cgtcggatga   6240
catccgtgcg tttgtcgctg gtcgccccga cctgcaagat tatggtggtg atcgccgtgc   6300
atgagaattc aggaggtaaa aaaatgtccc gtaaaagcgc cctggaatcc tcggcaagcg   6360
tcctggccca ggccgatgtc ggcgcttcgg gcatccaccc cagcgttatc gccgacgcca   6420
tgggcgattc ggcgtccgcc gaggcgctgg agcgcctgaa tcgggcggcg caggacacca   6480
agaacgtcga caacgccaag cacttggcgc gcgcgatcca ggccgtgcag ctgcaggact   6540
acgccaaggc cgacaagctg gccctgaagc tgctggagaa ggacgagcga ctgggcctag   6600
cctggcacat cctggcgatt gcacgcgaga agaccggcga tttcgcctcc tcgctgcggg   6660
cctatgaagc cgcgctggct ctgctgcccg accatggccc cgtcgccggc gacctgggcc   6720
gcttggcctt ccgcatgaac atgccggagc tggcggccaa gttcttcgca cactaccgtc   6780
tcgctcggcc cgacgacgtc gagggcgcca acaacctggc gtgcgccctg cgcgagctta   6840
atcgcgaaag cgaagccatc gaagtcctca aggccgccct gggcgccaac cccgaggctg   6900
cggtgctgtg gaacacgctg ggcacggtgc tttgcaatat cggcgacgcg gcgggctcga   6960
tcgtgttctt cgacgagtcc ctgcgcctcg cgcccgactt ttcgaaagcc tatcacaacc   7020
gcgccttcgc caggctcgat ctgggcgaga tagaggccgc gctggccgat tgcgaagccg   7080
ccatgcgcag ccccggctca ccggaagatc tggcgatgat gcagttcgcc cgcgccacga   7140
ttctcctggc tctgggccgc gtcggcgaag gctgggaggc ttatgagtca cgcttctcgc   7200
cggcgctgag cgacgcgcca cggttccaga ttcctggcgt ccgctggtca ggacaggacc   7260
tcaggggcaa gcgtttgatg atcaccaccg agcagggcct cggcgacgag gtgatgttcg   7320
ccaacatgtt gcccgacatc gtcgaagcct tgggcccaga cggcttcctg tccctggcgg   7380
tcgagcgccg tctggcgccg ctgttcgagc gcaccttccc gaaggtcgag gtgaccgccc   7440
accgtacgat cgcctacgaa ggccgcgtgt tccgggccgc gccctatatc gagaactggg   7500
accgcttcga ctattgggcg gccatcggcg acttcctgcc gagccttcgc cccaccgccg   7560
aggcgtttcc caagcgcaac gccttcctgc agccggatcc ggcgcgggtg gcccactgga   7620
aggcccaact cgagaagctt ggccccggcc cgaaagtcgg cctgctctgg aagagcctga   7680
aactgaacgc ggaacgcgcg cggcagtttt cgcccttcca cctgtgggag ccggttttgc   7740
acacgccagg cgtggtgttc gtgaacctgc agtatggcga ctgcgaggaa gagatcgcct   7800
tcgccaagga agagctgggc gtggagatct ggcagccgga aggcattgat ctgaaggccg   7860
acctcgacga cgtggccgct ctctgcgcgg cggtggacct ggtgatcggg ttctccaacg   7920
ccacgatcaa tctggccggt gcggtgggga cgccgatctt catgctgacc ggcgcctcgt   7980
cctggacccg cctcggcacc gaatattacc cctggtatcc gagcgttcgc tgcttcgtca   8040
ccgagcagta cggggtctgg gaaccgacca tgggtcgcgt cgccaccgct ctgcgcgatt   8100
tcgccgcatc ctgatctaga actcgagatc agttctggac cagcgagctg tgctgcgact   8160
cgtggcgtaa tcatggtcat agctgtttcc tgtgtgaaat tgttatccgc tcacaattcc   8220
acacaacata cgagccggaa gcataaagtg taaagcctgg ggtgcctaat gagtgagcta   8280
actcacatta attgcgttgc gctcactgcc cgctttccag tcgggaaacc tgtcgtgcca   8340
gctgcattaa tgaatcggcc aacgcgcggg gagaggcggt ttgcgtattg ggcgctcttc   8400
cgcttcctcg ctcactgact cgctgcgctc ggtcgttcgg ctgcggcgag cggtatcagc   8460
tcactcaaag gcggtaatac ggttatccac agaatcaggg gataacgcag gaaagaacat   8520
```

gtgagcaaaa ggccagcaaa aggccaggaa ccgtaaaaag gccgcgttgc tggcgttttt 8580
ccataggctc cgcccccctg acgagcatca caaaaatcga cgctcaagtc agaggtggcg 8640
aaacccgaca ggactataaa gataccaggc gtttccccct ggaagctccc tcgtgcgctc 8700
tcctgttccg accctgtcgc ttaccggata cctgtccgcc tttctccctt cgggaagcgt 8760
ggcgctttct catagctcac gctgtaggta tctcagttcg gtgtaggtcg ttcgctccaa 8820
gctgggctgt gtgcacgaac cccccgttca gcccgaccgc tgcgccttat ccggtaacta 8880
tcgtcttgag tccaacccgg taagacacga cttatcgcca ctggcagcag ccactggtaa 8940
caggattagc agagcgaggt atgtaggcgg tgctacagag ttcttgaagt ggtggcctaa 9000
ctacggctac actagaagaa cagtatttgg tatctgcgct ctgctgaagc cagttacctt 9060
cggaaaaaga gttggtagct cttgatccgg caaacaaacc accgctggta gcggtggttt 9120
ttttgtttgc aagcagcaga ttacgcgcag aaaaaaagga tctcaagaag atcctttgat 9180
cttttctacg gggtctgacg ctcagtggaa cgaaaactca cgttaaggga ttttggtcat 9240
gagattatca aaaaggatct tcacctagat ccttttaaat taaaaatgaa gttttaaatc 9300
aatctaaagt atatatgagt aaacttggtc tgacagttac caatgcttaa tcagtgaggc 9360
acctatctca gcgatctgtc tatttcgttc atccatagtt gcctgactcc ccgtcgtgta 9420
gataactacg atacgggagg gcttaccatc tggccccagt gctgcaatga taccgcgaga 9480
cccacgctca ccggctccag atttatcagc aataaaccag ccagccggaa gggccgagcg 9540
cagaagtggt cctgcaactt tatccgcctc catccagtct attaattgtt gccgggaagc 9600
tagagtaagt agttcgccag ttaatagttt gcgcaacgtt gttgccattg ctacaggcat 9660
cgtggtgtca cgctcgtcgt ttggtatggc ttcattcagc tccggttccc aacgatcaag 9720
gcgagttaca tgatccccca tgttgtgcaa aaaagcggtt agctccttcg gtcctccgat 9780
cgttgtcaga agtaagttgg ccgcagtgtt atcactcatg gttatggcag cactgcataa 9840
ttctcttact gtcatgccat ccgtaagatg cttttctgtg actggtgagt actcaaccaa 9900
gtcattctga gaatagtgta tgcggcgacc gagttgctct tgcccggcgt caatacggga 9960
taataccgcg ccacatagca gaactttaaa agtgctcatc attggaaaac gttcttcggg 10020
gcgaaaactc tcaaggatct taccgctgtt gagatccagt tcgatgtaac ccactcgtgc 10080
acccaactga tcttcagcat cttttacttt caccagcgtt tctgggtgag caaaaacagg 10140
aaggcaaaat gccgcaaaaa agggaataag ggcgacacgg aaatgttgaa tactcatact 10200
ctaccttttt caatattatt gaagcattta tcagggttat tgtctcatga gcggatacat 10260
atttgaatgt atttagaaaa ataaacaaat aggggttccg cgcacatttc cccgaaaagt 10320
gccacctgac gtctaagaaa ccattattat catgacatta acctataaaa ataggcgtat 10380
cacgaggccc tttcgtc 10397

<210> SEQ ID NO 29
<211> LENGTH: 10397
<212> TYPE: DNA
<213> ORGANISM: Artificial Sequence
<220> FEATURE:
<223> OTHER INFORMATION: Synthetic sequence

<400> SEQUENCE: 29
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180

-continued accaaatgcg gtgtgaaata ccgcacagat gcgtaaggag aaaataccgc atcaggcgcc 240
attcgccatt caggctgcgc aactgttggg aagggcgatc ggtgcgggcc tcatcgctat 300
tacgccagct ggcgaaaggg ggatgtgctg caaggcgatt aagttgggta acgccagggt 360
tttcccagtc acgacgttgt aaaacgacgg ccagtgcaac gcgatgacga tggatagcga 420
ttcatcgatg agctgacccg atcgccgccg ccggagggtt gcgtttgaga cgggcgacag 480
atggatccgg atgtgagcgg ataacaatta cgagcttcat gcacagtgaa atcatgaaaa 540
atttattggc tttgtgagcg gataacaatt ataatatgtg gaaagaagga gataccatat 600
ggggcgtttt agcccaaaga gtttggatct ggacggaaag gttatcttgg taacgggcgg 660
tactggaagc ttcgggcgtc gtttcatcga gactgtcttg cgccgttacg atccccgcaa 720
agttatcgtc tattcgcgcg atgaattaaa acagagtgac atgcaaattg agcttcgcga 780
gcaattcgat gaggccaccg tagcaaagat gcgttttttt ctgggcgacg tgcgtgatcg 840
tgagcgttta acgttagcgc ttcgtggagt cgacattgtc attcatgcag ccgcacttaa 900
acaggtacca gcggcagaat ataatccctc cgaatgtatc cacacgaatg tgttgggtgc 960
ggaaaacgta gtatgggcgt cactggctaa cgccgttaag caggtggtcg ccttatctac 1020
ggacaaagct tgtaatccga ctaacctgta tggtgcaacg aagttggcct ctgacaagac 1080
gttcgtggct gccaacaatc tgagtggaga catcgggacc cgcttttgcg tggttcgcta 1140
tggtaacgta gtcgggtctc gcggctcagt agtaccactt tatcgtcgtc tgttgagcca 1200
aggggcgacg gagttgccag tcacggaccc tcgcatgacc cgcttctgga ttacgttgaa 1260
tgagggcgtg gacttcgtac tttcttcatt gaccatgatg cgcggaggcg agatttttgt 1320
gccgaagatc cccagtatgg caatgcctga tttggtaaaa gccatgtcta gcactgctgc 1380
aatgaaggta atcggtatcc gcccaggaga gaaacttcat gaaatcatga tcagcgcgga 1440
tgatgcccgc agcaccgtgg agttcgatga ccgctatgca atcgaaccga atttcgcaga 1500
atttggccgt gagccctacg cagcaagtga cggcgctaaa cccgtggccg aggacttcag 1560
ctacagctca gacaataatc atgactggtt gtctcccgaa ggcttgttag ccatgttaga 1620
agagaaggcc acgtgaagat ctcccccggg aagaaggaga tataccatga caggcggatt 1680
tttaccttat gggcgtcaga ctattgagga ggatgacatc gctgcggtag cggaagcatt 1740
gcgcggcgac tttctgacga ctggccctac agtggaagct ttcgagacag cgttcgccgc 1800
taaagtcggc gctgatcacg caatcgcggt atcgaacgga acagctacct tgcaccttgc 1860
catgatggct cttggtattg gtgaaggtga tgtatgcgta gcaccaagtg tgacttttct 1920
ggcaaccgct aactgtgcac gttatgtagg tgcggaagta gtgttcgccg acgttgaccc 1980
ggacagtggt cttatgacac cagacaccct ggcgcgcgct ttggcaggtg cacgtgataa 2040
gcgtgttaaa gctgtacttc cagtacatct gcgtggggac gtatgtgatc ttcccgcgtt 2100
gaaagcaatg gcatcagcga gcggcgccgt gcttgtggaa gatgccccgc atgccctggg 2160
ttcgatcgct acctttgatg gcgtagcgca tccagtcgga gatggtgcgt acagttcatt 2220
cgcaagtttc tcctttcacc ccgtaaagac gctggccaca ggggagggag ggatgttgac 2280
caccaacgac cccgcactgg ccgcaaaggc gcgtttgctt cgcagtcacg ggatggtccg 2340
ccagccgggt ggagatccgt ggtggtacga gatgcccgaa ctgggattca attaccgcat 2400
tcctgatgtt ttatgtgcct taggtttatc ccaactggcg aaacttgacc gttttgttgc 2460
acgccgtcgt gaccttactg ccctttacgc tcgcttattg gcggagcgcg ctccccgtgc 2520

-continued

```
gcgtttagcc accagcccgg accactcaga cgctgcctta cacctgttga cggttttaat   2580
tgatttcgag gccgagggta tttcccgccg taccgtagtt gaatccctta aaactcaagg   2640
agtaggaacg caggtgcact acatcccggt gcaccgtcag ccatattatg cacagcgcta   2700
cggggtcgcc gacttgcccg gagctgacgc gtggtacgcc cgttgcttaa ccttgccgct   2760
gtatccagct atgactaatg gagacgttga gcgcgttgtc ggtgctttag ccactgtttt   2820
agggtgagct agcggagctc aagaaggaga tataccatgg ttgcggtgcg ccttcgtaac   2880
ctggtcgaat ctgatcgcga acgccttctt atttggcgca acagtccaga tgttagcgca   2940
tatatgtact cagatcataa gattggtcac gaagaacatg accactggtt cgacgtcgcg   3000
cgtcatgacc cacgtcgtcg ctactggatt atcgaggctg acggggagcc ggtcggtctt   3060
gccaatcttg ctgacattga tttggttcac cgtcgctgtg cttgggccta ctacttggca   3120
agccccaaag tgcgtggact gggtgtcggc agttttgttg agttccaaat tatcgaatac   3180
gttttcaatc agttgcacct gaacaaattg tggtgcgaag tccttatcag taatgaatcc   3240
gtatggcgtc tgcatgaact ttacggcttc cagcgcgagg ctttatttcg ccagcatgtt   3300
atgaaacagg gccatgaagt ggacgtaatt ggtttaggac tgcttgccag tgactgggcc   3360
gctcgccgcg atgccatggc cgaacgcttg tgtgcgaaag gatatacaat ccccgacttg   3420
acctgccgcg cggcctgaga tatcgcggcc gcaagaagga gatataccat gtccttacgc   3480
atcgtctttg tatgcgcagc cggcccatct gtgggtggtg gacatgtcat gcgttccttg   3540
acacttgcac gcgcgttagc ggcgcgcgga gcgacatgtg cgtttttggg aacacccgag   3600
gtagcagcag tcttagacgc cttcggtcct gatatggcgc gtgccgacac cgccgagccc   3660
ttcgaagctg tagtctttga ctcctatgca cttaccgcgg acgaccatcg ccgtatcgcg   3720
gcgggacgtc ccgcgttagt aatcgacgat ttagccgacc gccctcttgc agcagacctg   3780
gtgcttgatg ctggaccggc tcgccgcgcc gaggattacg caggactggt gcccgcacat   3840
gcacgtcttc tgctgggtcc gaatcacgca ccggtccgtc cagcttttgt tgcgttacgc   3900
gaggcagcct tagcacgccg tgcgcagcag ggaccggtac gtcgcattct tgtatctctg   3960
ggcatgacgg acgtgggggg aattacagga cgtgtggtcg cacttcttgc cccaatcctt   4020
ggggaggtca ctctggatct tgtggtggga gcgggagccc cgagcttgcc tgctctgcgt   4080
gcattagccg ctgaagaccc tcgccttgtt cttcatattg acacgcagga tatgccacgc   4140
cttgttcttg aagccgactt ggccatcggc gcaggaggtt ccacgacgtg ggagcgctgt   4200
gtccttgcct tgccagcttt gactcttatc ttagccgata accaaattgc cgcggcacgt   4260
gctcttgaag cagctggcgt aaccccttgt ttggacgtaa cagccccgga ttttgacacg   4320
gcctttgcag ctcttgcgca gaacctgatt gctgatccgg atcgtcgtgc cgcacttagt   4380
gctgcctcag ctacggtctg tgatggacgt ggcgcggagc gcgtggctga agcattcttg   4440
ggagtcacca ccacatgaca attgctgcag aagaaggaga tataccatgt ccgctccgag   4500
taccgagatc ccccccttcga ttgagattgc tggacgcaag atcggggccg atcacagccc   4560
ctacgttatc tgtgagttgt cgggcaatca taatgggtcc cttgaacgtt gcttagctat   4620
ggtagacgct gccgcagata ccggatgcga cgccatcaaa attcaaactt acacagccga   4680
cacaatcacc ttggatgtag atcgtccgga gttcaaaatc cacgggggat tgtgggatgg   4740
acgcactctg tatgagcttt atgaggaagc tcatactccc tttgagtggc acgcggccat   4800
cttcgaacgc gctcgtcagc gcggtgtcac gatttttttct tctccatttg acgagactgc   4860
cgtcgacctt ttagattcgc tgggggcgcc agcttttaaa attgcaagct ttgaagcggt   4920
```

-continued agaccttccg cttatcaaat acgcggcagc caaagggaaa cccttaatta tttccactgg 4980
aatggcgaac cttacggaga tgcaaaccgc ccttgataca gctttgtcag caggcgctcc 5040
gggagtgtta cttttacact gtgtttcttc ataccctgct acgttcgcag acgcgaacgt 5100
ccgcaccgtg ccggatatgg cggcacgctt cggatgcccg attggccttt ccgatcacac 5160
gcccggtaca gcagctagtg tcgccgctgt gagcttaggg gcgtgtgcag tagaaaaaca 5220
tttcacgctt gcccgtgccg atggtggtcc ggacgccgca ttctctcttg aacctgcgga 5280
gtttaaggca ttagttgatg acacaaagaa tgcttgggct gcgttgggac gtgcacacta 5340
cgatgtgctg gggtcagagg caacatcact gttattccgc cgttctctgt acgttacagc 5400
cgacgtgaag gctggcgaac ctttaacgcg cgcgaatgtt cgttcagtgc gtcccggcaa 5460
tgggttgcca cctgcggatt tggataaagt tctggcggga aaggcaaccc gcgatcttgc 5520
gcgcggcgag cctcttgact ggtcaatggt cggttgaaac tagtacttaa gaagaaggag 5580
atataccatg atcttggcca tcctgcaagc ccgcatgtca tccacgcgcc ttcctggcaa 5640
ggtactgatg cccctgcaac gccagcccat gatcgttcgt cagatcgaac gtgttgcccg 5700
ctcaaaacgc attgataagt tagttgtggc cacgtcggac cgcccagagg acgatgcaat 5760
cgaagcagcc gttcgccgtg aaggtattgc ggtgtttcgc gggtcattag acaatgtcca 5820
gcagcgtttt attggggcat tggatgccca ccctgccgac catgtagtac gtctgaccgc 5880
cgattgtccc cttgccgacc cgacacttat tgatgccaca atcgatttat gtctttcaaa 5940
gggcgcggac tacgtatcta atacaccgga gggtcacgcc catccaaaag ggaccgatgt 6000
agaggtaatg accgcagcgg cattgcgtcg cgcggctgct gaagccacga ccaaagaagc 6060
atttgaacac gttacttggg acctttggaa ccaacctcaa cgctggacgt gtgcatggtt 6120
gccgtgcttc ccagatcaag gagcggtacg ctggactgtg gatcgtccgg atgattatgc 6180
ttttgtcgct gctgtatacg atgccctgta cccagcaaat cgcgccttta cgtcggatga 6240
catccgtgcg tttgtcgctg gtcgccccga cctgcaagat tatggtggtg atcgccgtgc 6300
atgagaattc aggaggtaaa aaaatgtcac gtaagagcgc cttggaaagt tccgcgtcag 6360
tcttagctca ggcggatgtg ggcgctagtg gcattcaccc ttcggtcatc gcggacgcga 6420
tgggcgactc agcgtcagcc gaggcgttag agcgcttgaa tcgtgcggca caggacacaa 6480
aaaatgtcga taacgcgaaa cacctggctc gcgcaattca agctgttcaa ttacaagact 6540
acgcaaaggc agacaagctt gcattgaaac tgttggaaaa agacgagcgc ctgggccttg 6600
cctggcacat tcttgccatt gctcgcgaaa aaacgggcga tttcgcttct agccttcgcg 6660
cctacgaggc tgcacttgcg ctgcttccgg atcatggccc ggttgcgggc gaccttggtc 6720
gtcttgcatt tcgtatgaac atgccggagc tggccgccaa gttcttcgct cactaccgtc 6780
tggcgcgtcc cgatgacgtg gaaggggcaa ataacctggc ctgtgccctg cgtgaactta 6840
atcgcgagag cgaagcaatt gaagttttga aagccgctct gggcgcaaac ccagaggcag 6900
cagtgctgtg gaacacatta gggacagtgt tgtgcaacat cggcgatgcg gctggatcta 6960
tcgtcttctt tgatgaatca ctgcgcttag cccctgactt ctcgaaagct taccacaacc 7020
gcgcgttcgc ccgcttagat cttggggaga ttgaagcggc gttggcggac tgtgaagctg 7080
ccatgcgtag tcccggctca ccagaggacc tggcaatgat gcagttcgct cgcgccacaa 7140
ttttactggc acttgggcgc gttggcgaag ggtgggaagc gtacgagtca cgcttttccc 7200
ccgcattaag cgacgcacct cgtttccaaa ttccgggaac ccgttggtcg gggcaagacc 7260

-continued

```
ttgctggaaa gacactgatg atctcaactg aacaagggtt aggcgacgaa gtgatgtttg   7320
caggtatgtt acccgacatc ctggaacgtc ttggaccaga cgggtccctg tctctggcag   7380
ttgagcgccg cctgattccg ctgtttcagc gtagctttcc tggtattgaa gtgactgccc   7440
accgcacggt tgcatacgaa ggtcgtacct atcgtgctgc cccagagatt gaggattggg   7500
atcgcttcga ttattgggcc gcgattggag acttccttcc ctccttacgc gggagtgttg   7560
aagcattccc gcgtcgcgat cactacttga cgccagatcc ggagcgcgtt gctcattgga   7620
aggcggaact tgaaaagttg ggccctgccc ctaaagtagg gttattgtgg aagagtctga   7680
aattgggagc agaacgcgga cgtcagttct cccctttcga agcatggcgc gcagtacttc   7740
aaacccctgg cgcggttttc gtgaatctgc agtatggtga ttgtgacgaa gagatcgcct   7800
acgcaaagga gacgttcgga gttgaaattt ggcagccccc aggtattgat ttaaaaaagg   7860
atttggacga tgttgcagcg ttatgtgcag cagtcgactt gattatcggc ttctctaacg   7920
caaccattaa tttggcgggt gcagtaggtg caccgatttg gatgatgaca gctcctaagg   7980
catggactaa attaggaact gatcgttatc cctggtaccc gcaggcgcag gtattttcac   8040
cggcagattt tagcgactgg gagccagtca tggaagaagt agcccgtgca ttggcagcta   8100
aaattgcggg ttgatctaga actcgagatc agttctggac cagcgagctg tgctgcgact   8160
cgtggcgtaa tcatggtcat agctgtttcc tgtgtgaaat tgttatccgc tcacaattcc   8220
acacaacata cgagccggaa gcataaagtg taaagcctgg ggtgcctaat gagtgagcta   8280
actcacatta attgcgttgc gctcactgcc cgctttccag tcgggaaacc tgtcgtgcca   8340
gctgcattaa tgaatcggcc aacgcgcggg gagaggcggt ttgcgtattg ggcgctcttc   8400
cgcttcctcg ctcactgact cgctgcgctc ggtcgttcgg ctgcggcgag cggtatcagc   8460
tcactcaaag gcggtaatac ggttatccac agaatcaggg gataacgcag gaaagaacat   8520
gtgagcaaaa ggccagcaaa aggccaggaa ccgtaaaaag gccgcgttgc tggcgttttt   8580
ccataggctc cgcccccctg acgagcatca caaaaatcga cgctcaagtc agaggtggcg   8640
aaacccgaca ggactataaa gataccaggc gtttccccct ggaagctccc tcgtgcgctc   8700
tcctgttccg accctgtcgc ttaccggata cctgtccgcc tttctccctt cgggaagcgt   8760
ggcgctttct catagctcac gctgtaggta tctcagttcg gtgtaggtcg ttcgctccaa   8820
gctgggctgt gtgcacgaac cccccgttca gcccgaccgc tgcgccttat ccggtaacta   8880
tcgtcttgag tccaacccgg taagacacga cttatcgcca ctggcagcag ccactggtaa   8940
caggattagc agagcgaggt atgtaggcgg tgctacagag ttcttgaagt ggtggcctaa   9000
ctacggctac actagaagaa cagtatttgg tatctgcgct ctgctgaagc cagttacctt   9060
cggaaaaaga gttggtagct cttgatccgg caaacaaacc accgctggta gcggtggttt   9120
ttttgtttgc aagcagcaga ttacgcgcag aaaaaaagga tctcaagaag atcctttgat   9180
cttttctacg gggtctgacg ctcagtggaa cgaaaactca cgttaaggga ttttggtcat   9240
gagattatca aaaaggatct tcacctagat ccttttaaat taaaaatgaa gttttaaatc   9300
aatctaaagt atatatgagt aaacttggtc tgacagttac caatgcttaa tcagtgaggc   9360
acctatctca gcgatctgtc tatttcgttc atccatagtt gcctgactcc ccgtcgtgta   9420
gataactacg atacgggagg gcttaccatc tggccccagt gctgcaatga taccgcgaga   9480
cccacgctca ccggctccag atttatcagc aataaaccag ccagccggaa gggccgagcg   9540
cagaagtggt cctgcaactt tatccgcctc catccagtct attaattgtt gccgggaagc   9600
tagagtaagt agttcgccag ttaatagttt gcgcaacgtt gttgccattg ctacaggcat   9660
```

```
cgtggtgtca cgctcgtcgt ttggtatggc ttcattcagc tccggttccc aacgatcaag   9720

gcgagttaca tgatccccca tgttgtgcaa aaaagcggtt agctccttcg gtcctccgat   9780

cgttgtcaga agtaagttgg ccgcagtgtt atcactcatg gttatggcag cactgcataa   9840

ttctcttact gtcatgccat ccgtaagatg cttttctgtg actggtgagt actcaaccaa   9900

gtcattctga gaatagtgta tgcggcgacc gagttgctct tgcccggcgt caatacggga   9960

taataccgcg ccacatagca gaactttaaa agtgctcatc attggaaaac gttcttcggg  10020

gcgaaaactc tcaaggatct taccgctgtt gagatccagt tcgatgtaac ccactcgtgc  10080

acccaactga tcttcagcat cttttacttt caccagcgtt tctgggtgag caaaaacagg  10140

aaggcaaaat gccgcaaaaa agggaataag ggcgacacgg aaatgttgaa tactcatact  10200

ctaccttttt caatattatt gaagcattta tcagggttat tgtctcatga gcggatacat  10260

atttgaatgt atttagaaaa ataaacaaat aggggttccg cgcacatttc cccgaaaagt  10320

gccacctgac gtctaagaaa ccattattat catgacatta acctataaaa ataggcgtat  10380

cacgaggccc tttcgtc                                                 10397
```

<210> SEQ ID NO 30
<211> LENGTH: 825
<212> TYPE: DNA
<213> ORGANISM: Artificial Sequence
<220> FEATURE:
<223> OTHER INFORMATION: Synthetic sequence

<400> SEQUENCE: 30

```
atggcgctga atagcatcaa taccaatgca ggggccatga tcgcgttaca aaacttaaac     60

gggacaaact ccgaactgac aacagttcag cagcgcatca ataccggcaa aaaaatcgcc    120

tctgccaaag acaacggggc tatttgggct accgccaaga atcagagtgc gaccgccgcg    180

agcatgaatg ctgtgaagga ttcattgcaa cgcggtcaga gcactattga cgtggcatta    240

gcggctggcg acacaatcac ggatctgtta ggcaaaatga aggaaaaagc tctggctgcc    300

agtgacacta gccttaatac cgcatccttc aatgcgttaa agagcgattt cgacagcctg    360

cgtgatcaga ttgagaaggc cgctacaaac gcaaagttta acggagttaa cctgcttgat    420

aatagtacgg gcacgggcgg gtataaagcg ttgtccaaca ctgctggatc aacgattaaa    480

gttgccgggg agaacttatc tttaggtatc gggttaacca ccacgtccac tttcacaact    540

gctgccgccg caaagactat gatcggcacc atcgacacag cattgcaaac tgctacaaat    600

aaattggctt ctctgggcac atcctcggtg gggttagaca cgcatcttac ctttgtaggg    660

aagctgcagg attctctgga cgccggtgta ggcaatctgg tagatgcgga cttagcaaag    720

gagagtgcca aattacagtc gttacagaca aagcaacaac ttggcgtgca agcactgtcc    780

atcgcaaatc agtcttcctc atctattctg tcattgttcc gctga                    825
```

<210> SEQ ID NO 31
<211> LENGTH: 274
<212> TYPE: PRT
<213> ORGANISM: Artificial Sequence
<220> FEATURE:
<223> OTHER INFORMATION: Synthetic sequence

<400> SEQUENCE: 31

```
Met Ala Leu Asn Ser Ile Asn Thr Asn Ala Gly Ala Met Ile Ala Leu
1               5                   10                  15

Gln Asn Leu Asn Gly Thr Asn Ser Glu Leu Thr Thr Val Gln Gln Arg
```

```
            20                  25                  30

Ile Asn Thr Gly Lys Lys Ile Ala Ser Ala Lys Asp Asn Gly Ala Ile
        35                  40                  45

Trp Ala Thr Ala Lys Asn Gln Ser Ala Thr Ala Ala Ser Met Asn Ala
    50                  55                  60

Val Lys Asp Ser Leu Gln Arg Gly Gln Ser Thr Ile Asp Val Ala Leu
65                  70                  75                  80

Ala Ala Gly Asp Thr Ile Thr Asp Leu Leu Gly Lys Met Lys Glu Lys
                85                  90                  95

Ala Leu Ala Ala Ser Asp Thr Ser Leu Asn Thr Ala Ser Phe Asn Ala
            100                 105                 110

Leu Lys Ser Asp Phe Asp Ser Leu Arg Asp Gln Ile Glu Lys Ala Ala
        115                 120                 125

Thr Asn Ala Lys Phe Asn Gly Val Asn Leu Leu Asp Asn Ser Thr Gly
    130                 135                 140

Thr Gly Gly Tyr Lys Ala Leu Ser Asn Thr Ala Gly Ser Thr Ile Lys
145                 150                 155                 160

Val Ala Gly Glu Asn Leu Ser Leu Gly Ile Gly Leu Thr Thr Thr Ser
                165                 170                 175

Thr Phe Thr Thr Ala Ala Ala Ala Lys Thr Met Ile Gly Thr Ile Asp
            180                 185                 190

Thr Ala Leu Gln Thr Ala Thr Asn Lys Leu Ala Ser Leu Gly Thr Ser
        195                 200                 205

Ser Val Gly Leu Asp Thr His Leu Thr Phe Val Gly Lys Leu Gln Asp
    210                 215                 220

Ser Leu Asp Ala Gly Val Gly Asn Leu Val Asp Ala Asp Leu Ala Lys
225                 230                 235                 240

Glu Ser Ala Lys Leu Gln Ser Leu Gln Thr Lys Gln Gln Leu Gly Val
                245                 250                 255

Gln Ala Leu Ser Ile Ala Asn Gln Ser Ser Ser Ser Ile Leu Ser Leu
            260                 265                 270

Phe Arg
```

<210> SEQ ID NO 32
<211> LENGTH: 831
<212> TYPE: DNA
<213> ORGANISM: Artificial Sequence
<220> FEATURE:
<223> OTHER INFORMATION: Synthetic sequence

<400> SEQUENCE: 32

```
atggccttga acagcgtgaa taccaattcg ggggcattag tagcacttca aaacctgcaa      60

tccacgaaca gtgagttagc gacagtacag agtcgtatta acacgggtaa aaaagtgaac     120

agcgccaaag acaacggtgc cgtttgggcc attgcacagg ggcaacgctc cgaggtcaat     180

gctcttggcg cagtcaagga ttccttagcg cgtgggtcga gcgctgtcga tgtctcgatt     240

gcggcaggag aaagcgtgtc tgatttactg ttacagttaa aagaaaaagc gttgagcgcc     300

accgataagt cgcttacgac ggcggcgcgc actgccttga acgaggattt taaggccatc     360

cgcgatcaga ttactacggt tgtaacaaat gccaagttca atggcgtctc tattgcagac     420

gggagtacca ccaagctgac gtttttggct aattcagatg gttcgggctt cactgtcaac     480

gctaaaacca tcagccttgc tgggggtacc aacgtaaccg tcgctactac aacgactatc     540

gggacgtcaa ccttggctac taccgccctg gggctggtaa acgcttcaat cgacaaagtc     600
```

```
tcggcctctt tagcccgtct gggtacggga gcgaaggctc tggacactca tagcacattt    660

gttggaaagt tatcggatgc gctggagaat ggcattggca acttagttga cgctgacctt    720

gcaaaagagt ctgctcgcct gcaaagttta cagacgaagc aacagttggg ggttcaggcg    780

ttgagcatcg ctaaccaatc gtcttctatt cttctgggtc ttttccgctg a             831


<210> SEQ ID NO 33
<211> LENGTH: 276
<212> TYPE: PRT
<213> ORGANISM: Artificial Sequence
<220> FEATURE:
<223> OTHER INFORMATION: Synthetic sequence

<400> SEQUENCE: 33

Met Ala Leu Asn Ser Val Asn Thr Asn Ser Gly Ala Leu Val Ala Leu
1               5                   10                  15

Gln Asn Leu Gln Ser Thr Asn Ser Glu Leu Ala Thr Val Gln Ser Arg
            20                  25                  30

Ile Asn Thr Gly Lys Lys Val Asn Ser Ala Lys Asp Asn Gly Ala Val
        35                  40                  45

Trp Ala Ile Ala Gln Gly Gln Arg Ser Glu Val Asn Ala Leu Gly Ala
    50                  55                  60

Val Lys Asp Ser Leu Ala Arg Gly Ser Ser Ala Val Asp Val Ser Ile
65                  70                  75                  80

Ala Ala Gly Glu Ser Val Ser Asp Leu Leu Leu Gln Leu Lys Glu Lys
                85                  90                  95

Ala Leu Ser Ala Thr Asp Lys Ser Leu Thr Thr Ala Ala Arg Thr Ala
            100                 105                 110

Leu Asn Glu Asp Phe Lys Ala Ile Arg Asp Gln Ile Thr Thr Val Val
        115                 120                 125

Thr Asn Ala Lys Phe Asn Gly Val Ser Ile Ala Asp Gly Ser Thr Thr
    130                 135                 140

Lys Leu Thr Phe Leu Ala Asn Ser Asp Gly Ser Gly Phe Thr Val Asn
145                 150                 155                 160

Ala Lys Thr Ile Ser Leu Ala Gly Gly Thr Asn Val Thr Val Ala Thr
                165                 170                 175

Thr Thr Thr Ile Gly Thr Ser Thr Leu Ala Thr Thr Ala Leu Gly Leu
            180                 185                 190

Val Asn Ala Ser Ile Asp Lys Val Ser Ala Ser Leu Ala Arg Leu Gly
        195                 200                 205

Thr Gly Ala Lys Ala Leu Asp Thr His Ser Thr Phe Val Gly Lys Leu
    210                 215                 220

Ser Asp Ala Leu Glu Asn Gly Ile Gly Asn Leu Val Asp Ala Asp Leu
225                 230                 235                 240

Ala Lys Glu Ser Ala Arg Leu Gln Ser Leu Gln Thr Lys Gln Gln Leu
                245                 250                 255

Gly Val Gln Ala Leu Ser Ile Ala Asn Gln Ser Ser Ser Ile Leu Leu
            260                 265                 270

Gly Leu Phe Arg
        275
```